US012582699B2

(12) United States Patent
Lum et al.

(10) Patent No.: US 12,582,699 B2
(45) Date of Patent: Mar. 24, 2026

(54) COMPOSITIONS AND METHODS FOR ENHANCED LYMPHOCYTE-MEDIATED IMMUNOTHERAPY

(71) Applicants: Provincial Health Services Authority, Vancouver (CA); UNIVERSITÉ LAVAL, Québec (CA)

(72) Inventors: Julian J. Lum, Victoria (CA); Lindsay Devorkin, Burnaby (CA); Yannick Doyon, Québec (CA); Gillian Carleton, Victoria (CA)

(73) Assignees: Provincial Health Services Authority, Vancouver (CA); Université Laval, Quebec (CA)

( * ) Notice: Subject to any disclaimer, the term of this patent is extended or adjusted under 35 U.S.C. 154(b) by 1202 days.

(21) Appl. No.: 17/430,055

(22) PCT Filed: Feb. 12, 2020

(86) PCT No.: PCT/CA2020/050185
§ 371 (c)(1),
(2) Date: Aug. 11, 2021

(87) PCT Pub. No.: WO2020/163953
PCT Pub. Date: Aug. 20, 2020

(65) Prior Publication Data
US 2022/0133793 A1 May 5, 2022

Related U.S. Application Data

(60) Provisional application No. 62/804,658, filed on Feb. 12, 2019.

(51) Int. Cl.
| | |
|---|---|
| *A61K 40/11* | (2025.01) |
| *A61K 38/17* | (2006.01) |
| *A61K 40/31* | (2025.01) |
| *A61K 40/42* | (2025.01) |
| *A61P 35/00* | (2006.01) |
| *C07H 21/02* | (2006.01) |
| *C12N 5/0783* | (2010.01) |
| *C12N 15/90* | (2006.01) |

(52) U.S. Cl.
CPC .......... *A61K 38/1774* (2013.01); *A61K 40/11* (2025.01); *A61K 40/31* (2025.01); *A61K 40/4202* (2025.01); *A61P 35/00* (2018.01); *C07H 21/02* (2013.01); *C12N 5/0638* (2013.01); *C12N 15/907* (2013.01)

(58) Field of Classification Search
CPC .... A61K 40/11; A61K 40/31; A61K 40/4202; C12N 5/0638; C12N 2510/00
See application file for complete search history.

(56) References Cited

U.S. PATENT DOCUMENTS

2013/0184223 A1 7/2013 Land et al.
2018/0369282 A1 12/2018 Nishio et al.

FOREIGN PATENT DOCUMENTS

CN 108472314 A 8/2018
WO 2015161276 A2 10/2015

OTHER PUBLICATIONS

Pua et al. A critical role for the autophagy gene Atg5 in T cell survival and proliferation. JEM, vol. 204, No. 1, p. 25-31 (Year: 2007).*
Jia et al. Autophagy regulates T lymphocyte proliferation through selective degradation of the cell-cycle inhibitor CDKN1B/p27Kip1. Autophagy 11:12, 2335-2345 (Year: 2015).*
Li et al. Autophagy Is Induced in CD4+ T Cells and Important for the Growth Factor-Withdrawal Cell Death. The Journal of Immunology, 2006, 177: 5163-5168 (Year: 2006).*
Pua et al. A critical role for the autophagy gene Atg5 in T cell survival and proliferation. JEM. vol. 204, No. 1, Jan. 22, 2007 25-31 (Year: 2007).*
Almasbak et al. CAR T Cell Therapy: A Game Changer in Cancer Treatment. Journal of Immunology Research. vol. 2016, Article ID 5474602, pp. 1-10 (Year: 2016).*
Lopez-Cantillo et al. CAR-T Cell Performance: How to Improve Their Persistence? Front. Immunol. 13:878209. p. 1-16 (Year: 2022).*
Inhibition of Autophagy in the Tumour Microenvironment Enhances Anti-Tumour Immunity, DeVorkin et al., 2016 EMBO Symposium "Tumour Microenvironment and Signalling". Apr. 3-6, 2016.
Autophagy Suppresses CD8+ T Cell Anti-Tumor Immunity, DeVorkin et al., Keystone Symposium "Autophagy Network Integration in Health and Disease". Feb. 12-16, 2017.
Autophagy Inhibition Enhances CD8+ T Cell Anti-Tumour Immunity, DeVorkin et al., Keystone Symposium "Integrating Metabolism and Immunity". May 29-Jun. 2, 2017.
Autophagy Suppresses CD8+ T Cell Anti-Tumour Responses Through Glucose-Dependent Changes in Transcription, DeVorkin et al., Keystone Symposium "Tumor Metabolism". Feb. 24-28, 2019.
Invited talk: Genentech. San Francisco. May 24, 2017.

(Continued)

*Primary Examiner* — Taeyoon Kim
(74) *Attorney, Agent, or Firm* — Viridant IP

(57) ABSTRACT

Lymphocytes having a suppressed autophagy gene useful in immunotherapy are disclosed. The lymphocytes can express an antigen targeting receptor such as a chimeric antigen receptor (CAR) or endogenous or engineered T-cell receptor to target cells expressing a tumor-specific antigen. Methods of making and using such lymphocytes are disclosed. Some such lymphocytes are useful in conducting CAR-T or TCR-T therapy.

19 Claims, 18 Drawing Sheets
Specification includes a Sequence Listing.

(56) References Cited

OTHER PUBLICATIONS

All-in-one metabolic engineering of chimeric antigen receptor T cells for cancer immunotherapy, Carleton et al., BCMB Symposium Abstract, Dec. 2019.

Metabolic Engineering of CAR-T Cells for Cancer Immunotherapy, G. Carleton, BCMB580, Nov. 2019.

Metabolic engineering of chimeric antigen receptor T cells for cancer immunotherapy, Carleton et al., BioCanRx Abstract, May 2019.

Metabolic Engineering of CAR-T Cells for Cancer Immunotherapy, G. Carleton, BioCanRx Presentation, Oct. 2019.

All-in-one metabolic engineering of chimeric antigen receptor T cells for cancer immunotherapy, Carleton et al., Keystone Abstract, Oct. 2019.

Metabolic Engineering of Chimeric Antigen Receptor T Cells for Cancer Immunotherapy, G. Carleton, BCMB Grad Symposium, Feb. 2019.

Autophagy-associated immune responses and cancer immunotherapy, Pan et al., Oncotarget 7(16), 21235-21246, 2016.

Chimeric antigen receptor-engineered T cells for immunotherapy of cancer, Cartellieri et al., J. Biomedicine and Biotechnol., 2010, 956304.

Application of CRISPR/Cas9 to autophagy research, O'Prey et al., Methods in Enzymology, 588: 79-108, ISSN 0076-6879, 2017.

Geyer MB, Brentjens RJ. 2016. Review: Current clinical applications of chimeric antigen receptor (CAR) modified T cells. Cytotherapy 18: 1393-409.

Kershaw MH, et al., 2006. A phase I study on adoptive immunotherapy using gene-modified T cells for ovarian cancer. Clin Cancer Res 12: 6106-15.

Zhao Z, et al., 2015. Structural Design of Engineered Costimulation Determines Tumor Rejection Kinetics and Persistence of CAR T Cells. Cancer Cell 28: 415-28.

Milne K, et al., 2009. Systematic analysis of immune infiltrates in high-grade serous ovarian cancer reveals CD20, FoxP3 and TIA-1 as positive prognostic factors. PLoS One 4: e6412.

Cheung A, et al., 2016. Targeting folate receptor alpha for cancer treatment. Oncotarget.

Newick K, et al., 2017. CAR T Cell Therapy for Solid Tumors. Annu Rev Med 68: 139-52.

Townsend KN, et al., 2013. Markers of T cell infiltration and function associate with favorable outcome in vascularized high-grade serous ovarian carcinoma. PLoS One 8: e82406.

Vander Heiden MG, DeBerardinis RJ. 2017. Understanding the Intersections between Metabolism and Cancer Biology. Cell 168: 657-69.

Chang CH, Pearce EL. 2016. Emerging concepts of T cell metabolism as a target of immunotherapy. Nat Immunol17:364-8.

Chang CH, et al., 2015. Metabolic Competition in the Tumor Microenvironment Is a Driver of Cancer Progression. Cell 162: 1229-41.

MacPherson S, et al., 2017. STAT3 regulation of citrate synthase is essential during the initiation of lymphocyte cell growth. Cell Rep. 19(5):910-918.

Ma EH, et al., 2017. Serine Is an Essential Metabolite for Effector T Cell Expansion. Cell Metab 25: 345-57.

Scharping NE, et al., 2016. The Tumor Microenvironment Represses T Cell Mitochondrial Biogenesis to Drive Intratumoral T Cell Metabolic Insufficiency and Dysfunction. Immunity.

Lum JJ, DeBerardinis RJ, Thompson CB. 2005. Autophagy in metazoans: cell survival in the land of plenty. Nat Rev Mol Cell Biol 6: 439-48.

Pua HH, He YW. 2009. Autophagy and lymphocyte homeostasis. Curr Top Microbiol Immunol 335: 85-105.

Schlie K, et al., 2015. Survival of effector CD8+ T cells during influenza infection is dependent on autophagy. J Immunol 194: 4277-86.

Puleston DJ, et al., 2014. Autophagy is a critical regulator of memory CD8+ T cell formation. Elife 3.

Qu X, et al., 2003. Promotion of tumorigenesis by heterozygous disruption of the beclin 1 autophagy gene. J Clin Invest 112: 1809-20.

Takamura A, et al., 2011. Autophagy-deficient mice develop multiple liver tumors. Genes Dev 25: 795-800.

Macintyre AN, et al., 2014. The glucose transporter Glut1 is selectively essential for CD4 T cell activation and effector function. Cell Metab 20: 61-72.

Hultquist JF, et al., 2016. A Cas9 Ribonucleoprotein Platform for Functional Genetic Studies of HIV-Host Interactions in Primary Human T Cells. Cell Rep 17: 1438-52.

Eyquem J, et al., 2017. Targeting a CAR to the TRAC locus with CRISPR/Cas9 enhances tumour rejection. Nature 543: 113-7.

DeVorkin L, et al., 2019. Autophagy regulation of metabolism is required for CD8+ T-cell anti-tumour immunity. Cell Rep 27(2):502-513.

Stadtmauer, EA, et al., 2020. CRISPR-engineered T cells in patients with refractory cancer. Science Feb. 6, 2020. DOI: 10.1126/science. aba7365.

Schlie et al., 2015. Survival of effector CD8+ T-Cells during influenza infection is dependent on autophagy. J. Immunol. 194(9):4277-4286.

Wei J, Long L, Yang K, Guy C, Shrestha S, Chen Z, Wu C, Vogel P, Neale G, Green DR, Chi H. Autophagy enforces functional integrity of regulatory T cells by coupling environmental cues and metabolic homeostasis. Nat Immunol. Mar. 2016;17(3):277-85. doi: 10.1038/ni.3365. Epub Jan. 25, 2016. PubMed PMID: 26808230; PubMed Central PMCID: PMC4755832.

Rao S, Tortola L, Perlot T, Wirsberger G, Novatchkova M, Nitsch R, Sykacek P, Frank L, Schramek D, Komnenovic V, Sigl V, Aumayr K, Schmauss G, Fellner N, Handschuh S, Glösmann M, Pasierbek P, Schlederer M, Resch GP, Ma Y, Yang H, Popper H, Kenner L, Kroemer G, Penninger JM. A dual role for autophagy in a murine model of lung cancer. Nat Commun. 2014;5:3056. doi: 10.1038/ncomms4056. PubMed PMID: 24445999.

Chen S, Wang C, Yeo S, Liang CC, Okamoto T, Sun S, Wen J, Guan JL. Distinct roles of autophagy-dependent and -independent functions of FIP200 revealed by generation and analysis of a mutant knock-in mouse model. Genes Dev. Apr. 1, 2016;30(7):856-69. doi: 10.1101/gad.276428.115. Epub Mar. 24, 2016. PubMed PMID: 27013233; PubMed Central PMCID: PMC4826400.

Salah FS, Ebbinghaus M, Muley VY, Zhou Z, Al-Saadi KR, Pacyna-Gengelback M, O'Sullivan Gao, Betz H, Konig R, Wang Z-Q, Brauer R, Petersen I. Tumor suppression in mice lacking GABARAP, an Atg8/LC3 family member implicated in autophagy, is associated with alterations in cytokine secretion and cell death. Cell Death Dis. 2016. 7: e2205. Doi: 10.1038/cddis.2016.93. PubMed PMID: 27124579, PubMed Central PMCID: PMC4855672.

Mirzaei et al., "Gene-knocked out chimeric antigen receptor (CAR) T Cells: Tuning up for the next generation cancer immunotherapy", Cancer Letters, vol. 423, Jun. 1, 2018, pp. 95-104.

Karch et al., "Autophagic cell death is dependent on lysosomal membrane permeability through Bax and Bak", Elife, vol. 6, No. e30543, Nov. 17, 2017.

Liang et al., "Autophagy Genes as Tumor Suppressors", Curr Opin Cell Biol, 22(2), 226-233, 2010.

Jiang et al., "The relationship between autophagy and the immune system and its applications for tumor immunotherapy", Molecular Cancer, 18:17, 1-22, 2019.

* cited by examiner

70

76

72

100

102

104

106

108

A

B

A

C

D

B

Target 719 (20 bp)    NGG

I2A

GCTCCAGCTACGGAAAGTCAGATTACTGGAGG    SEQ ID NO:12

CGAGGTCGATGCCTTTCAGTCTAATGACCTCC    SEQ ID NO:13

GGN    Target 696 (20 bp)

I2A

CAGGCTCCTCAAGTGGTACTACTCGGTGCATG    SEQ ID NO:14

GTCCGAGGAGTTCACCATGATGAGCCACGTAC    SEQ ID NO:15

GGN    Target 824 (20 bp)

Target 950 (20 bp)    NGG

I2A

AGAGAAGTTCGGCAATCTTGTTACTGGTACTC    SEQ ID NO:16

TCTCTTCAAGCCGTTAGAACAATGACCATGAG    SEQ ID NO:17

I2B

TGGACCCTTAACATTAGGCAGCGATCCGTTTA    SEQ ID NO:18

ACCTGGGAATTGTAATCCGTCGCTAGGCAAAT    SEQ ID NO:19

GGN    Target 905 (20 bp)

I2B

CGATCCGTTTATGTATCCTTAGTCAGGTGT    SEQ ID NO:20

GCTAGGCAAATACATAGGAATCAGTCCACA    SEQ ID NO:21

GGN    Target 945 (20 bp)

Target 710 (20 bp)    NGG

I2C

TCAATGTCACGTTCTCCTACCTAGTTGGTTGG    SEQ ID NO:22

AGTTACAGTGCAAGAGGATGGATCAACCAACC    SEQ ID NO:23

*ATG5* RNP          *AAVS1* RNP

D

E

A aFR-CAR lentiviral transduction

RNP electroporation

ATG5 —— E4 —— E5 —— gRNA #56    gRNA #150

Expansion of gene-edited CAR-T cells

B total eff. = 64.0 %

$R^2 = 0.8$

ATG5_E4

% of sequences p < 0.001 p ≥ 0.001

14.7    5.2    9.7    20.7    15.6    10.6

<---deletion    insertion--->

SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Target 719

<400> SEQUENCE: 1
gctacggaaa gtcagattac                                          20

<210> SEQ ID NO 2
<211> LENGTH: 20
<212> TYPE: DNA
<213> ORGANISM: Artificial Sequence
<220> FEATURE:
<223> OTHER INFORMATION: Target 696

<400> SEQUENCE: 2
gtaatctgac tttccgtagc                                          20

<210> SEQ ID NO 3
<211> LENGTH: 20
<212> TYPE: DNA
<213> ORGANISM: Artificial Sequence
<220> FEATURE:
<223> OTHER INFORMATION: Target 824

<400> SEQUENCE: 3

-continued

```
gcaccgagta gtaccacttg                                            20

<210> SEQ ID NO 4
<211> LENGTH: 20
<212> TYPE: DNA
<213> ORGANISM: Artificial Sequence
<220> FEATURE:
<223> OTHER INFORMATION: Target 950

<400> SEQUENCE: 4
aagttcggca atcttgttac                                            20

<210> SEQ ID NO 5
<211> LENGTH: 20
<212> TYPE: DNA
<213> ORGANISM: Artificial Sequence
<220> FEATURE:
<223> OTHER INFORMATION: Target 905

<400> SEQUENCE: 5
cggatcgctg cctaatgtta                                            20

<210> SEQ ID NO 6
<211> LENGTH: 20
<212> TYPE: DNA
<213> ORGANISM: Artificial Sequence
<220> FEATURE:
<223> OTHER INFORMATION: Target 945

<400> SEQUENCE: 6
ccgtttatgt atccttagtc                                            20

<210> SEQ ID NO 7
<211> LENGTH: 20
<212> TYPE: DNA
<213> ORGANISM: Artificial Sequence
<220> FEATURE:
<223> OTHER INFORMATION: Target 710

<400> SEQUENCE: 7
gtcacgttct cctacctagt                                            20

<210> SEQ ID NO 8
<211> LENGTH: 10041
<212> TYPE: DNA
<213> ORGANISM: Artificial Sequence
<220> FEATURE:
<223> OTHER INFORMATION: pAAV_ATG5_C4-CD27CD3z-CAR.xdna

<400> SEQUENCE: 8
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct gcggcctaag cttgagcgga gttccaattg tactgtacag cacatagact   180
tgcaggtgtg agttaatgga ttatgtattt tacaaacact tttcaaatgt cttctgattt   240
tggtgtgctt tgtttccctt ttctaagtgc atgtataatc ccagtttatg cctctgtcag   300
agatgacatc ctgcctgttc actgaatagc ccataatagg caaagatatt ctcaattgtc   360
gttactgttt tttctttttg tgtctcaggt atgcattcta gtgtttacct ggagatgatg   420
tggaaaagta gaagtgtatt tgtgatgagg aaatgcttct tctgtttcac tttaatgaag   480
tctgcccttt gctttccccc tcatctctct gagaggcagt gctgctcctc agcctgctcc   540
agctacggaa agtcagatta ctggaggaag ctacttatta aggagcccat tcgctcactt   600
```

```
tttgggtata ggactgtttt tttgtttttg ttttcctctg tgcatcctca gcatctggca      660
caggctcctc aaaagcttct gacctcttct cttcctccca cagggcctcg agagatctgg      720
cggcggagag ggcagaggaa gtcttctaac atgcggtgac gtggaggaga atcccggccc      780
tatggcctta ccagtgaccg ccttgctcct gccgctggcc ttgctgctcc acgccgccag      840
gccgggatcc cagctggtgg agtctggggg aggcttggta cagccagggc ggtccctgag      900
actctcctgc acaacttctg gattcacttt tggtgattat gctatgatct gggcccgcca      960
ggctccaggg aaggggctgg agtgggtctc atccattagt agtagtagta gttacatata     1020
ctacgcagac tcagtgaagg gccgattcac catctccaga gacaacgcca agaactcact     1080
gtatctgcaa atgaacagcc tgagagccga ggacacggct gtgtattact gtgcgagaga     1140
acgatacgat ttttggagtg gaatggacgt ctggggcaaa gggaccacgg tcaccgtctc     1200
gagtggtgga ggcggttcag gcggaggtgg ctctggcggt agtgcacagt ctgccctgac     1260
tcagcctgcc tccgtgtctg ggtctcctgg acagtcgatc accatctcct gcactggaac     1320
cagcagtgat gttgggagtt ataaccttgt ctcctggtac caacagcacc caggcaaagc     1380
ccccaaactc atgatttatg agggcagtaa gcggccctca ggggtttcta atcgcttctc     1440
tggctccaag tctggcaacg cggcctccct gacaatctct gggctccagg ctgaggacga     1500
ggctgattat tactgccagt cctatgacag cagcctgagt gtggtattcg gcggagggac     1560
caagctgacc gtcctaggtg ctagcaccac gacgccagcg ccgcgaccac caacaccggc     1620
gcccaccatc gcgtcgcagc ccctgtccct gcgcccagag gcgtgccggc cagcggcggg     1680
gggcgcagtg cacacgaggg ggctggactt cgcctgtgat atctacatct gggcgccctt     1740
ggccgggact tgtgggggtcc ttctcctgtc actggttatc accctttact gccaacgaag     1800
gaaatataga tcaaacaaag gagaaagtcc tgtggagcct gcagagcctt gtcgttacag     1860 ctgcccagg gaggaggagg gcagcaccat ccccatccag gaggattacc gaaaaccgga     1920
gcctgcctgc tcccccagag tgaagttcag caggagcgca gacgcccccg cgtaccagca     1980
gggccagaac cagctctata acgagctcaa tctaggacga agagaggagt acgatgtttt     2040
ggacaagaga cgtggccggg accctgagat ggggggaaag ccgagaagga agaaccctca     2100
ggaaggcctg tacaatgaac tgcagaaaga taagatggcg gaggcctaca gtgagattgg     2160
gatgaaaggc gagcgccgga ggggcaaggg gcacgatggc ctttaccagg gtctcagtac     2220
agccaccaag gacacctacg acgcccttca catgcaggcc ctgccccctc gctgataagc     2280
ggccgcctgt gccttctagt tgccagccat ctgttgtttg cccctccccc gtgccttcct     2340
tgaccctgga aggtgccact cccactgtcc tttcctaata aaatgaggaa attgcatcgc     2400
attgtctgag taggtgtcat tctattctgg ggggtggggt ggggcaggac agcaaggggg     2460
aggattggga agacaatagc aggcatgctg gggatgcggt gggctctatg ggtcgacgtg     2520
gtactactcg gtgcatgaat gtttccccag gctcatgttg ggattttgtt tgaaatcatc     2580
tttatgggtt ttcttactag aaatgatagt tttagagaag ttcggcaatc ttgttactgg     2640
tactcaagct tatatacacg tgagtaatct taactttgga aatatcaacc gttttctgtc     2700
tagaaaaaca tccacagtta aaaaccaagt atggtcatag ttttattttt agaagaattt     2760
catttgttag aggtattttt tctgttcttg ttctgtaata taggttagga taccattttt     2820
tttttccaaa caagttttg ctgttttaat tacaactttt aaccttcatt ggctttgtaa     2880
tagtatataa gagtatgtga gagtataaga gtatatttgg ccaaattgac aacaactggg     2940
```

-continued

```
taccctcgag cgcaggaacc cctagtgatg gagttggcca ctccctctct gcgcgctcgc   3000
tcgctcactg aggccgcccg ggctttgccc gggcggcctc agtgagcgag cgagcgcgca   3060
gctgcctgca ggggcagctt gaaggaaata ctaaggcaaa ggtactgcaa gtgctcgcaa   3120
cattcgctta tgcggattat tgccgtagtg ccgcgacgcc gggggcaaga tgcagagatt   3180
gccatggtac aggccgtgcg gttgatattg ccaaaacaga gctgtggggg agagttgtcg   3240
agaaagagtg cggaagatgc aaaggcgtcg gctattcaag gatgccagca agcgcagcat   3300
atcgcgctgt gacgatgcta atcccaaacc ttacccaacc cacctggtca cgcactgtta   3360
agccgctgta tgacgctctg gtggtgcaat gccacaaaga gagtcaatc gcagacaaca    3420 ttttgaatgc ggtcacacgt tagcagcatg attgccacgg atggcaacat attaacggca   3480
tgatattgac ttattgaata aaattgggta aatttgactc aacgatgggt taattcgctc   3540
gttgtggtag tgagatgaaa agaggcggcg cttactaccg attccgccta gttggtcact   3600
tcgacgtatc gtctggaact ccaaccatcg caggcagaga ggtctgcaaa atgcaatccc   3660
gaaacagttc gcaggtaata gttagagcct gcataacggt ttcgggattt tttatatctg   3720
cacaacaggt aagagcattg agtcgataat cgtgaagagt cggcgagcct ggttagccag   3780
tgctctttcc gttgtgctga attaagcgaa taccggaagc agaaccggat caccaaatgc   3840
gtacaggcgt catcgccgcc cagcaacagc acaacccaaa ctgagccgta gccactgtct   3900
gtcctgaatt cattagtaat agttacgctg cggccttta cacatgacct tcgtgaaagc    3960
gggtggcagg aggtcgcgct aacaacctcc tgccgttttg cccgtgcata tcggtcacga   4020
acaaatctga ttactaaaca cagtagcctg gatttgttct atcagtaatc gaccttattc   4080
ctaattaaat agagcaaatc cccttattgg gggtaagaca tgaagatgcc agaaaaacat   4140
gacctgttgg ccgccattct cgcggcaaag gaacaaggca tcggggcaat ccttgcgttt   4200
gcaatggcgt accttcgcgg cagatataat ggcggtgcgt ttacaaaaac agtaatcgac   4260
gcaacgatgt gcgccattat cgcctggttc attcgtgacc ttctcgactt cgccggacta   4320
agtagcaatc tcgcttatat aacgagcgtg tttatcggct acatcggtac tgactcgatt   4380
ggttcgctta tcaaacgctt cgctgctaaa aaagccggag tagaagatgg tagaaatcaa   4440
taatcaacgt aaggcgttcc tcgatatgct ggcgtggtcg gagggaactg ataacggacg   4500
tcagaaaacc agaaatcatg gttatgacgt cattgtaggc ggagagctat ttactgatta   4560
ctccgatcac cctcgcaaac ttgtcacgct aaacccaaaa ctcaaatcaa caggcgccgg   4620
acgctaccag cttcttttcc gttggtggga tgcctaccgc aagcagcttg cctgaaaga    4680 cttctctccg aaaagtcagg acgctgtggc attgcagcag attaaggagc gtggcgcttt   4740
acctatgatt gatcgtggtg atatccgtca ggcaatcgac cgttgcagca atatctgggc   4800
ttcactgccg ggcgctggtt atggtcagtt cgagcataag gctgacagcc tgattgcaaa   4860
attcaaagaa gcgggcggaa cggtcagaga gattgatgta tgagcagagt caccgcgatt   4920
atctccgctc tggttatctg catcatcgtc tgcctgtcat gggctgttaa tcattaccgt   4980
gataacgcca ttacctacaa agcccagcgc gacaaaaatg ccagagaact gaagctggcg   5040
aacgcggcaa ttactgacat gcagatgcgt cagcgtgatt ttgctgcgct cgatgcaaaa   5100
tacacgaagg agttagctga tgctaaagct gaaaatgatg ctctgcgtga tgatgttgcc   5160
gctggtcgtc gtcggttgca catcaaagca gtctgtcagt cagtgcgtga agccaccacc   5220 gcctccggc tggataatgc agcctccccc cgactggcag acaccgctga acgggattat    5280
ttcaccctca gagagaggct gatcactatg caaaaacaac tggaaggaac ccagaagtat   5340
```

```
attaatgagc agtgcagata gagttgccca tatcgatggg caactcatgc aattattgtg    5400
agcaatacac acgcgcttcc agcggagtat aaatgcctaa agtaataaaa ccgagcaatc    5460
catttacgaa tgtttgctgg gtttctgttt taacaacatt ttctgcgccg ccacaaattt    5520
tggctgcatc gacagttttc ttctgcccaa ttccagaaac gaagaaatga tgggtgatgg    5580
tttcctttgg tgctactgct gccggtttgt tttgaacagt aaacgtctgt tgagcacatc    5640
ctgtaataag cagggccagc gcagtagcga gtagcatttt tttcatggtg ttattcccga    5700 tgcttttga agttcgcaga atcgtatgtg tagaaaatta aacaaaccct aaacaatgag    5760
ttgaaatttc atattgttaa tatttattaa tgtatgtcag gtgcgatgaa tcgtcattgt    5820
attcccggat taactatgtc cacagccctg acggggaact tctctgcggg agtgtccggg    5880
aataattaaa acgatgcaca cagggtttag cgcgtacacg tattgcatta tgccaacgcc    5940
ccggtgctga cacggaagaa accggacgtt atgatttagc gtggaaagat ttgtgtagtg    6000
ttctgaatgc tctcagtaaa tagtaatgaa ttatcaaagg tatagtaata tcttttatgt    6060
tcatggatat ttgtaaccca tcggaaaact cctgctttag caagattttc cctgtattgc    6120
tgaaatgtga tttctcttga tttcaaccta tcataggacg tttctataag atgcgtgttt    6180
cttgagaatt taacatttac aacctttta agtcctttta ttaacacggt gttatcgttt    6240
tctaacacga tgtgaatatt atctgtggct agatagtaaa tataatgtga gacgttgtga    6300
cgttttagtt cagaataaaa caattcacag tctaaatctt ttcgcacttg atcgaatatt    6360
tctttaaaaa tggcaacctg agccattggt aaaaccttcc atgtgatacg agggcgcgta    6420
gtttgcatta tcgttttat cgtttcaatc tggtctgacc tccttgtgtt ttgttgatga    6480
tttatgtcaa atattaggaa tgttttcact taatagtatt ggttgcgtaa caaagtgcgg    6540
tcctgctggc attctggagg gaaatacaac cgacagatgt atgtaaggcc aacgtgctca    6600
aatcttcata cagaaagatt tgaagtaata ttttaaccgc tagatgaaga gcaagcgcat    6660
ggagcgacaa aatgaataaa gaacaatctg ctgatgatcc ctccgtggat ctgattcgtg    6720
taaaaaatat gcttaatagc accatttcta tgagttaccc tgatgttgta attgcatgta    6780
tagaacataa ggtgtctctg gaagcattca gagcaattga ggcagcgttg gtgaagcacg    6840
ataataatat gaaggattat tccctggtgg ttgactgatc accataactg ctaatcattc    6900
aaactattta gtctgtgaca gagccaacac gcagtctgtc actgtcagga aagtggtaaa    6960
actgcaactc aattactgca atgccctcgt aattaagtga atttacaata tcgtcctgtt    7020
cggagggaag aacgcgggat gttcattctt catcactttt aattgatgta tatgctctct    7080
tttctgacgt tagtctccga cggcaggctt caatgaccca ggctgagaaa ttcccggacc    7140 cttttgctc aagagcgatg ttaatttgtt caatcatttg gttaggaaag cggatgttgc    7200
gggttgttgt tctgcgggtt ctgttcttcg ttgacatgag gttgccccgt attcagtgtc    7260
gctgatttgt attgtctgaa gttgttttta cgttaagttg atgcagatca attaatacga    7320
tacctgcgtc ataattgatt atttgacgtg gtttgatggc ctccacgcac gttgtgatat    7380
gtagatgata atcattatca ctttacgggt cctttccggt gatccgacag gttacggcct    7440
gatgcggtat tttctcctta cgcatctgtg cggtatttca caccgcatac gtcaaagcaa    7500
ccatagtacg cgccctgtag cggcgcatta agcgcggcgg gtgtggtggt tacgcgcagc    7560
gtgaccgcta cacttgccag cgccctagcg cccgctcctt tcgctttctt cccttccttt    7620
ctcgccacgt tcgccggctt tccccgtcaa gctctaaatc gggggctccc tttagggttc    7680
```

-continued

```
cgatttagtg ctttacggca cctcgacccc aaaaaacttg atttgggtga tggttcacgt   7740
agtgggccat cgccctgata gacggttttt cgcccttga cgttggagtc cacgttcttt   7800
aatagtggac tcttgttcca aactggaaca acactcaacc ctatctcggg ctattctttt   7860
gatttataag ggattttgcc gatttcggcc tattggttaa aaaatgagct gatttaacaa   7920
aaatttaacg cgaattttaa caaaatatta acgtttacaa ttttatggtg cactctcagt   7980
acaatctgct ctgatgccgc atagttaagc cagccccgac acccgccaac acccgctgac   8040
gcgccctgac gggcttgtct gctcccggca tccgcttaca gacaagctgt gaccgtctcc   8100
gggagctgca tgtgtcagag gttttcaccg tcatcaccga aacgcgcgag acgaaagggc   8160
ctcgtgatac gcctattttt ataggttaat gtcatgataa taatggtttc ttagacgtca   8220
ggtggcactt ttcggggaaa tgtgcgcgga accctatt gtttattttt ctaaatacat   8280
tcaaatatgt atccgctcat gagacaataa ccctgataaa tgcttcaata atattgaaaa   8340
aggaagagta tgagtattca acatttccgt gtcgccctta ttcccttttt tgcggcattt   8400
tgccttcctg ttttttgctca cccagaaacg ctggtgaaag taaaagatgc tgaagatcag   8460
ttgggtgcac gagtgggtta catcgaactg gatctcaaca gcggtaagat ccttgagagt   8520
tttcgccccg aagaacgttt tccaatgatg agcacttta aagttctgct atgtggcgcg   8580
gtattatccc gtattgacgc cgggcaagag caactcggtc gccgcataca ctattctcag   8640
aatgacttgg ttgagtactc accagtcaca gaaaagcatc ttacgcatgg catgacagta   8700
agagaattat gcagtgctgc cataaccatg agtgataaca ctgcggccaa cttacttctg   8760
acaacgatcg gaggaccgaa ggagctaacc gcttttttgc acaacatggg ggatcatgta   8820
actcgccttg atcgttggga accggagctg aatgaagcca taccaaacga cgagcgtgac   8880
accacgatgc ctgtagcaat ggcaacaacg ttgcgcaaac tattaactgg cgaactactt   8940
actctagctt cccggcaaca attaatagac tggatggagg cggataaagt tgcaggacca   9000
cttctgcgct cggcccttcc ggctggctgg tttattgctg ataaatctgg agccggtgag   9060
cgtgggtctc gcggtatcat tgcagcactg gggccagatg gtaagccctc ccgtatcgta   9120
gttatctaca cgacggggag tcaggcaact atggatgaac gaaatagaca gatcgctgag   9180
ataggtgcct cactgattaa gcattggtaa ctgtcagacc aagtttactc atatatactt   9240
tagattgatt taaaacttca ttttaattt aaaaggatct aggtgaagat cctttttgat   9300
aatctcatga ccaaaatccc ttaacgtgag ttttcgttcc actgagcgtc agaccccgta   9360
gaaaagatca aaggatcttc ttgagatcct tttttctgc gcgtaatctg ctgcttgcaa   9420
acaaaaaaac caccgctacc agcggtggtt tgtttgccgg atcaagagct accaactctt   9480
tttccgaagg taactggctt cagcagagcg cagataccaa atactgtcct tctagtgtag   9540
ccgtagttag gccaccactt caagaactct gtagcaccgc ctacatacct cgctctgcta   9600
atcctgttac cagtggctgc tgccagtggc gataagtcgt gtcttaccgg gttggactca   9660
agacgatagt taccggataa ggcgcagcgg tcgggctgaa cggggggttc gtgcacacag   9720
cccagcttgg agcgaacgac ctacaccgaa ctgagatacc tacagcgtga gctatgagaa   9780
agcgccacgc ttcccgaagg gagaaaggcg gacaggtatc cggtaagcgg cagggtcgga   9840
acaggagagc gcacgaggga gcttccaggg ggaaacgcct ggtatcttta tagtcctgtc   9900
gggtttcgcc acctctgact tgagcgtcga ttttttgtgat gctcgtcagg ggggcggagc   9960
ctatggaaaa acgccagcaa cgcggccttt ttacggttcc tggccttttg ctggcctttt  10020
gctcacatgt cctgcaggca g                                            10041
```

-continued

```
<210> SEQ ID NO 9
<211> LENGTH: 10035
<212> TYPE: DNA
<213> ORGANISM: Artificial Sequence
<220> FEATURE:
<223> OTHER INFORMATION: pAAV_ATG5_C4-CD28CD3z-CAR.xdna

<400> SEQUENCE: 9
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct gcggcctaag cttgagcgga gttccaattg tactgtacag cacatagact     180
tgcaggtgtg agttaatgga ttatgtattt tacaaacact tttcaaatgt cttctgattt     240
tggtgtgctt tgtttccctt ttctaagtgc atgtataatc ccagtttatg cctctgtcag     300
agatgacatc ctgcctgttc actgaatagc ccataatagg caaagatatt ctcaattgtc     360
gttactgttt tttcttttttg tgtctcaggt atgcattcta gtgtttacct ggagatgatg     420
tggaaaagta gaagtgtatt tgtgatgagg aaatgcttct tctgtttcac tttaatgaag     480
tctgcccttt gctttccccc tcatctctct gagaggcagt gctgctcctc agcctgctcc     540
agctacggaa agtcagatta ctggaggaag ctacttatta aggagcccat tcgctcactt     600
tttgggtata ggactgtttt tttgtttttg ttttcctctg tgcatcctca gcatctggca     660
caggctcctc aaaagcttct gacctcttct cttcctccca cagggcctcg agagatctgg     720
cggcggagag ggcagaggaa gtcttctaac atgcggtgac gtggaggaga tccccggccc     780
tatggcctta ccagtgaccg ccttgctcct gccgctggcc ttgctgctcc acgccgccag     840
gccgggatcc cagctggtgg agtctggggg aggcttggta cagccagggc ggtccctgag     900
actctcctgc acaacttctg gattcacttt tggtgattat gctatgatct gggcccgcca     960
ggctccaggg aaggggctgg agtgggtctc atccattagt agtagtagta gttacatata    1020
ctacgcagac tcagtgaagg gccgattcac catctccaga gacaacgcca agaactcact    1080
gtatctgcaa atgaacagcc tgagagccga ggacacggct gtgtattact gtgcgagaga    1140
acgatacgat ttttggagtg gaatggacgt ctggggcaaa gggaccacgg tcaccgtctc    1200
gagtggtgga ggcggttcag cggaggtgg ctctggcggt agtgcacagt ctgccctgac    1260
tcagcctgcc tccgtgtctg ggtctcctgg acagtcgatc accatctcct gcactggaac    1320
cagcagtgat gttgggagtt ataaccttgt ctcctggtac caacagcacc caggcaaagc    1380
ccccaaactc atgatttatg agggcagtaa gcggccctca ggggtttcta atcgcttctc    1440
tggctccaag tctggcaacg cggcctccct gacaatctct gggctccagg ctgaggacga    1500
ggctgattat tactgccagt cctatgacag cagcctgagt gtggtattcg gcggagggac    1560
caagctgacc gtcctaggtg ctagcaccac gacgccagcg ccgcgaccac caacaccggc    1620
gcccaccatc gcgtcgcagc ccctgtccct gcgcccagag gcgtgccggc cagcggcggg    1680
gggcgcagtg cacacgaggg gctggactt cgcctgtgat ttttgggtgc tggtggtggt    1740
tggtggagtc ctggcttgct atagcttgct agtaacagtg gcctttatta ttttctgggt    1800
gaggagtaag aggagcaggc tcctgcacag tgactacatg aacatgactc cccgccgccc    1860
cgggcccacc cgcaagcatt accagcccta tgccccacca cgcgacttcg cagcctatcg    1920
ctccatcgat agagtgaagt tcagcaggag cgcagacgcc cccgcgtacc agcagggcca    1980
gaaccagctc tataacgagc tcaatctagg acgaagagag gagtacgatg ttttggacaa    2040
```

-continued

```
gagacgtggc cgggaccctg agatgggggg aaagccgaga aggaagaacc ctcaggaagg      2100
cctgtacaat gaactgcaga aagataagat ggcggaggcc tacagtgaga ttgggatgaa      2160
aggcgagcgc cggagggggca aggggcacga tggcctttac cagggtctca gtacagccac     2220
caaggacacc tacgacgccc ttcacatgca ggccctgccc cctcgctgat aagcggccgc      2280
ctgtgccttc tagttgccag ccatctgttg tttgcccctc ccccgtgcct tccttgaccc      2340
tggaaggtgc cactcccact gtcctttcct aataaaatga ggaaattgca tcgcattgtc      2400
tgagtaggtg tcattctatt ctggggggtg gggtggggca ggacagcaag ggggaggatt      2460
gggaagacaa tagcaggcat gctggggatg cggtgggctc tatgggtcga cgtggtacta      2520
ctcggtgcat gaatgtttcc ccaggctcat gttgggattt tgtttgaaat catctttatg      2580
ggttttctta ctagaaatga tagttttaga gaagttcggc aatcttgtta ctggtactca      2640
agcttatata cacgtgagta atcttaactt tggaaatatc aaccgttttc tgtctagaaa      2700
aacatccaca gttaaaaacc aagtatggtc atagtttttat ttttagaaga atttcatttg     2760
ttagaggtat tttttctgtt cttgttctgt aatataggtt aggataccat tttttttttc      2820
caaacaagtt tttgctgttt taattacaac ttttaacctt cattggcttt gtaatagtat      2880
ataagagtat gtgagagtat aagagtatat ttggccaaat tgacaacaac tgggtaccct      2940
cgagcgcagg aacccctagt gatggagttg gccactccct ctctgcgcgc tcgctcgctc      3000
actgaggccg cccgggcttt gcccgggcgg cctcagtgag cgagcgagcg cgcagctgcc      3060 tgcagggggca gcttgaagga aatactaagg caaaggtact gcaagtgctc gcaacattcg      3120
cttatgcgga ttattgccgt agtgccgcga cgccgggggc aagatgcaga gattgccatg      3180
gtacaggccg tgcggttgat attgccaaaa cagagctgtg ggggagagtt gtcgagaaag      3240
agtgcggaag atgcaaaggc gtcggctatt caaggatgcc agcaagcgca gcatatcgcg      3300
ctgtgacgat gctaatccca aaccttaccc aacccacctg gtcacgcact gttaagccgc      3360
tgtatgacgc tctggtggtg caatgccaca aagaagagtc aatcgcagac aacatttttga     3420 atgcggtcac acgttagcag catgattgcc acggatggca acatattaac ggcatgatat      3480
tgacttattg aataaaattg ggtaaatttg actcaacgat gggttaattc gctcgttgtg      3540
gtagtgagat gaaaagaggc ggcgcttact accgattccg cctagttggt cacttcgacg      3600
tatcgtctgg aactccaacc atcgcaggca gagaggtctg caaaatgcaa tcccgaaaca      3660
gttcgcaggt aatagttaga gcctgcataa cggtttcggg attttttata tctgcacaac      3720
aggtaagagc attgagtcga taatcgtgaa gagtcggcga gcctggttag ccagtgctct      3780
ttccgttgtg ctgaattaag cgaataccgg aagcagaacc ggatcaccaa atgcgtacag      3840
gcgtcatcgc cgcccagcaa cagcacaacc caaactgagc cgtagccact gtctgtcctg      3900
aattcattag taatagttac gctgcggcct tttacacatg accttcgtga aagcgggtgg      3960
caggaggtcg cgctaacaac ctcctgccgt tttgcccgtg catatcggtc acgaacaaat      4020
ctgattacta aacacagtag cctggatttg ttctatcagt aatcgacctt attcctaatt      4080
aaatagagca aatccccctta ttgggggggtaa gacatgaaga tgccagaaaa acatgacctg      4140
ttggccgcca ttctcgcggc aaaggaacaa ggcatcgggg caatccttgc gtttgcaatg      4200
gcgtaccttc gcggcagata taatggcggt gcgtttacaa aaacagtaat cgacgcaacg      4260
atgtgcgcca ttatcgcctg gttcattcgt gaccttctcg acttcgccgg actaagtagc      4320
aatctcgctt ataatacgag cgtgtttatc ggctacatcg gtactgactc gattggttcg      4380
cttatcaaac gcttcgctgc taaaaaagcc ggagtagaag atggtagaaa tcaataatca      4440
```

```
acgtaaggcg ttcctcgata tgctggcgtg gtcggaggga actgataacg gacgtcagaa    4500
aaccagaaat catggttatg acgtcattgt aggcggagag ctatttactg attactccga    4560
tcaccctcgc aaacttgtca cgctaaaccc aaaactcaaa tcaacaggcg ccggacgcta    4620
ccagcttctt tcccgttggt gggatgccta ccgcaagcag cttggcctga aagacttctc    4680
tccgaaaagt caggacgctg tggcattgca gcagattaag gagcgtggcg ctttacctat    4740
gattgatcgt ggtgatatcc gtcaggcaat cgaccgttgc agcaatatct gggcttcact    4800
gccgggcgct ggttatggtc agttcgagca taaggctgac agcctgattg caaaattcaa    4860
agaagcgggc ggaacggtca gagagattga tgtatgagca gagtcaccgc gattatctcc    4920
gctctggtta tctgcatcat cgtctgcctg tcatgggctg ttaatcatta ccgtgataac    4980
gccattacct acaaagccca gcgcgacaaa aatgccagag aactgaagct ggcgaacgcg    5040
gcaattactg acatgcagat gcgtcagcgt gatgttgctg cgctcgatgc aaaatacacg    5100
aaggagttag ctgatgctaa agctgaaaat gatgctctgc gtgatgatgt tgccgctggt    5160
cgtcgtcggt tgcacatcaa agcagtctgt cagtcagtgc gtgaagccac caccgcctcc    5220
ggcgtggata atgcagcctc cccccgactg gcagacaccg ctgaacggga ttatttcacc    5280
ctcagagaga ggctgatcac tatgcaaaaa caactggaag gaacccagaa gtatattaat    5340
gagcagtgca gatagagttg cccatatcga tgggcaactc atgcaattat tgtgagcaat    5400
acacacgcgc ttccagcgga gtataaatgc ctaaagtaat aaaaccgagc aatccattta    5460
cgaatgtttg ctgggtttct gttttaacaa cattttctgc gccgccacaa attttggctg    5520
catcgacagt tttcttctgc ccaattccag aaacgaagaa atgatgggtg atggtttcct    5580
ttggtgctac tgctgccggt ttgtttttgaa cagtaaacgt ctgttgagca catcctgtaa    5640
taagcagggc cagcgcagta gcgagtagca ttttttttcat ggtgttattc ccgatgcttt    5700
ttgaagttcg cagaatcgta tgtgtagaaa attaaacaaa ccctaaacaa tgagttgaaa    5760
tttcatattg ttaatattta ttaatgtatg tcaggtgcga tgaatcgtca ttgtattccc    5820
ggattaacta tgtccacagc cctgacgggg aacttctctg cgggagtgtc cgggaataat    5880
taaaacgatg cacacagggt ttagcgcgta cacgtattgc attatgccaa cgccccggtg    5940
ctgacacgga agaaccgga cgttatgatt tagcgtggaa agatttgtgt agtgttctga    6000
atgctctcag taaatagtaa tgaattatca aaggtatagt aatatctttt atgttcatgg    6060
atatttgtaa cccatcggaa aactcctgct ttagcaagat tttccctgta ttgctgaaat    6120
gtgatttctc ttgatttcaa cctatcatag gacgtttcta taagatgcgt gtttcttgag    6180
aatttaacat ttacaacctt tttaagtcct tttattaaca cggtgttatc gttttctaac    6240
acgatgtgaa tattatctgt ggctagatag taaatataat gtgagacgtt gtgacgtttt    6300
agttcagaat aaaacaattc acagtctaaa tcttttcgca cttgatcgaa tatttcttta    6360
aaaatggcaa cctgagccat tggtaaaacc ttccatgtga tacgagggcg cgtagtttgc    6420
attatcgttt ttatcgtttc aatctggtct gacctccttg tgttttgttg atgatttatg    6480
tcaaatatta ggaatgtttt cacttaatag tattggttgc gtaacaaagt gcggtcctgc    6540
tggcattctg gagggaaata caaccgacag atgtatgtaa ggccaacgtg ctcaaatctt    6600
catacagaaa gatttgaagt aatatttttaa ccgctagatg aagagcaagc gcatggagcg    6660
acaaaatgaa taaagaacaa tctgctgatg atccctccgt ggatctgatt cgtgtaaaaa    6720
atatgcttaa tagcaccatt tctatgagtt accctgatgt tgtaattgca tgtatagaac    6780
```

-continued

```
ataaggtgtc tctggaagca ttcagagcaa ttgaggcagc gttggtgaag cacgataata    6840
atatgaagga ttattccctg gtggttgact gatcaccata actgctaatc attcaaacta    6900
tttagtctgt gacagagcca acacgcagtc tgtcactgtc aggaaagtgg taaaactgca    6960
actcaattac tgcaatgccc tcgtaattaa gtgaatttac aatatcgtcc tgttcggagg    7020
gaagaacgcg ggatgttcat tcttcatcac ttttaattga tgtatatgct ctcttttctg    7080
acgttagtct ccgacggcag gcttcaatga cccaggctga gaaattcccg gacccttttt    7140
gctcaagagc gatgttaatt tgttcaatca tttggttagg aaagcggatg ttgcgggttg    7200
ttgttctgcg ggttctgttc ttcgttgaca tgaggttgcc ccgtattcag tgtcgctgat    7260
ttgtattgtc tgaagttgtt tttacgttaa gttgatgcag atcaattaat acgatacctg    7320
cgtcataatt gattatttga cgtggtttga tggcctccac gcacgttgtg atatgtagat    7380
gataatcatt atcactttac gggtcctttc cggtgatccg acaggttacg gcctgatgcg    7440
gtattttctc cttacgcatc tgtgcggtat ttcacaccgc atacgtcaaa gcaaccatag    7500
tacgcgccct gtagcggcgc attaagcgcg gcgggtgtgg tggttacgcg cagcgtgacc    7560
gctacacttg ccagcgccct agcgcccgct cctttcgctt tcttcccttc ctttctcgcc    7620
acgttcgccg gctttccccg tcaagctcta aatcgggggc tccctttagg gttccgattt    7680
agtgctttac ggcacctcga ccccaaaaaa cttgatttgg gtgatggttc acgtagtggg    7740
ccatcgccct gatagacggt ttttcgccct ttgacgttgg agtccacgtt ctttaatagt    7800
ggactcttgt tccaaactgg aacaacactc aaccctatct cgggctattc ttttgattta    7860
taagggattt tgccgatttc ggcctattgg ttaaaaaatg agctgattta acaaaaattt    7920
aacgcgaatt ttaacaaaat attaacgttt acaattttat ggtgcactct cagtacaatc    7980
tgctctgatg ccgcatagtt aagccagccc cgacacccgc caacaccogc tgacgcgccc    8040 tgacgggctt gtctgctccc ggcatccgct tacagacaag ctgtgaccgt ctccgggagc    8100
tgcatgtgtc agaggttttc accgtcatca ccgaaacgcg cgagacgaaa gggcctcgtg    8160
atacgcctat ttttataggt taatgtcatg ataataatgg tttcttagac gtcaggtggc    8220
acttttcggg gaaatgtgcg cggaacccct atttgtttat ttttctaaat acattcaaat    8280
atgtatccgc tcatgagaca ataaccctga taaatgcttc aataatattg aaaaaggaag    8340
agtatgagta ttcaacattt ccgtgtcgcc cttattccct tttttgcggc attttgcctt    8400
cctgtttttg ctcacccaga aacgctggtg aaagtaaaag atgctgaaga tcagttgggt    8460
gcacgagtgg gttacatcga actggatctc aacagcggta agatccttga gagttttcgc    8520
cccgaagaac gttttccaat gatgagcact tttaaagttc tgctatgtgg cgcggtatta    8580
tcccgtattg acgccgggca agagcaactc ggtcgccgca tacactattc tcagaatgac    8640
ttggttgagt actcaccagt cacagaaaag catcttacgg atggcatgac agtaagagaa    8700
ttatgcagtg ctgccataac catgagtgat aacactgcgg ccaacttact tctgacaacg    8760
atcggaggac cgaaggagct aaccgctttt ttgcacaaca tgggggatca tgtaactcgc    8820
cttgatcgtt gggaaccgga gctgaatgaa gccataccaa acgacgagcg tgacaccacg    8880
atgcctgtag caatggcaac aacgttgcgc aaactattaa ctggcgaact acttactcta    8940
gcttcccggc aacaattaat agactggatg gaggcggata aagttgcagg accacttctg    9000
cgctcggccc ttccggctgg ctggtttatt gctgataaat ctggagccgg tgagcgtggg    9060
tctcgcggta tcattgcagc actggggcca gatggtaagc cctcccgtat cgtagttatc    9120
tacacgacgg ggagtcaggc aactatggat gaacgaaata gacagatcgc tgagataggt    9180
```

-continued

```
gcctcactga ttaagcattg gtaactgtca gaccaagttt actcatatat actttagatt   9240
gatttaaaac ttcattttta atttaaaagg atctaggtga agatcctttt tgataatctc   9300
atgaccaaaa tcccttaacg tgagttttcg ttccactgag cgtcagaccc cgtagaaaag   9360
atcaaaggat cttcttgaga tccttttttt ctgcgcgtaa tctgctgctt gcaaacaaaa   9420
aaaccaccgc taccagcggt ggtttgtttg ccggatcaag agctaccaac tctttttccg   9480
aaggtaactg gcttcagcag agcgcagata ccaaatactg tccttctagt gtagccgtag   9540
ttaggccacc acttcaagaa ctctgtagca ccgcctacat acctcgctct gctaatcctg   9600
ttaccagtgg ctgctgccag tggcgataag tcgtgtctta ccgggttgga ctcaagacga   9660
tagttaccgg ataaggcgca gcggtcgggc tgaacggggg gttcgtgcac acagcccagc   9720
ttggagcgaa cgacctacac cgaactgaga tacctacagc gtgagctatg agaaagcgcc   9780
acgcttcccg aagggagaaa ggcggacagg tatccggtaa gcggcagggt cggaacagga   9840
gagcgcacga gggagcttcc agggggaaac gcctggtatc tttatagtcc tgtcgggttt   9900
cgccacctct gacttgagcg tcgatttttg tgatgctcgt caggggggcg agcctatgg   9960 aaaaacgcca gcaacgcggc cttttttacgg ttcctggcct tttgctggcc ttttgctcac  10020
atgtcctgca ggcag                                                    10035
```

```
<210> SEQ ID NO 10
<211> LENGTH: 10782
<212> TYPE: DNA
<213> ORGANISM: Artificial Sequence
<220> FEATURE:
<223> OTHER INFORMATION: pAAV_AAVS1_C4-CD27CD3z-CAR.xdna

<400> SEQUENCE: 10
```

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct gcggcctaag cttgagcgga gttccaattg tactgtacag ccctttgctt    180
tctctgacca gcattctctc ccctgggcct gtgccgcttt ctgtctgcag cttgtggcct    240
gggtcacctc tacggctggc ccagatcctt ccctgccgcc tccttcaggt tccgtcttcc    300
tccactccct cttccccttg ctctctgctg tgttgctgcc caaggatgct ctttccggag    360
cacttccttc tcggcgctgc accacgtgat gtcctctgag cggatcctcc ccgtgtctgg    420
gtcctctccg ggcatctctc ctccctcacc caaccccatg ccgtcttcac tcgctgggtt    480 ccctttttcct tctccttctg gggcctgtgc catctctcgt ttcttaggat ggccttctcc    540
gacggatgtc tcccttgcgt cccgcctccc cttcttgtag gcctgcatca tcaccgtttt    600 tctgacaac cccaaagtac cccgtctccc tggctttagc cacctctcca tcctcttgct     660
ttctttgcct ggacaccccg ttctcctgtg gattcgggtc acctctcact cctttcattt    720
gggcagctcc cctaccccccc ttacctctct agtctgtgct agctcttcca gccccctgtc    780
atggcatctt ccaggggtcc gagagctcag ctagtcttct tcctccaacc cgggcccta    840 tgtccacttc aggacagcat gtttgctgcc tccagggatc ctgtgtcccc gagctgggac    900
caccttatat tcccagggcc ggttaatgtg gctctggttc tgggtacttt tatctgtccc    960 ctccaccccca cagtggggca agcttctgac ctcttctctt cctcccacag ggcctcgaga   1020
gatctggcgg cggagagggc agaggaagtc ttctaacatg cggtgacgtg gaggagaatc   1080
ccggccctat ggccttacca gtgaccgcct tgctcctgcc gctggccttg ctgctccacg   1140
```

-continued

```
ccgccaggcc gggatcccag ctggtggagt ctgggggagg cttggtacag ccagggcggt   1200
ccctgagact ctcctgcaca acttctggat tcacttttgg tgattatgct atgatctggg   1260
cccgccaggc tccagggaag gggctggagt gggtctcatc cattagtagt agtagtagtt   1320
acatatacta cgcagactca gtgaagggcc gattcaccat ctccagagac aacgccaaga   1380
actcactgta tctgcaaatg aacagcctga gagccgagga cacggctgtg tattactgtg   1440
cgagagaacg atacgatttt tggagtggaa tggacgtctg gggcaaaggg accacggtca   1500
ccgtctcgag tggtggaggc ggttcaggcg gaggtggctc tggcggtagt gcacagtctg   1560
ccctgactca gcctgcctcc gtgtctgggt ctcctggaca gtcgatcacc atctcctgca   1620
ctggaaccag cagtgatgtt gggagttata accttgtctc ctggtaccaa cagcacccag   1680
gcaaagcccc caaactcatg atttatgagg gcagtaagcg gccctcaggg gtttctaatc   1740
gcttctctgg ctccaagtct ggcaacgcgg cctccctgac aatctctggg ctccaggctg   1800
aggacgaggc tgattattac tgccagtcct atgacagcag cctgagtgtg gtattcggcg   1860
gagggaccaa gctgaccgtc ctaggtgcta gcaccacgac gccagcgccg cgaccaccaa   1920
caccggcgcc caccatcgcg tcgcagcccc tgtccctgcg cccagaggcg tgccggccag   1980
cggcgggggg cgcagtgcac acgaggggggc tggacttcgc ctgtgatatc tacatctggg   2040
cgcccttggc cgggacttgt ggggtccttc tcctgtcact ggttatcacc ctttactgcc   2100
aacgaaggaa atatagatca aacaaaggag aaagtcctgt ggagcctgca gagccttgtc   2160
gttacagctg ccccagggag gaggagggca gcaccatccc catccaggag gattaccgaa   2220
aaccggagcc tgcctgctcc cccagagtga agttcagcag gagcgcagac gcccccgcgt   2280
accagcaggg ccagaaccag ctctataacg agctcaatct aggacgaaga gaggagtacg   2340
atgttttgga caagagacgt ggccgggacc ctgagatggg gggaaagccg agaaggaaga   2400
accctcagga aggcctgtac aatgaactgc agaaagataa gatggcggag gcctacagtg   2460
agattgggat gaaaggcgag cgccggaggg gcaaggggca cgatggcctt taccagggtc   2520
tcagtacagc caccaaggac acctacgacg cccttcacat gcaggccctg cccctcgct   2580 gataagcggc cgcctgtgcc ttctagttgc cagccatctg ttgtttgccc ctcccccgtg   2640
ccttccttga ccctggaagg tgccactccc actgtccttt cctaataaaa tgaggaaatt   2700
gcatcgcatt gtctgagtag gtgtcattct attctggggg gtggggtggg gcaggacagc   2760 aaggggggagg attgggaaga caatagcagg catgctgggg atgcggtggg ctctatgggt   2820
cgacagtact aagctttact agggacagga ttggtgacag aaaagcccca tccttaggcc   2880
tcctccttcc tagtctcctg atattgggtc taacccccac ctcctgttag gcagattcct   2940
tatctggtga cacaccccca tttcctggag ccatctctct ccttgccaga acctctaagg   3000
tttgcttacg atggagccag agaggatcct gggagggaga gcttggcagg gggtgggagg   3060 gaagggggagg atgcgtgacc tgcccggttc tcagtggcca ccctgcgcta ccctctccca   3120
gaacctgagc tgctctgacg cggctgtctg gtgcgtttca ctgatcctgg tgctgcagct   3180
tccttacact tcccaagagg agaagcagtt tggaaaaaca aaatcagaat aagttggtcc   3240
tgagttctaa ctttggctct tcaccttct agtccccaat ttatattgtt cctccgtgcg   3300
tcagttttac ctgtgagata aggccagtag ccagcccgt cctggcaggg ctgtggtgag   3360
gaggggggtg tccgtgtgga aaactccctt tgtgagaatg gtgcgtccta ggtgttcacc   3420
aggtcgtggc cgcctctact ccctttctct ttctccatcc ttctttcctt aaagagtccc   3480
cagtgctatc tgggacatat tcctccgccc agagcagggt cccgcttccc taaggccctg   3540
```

-continued

```
ctctgggctt ctgggtttga gtccttggca agcccaggag aggcgctcag gcttccctgt    3600
cccccttcct cgtccaccat ctcatgcccc tggctctcct gccccttccc tacaggggtt    3660
cctggctctg ctctaagggg gtaccctcga gcgcaggaac ccctagtgat ggagttggcc    3720
actccctctc tgcgcgctcg ctcgctcact gaggccgccc gggctttgcc cgggcggcct    3780
cagtgagcga gcgagcgcgc agctgcctgc aggggcagct tgaaggaaat actaaggcaa    3840
aggtactgca agtgctcgca acattcgctt atgcggatta ttgccgtagt gccgcgacgc    3900 cggggggcaag atgcagagat tgccatggta caggccgtgc ggttgatatt gccaaaacag    3960
agctgtgggg gagagttgtc gagaaagagt gcggaagatg caaaggcgtc ggctattcaa    4020
ggatgccagc aagcgcagca tatcgcgctg tgacgatgct aatcccaaac cttacccaac    4080
ccacctggtc acgcactgtt aagccgctgt atgacgctct ggtggtgcaa tgccacaaag    4140
aagagtcaat cgcagacaac attttgaatg cggtcacacg ttagcagcat gattgccacg    4200
gatggcaaca tattaacggc atgatattga cttattgaat aaaattgggt aaatttgact    4260
caacgatggg ttaattcgct cgttgtggta gtgagatgaa aagaggcggc gcttactacc    4320
gattccgcct agttggtcac ttcgacgtat cgtctggaac tccaaccatc gcaggcagag    4380
aggtctgcaa aatgcaatcc cgaaacagtt cgcaggtaat agttagagcc tgcataacgg    4440
tttcgggatt ttttatatct gcacaacagg taagagcatt gagtcgataa tcgtgaagag    4500
tcggcgagcc tggttagcca gtgctctttc cgttgtgctg aattaagcga ataccggaag    4560
cagaaccgga tcaccaaatg cgtacaggcg tcatcgccgc ccagcaacag cacaacccaa    4620
actgagccgt agccactgtc tgtcctgaat tcattagtaa tagttacgct gcggcctttt    4680
acacatgacc ttcgtgaaag cgggtggcag gaggtcgcgc taacaacctc ctgccgtttt    4740
gcccgtgcat atcggtcacg aacaaatctg attactaaac acagtagcct ggatttgttc    4800
tatcagtaat cgaccttatt cctaattaaa tagagcaaat cccccttattg ggggtaagac    4860 atgaagatgc cagaaaaaca tgacctgttg gccgccattc tcgcggcaaa ggaacaaggc    4920
atcggggcaa tccttgcgtt tgcaatggcg taccttcgcg gcagatataa tggcggtgcg    4980
tttacaaaaa cagtaatcga cgcaacgatg tgcgccatta tcgcctggtt cattcgtgac    5040
cttctcgact tcgccggact aagtagcaat ctcgcttata taacgagcgt gtttatcggc    5100
tacatcggta ctgactcgat tggttcgctt atcaaacgct tcgctgctaa aaaagccgga    5160
gtagaagatg gtagaaatca ataatcaacg taaggcgttc ctcgatatgc tggcgtggtc    5220
ggagggaact gataacggac gtcagaaaac cagaaatcat ggttatgacg tcattgtagg    5280
cggagagcta tttactgatt actccgatca ccctcgcaaa cttgtcacgc taaacccaaa    5340
actcaaatca acaggcgccg gacgctacca gcttctttcc cgttggtggg atgcctaccg    5400
caagcagctt ggcctgaaag acttctctcc gaaaagtcag gacgctgtgg cattgcagca    5460
gattaaggag cgtggcgctt tacctatgat tgatcgtggt gatatccgtc aggcaatcga    5520
ccgttgcagc aatatctggg cttcactgcc gggcgctggt tatggtcagt cgagcataa    5580 ggctgacagc ctgattgcaa aattcaaaga agcgggcgga acggtcagag agattgatgt    5640
atgagcagag tcaccgcgat tatctccgct ctggttatct gcatcatcgt ctgcctgtca    5700
tgggctgtta atcattaccg tgataacgcc attacctaca aagcccagcg cgacaaaaat    5760
gccagagaac tgaagctggc gaacgcggca attactgaca tgcagatgcg tcagcgtgat    5820
gttgctgcgc tcgatgcaaa atacacgaag gagttagctg atgctaaagc tgaaaatgat    5880
```

```
gctctgcgtg atgatgttgc cgctggtcgt cgtcggttgc acatcaaagc agtctgtcag   5940
tcagtgcgtg aagccaccac cgcctccggc gtggataatg cagcctcccc ccgactggca   6000
gacaccgctg aacgggatta tttcaccctc agagagaggc tgatcactat gcaaaaacaa   6060
ctggaaggaa cccagaagta tattaatgag cagtgcagat agagttgccc atatcgatgg   6120
gcaactcatg caattattgt gagcaataca cacgcgcttc cagcggagta taaatgccta   6180
aagtaataaa accgagcaat ccatttacga atgtttgctg ggtttctgtt ttaacaacat   6240
tttctgcgcc gccacaaatt ttggctgcat cgacagtttt cttctgccca attccagaaa   6300
cgaagaaatg atgggtgatg gtttcctttg gtgctactgc tgccggtttg ttttgaacag   6360
taaacgtctg ttgagcacat cctgtaataa gcagggccag cgcagtagcg agtagcattt   6420
ttttcatggt gttattcccg atgctttttg aagttcgcag aatcgtatgt gtagaaaatt   6480
aaacaaaccc taaacaatga gttgaaattt catattgtta atatttatta atgtatgtca   6540
ggtgcgatga atcgtcattg tattcccgga ttaactatgt ccacagccct gacggggaac   6600
ttctctgcgg gagtgtccgg gaataattaa aacgatgcac acagggttta gcgcgtacac   6660
gtattgcatt atgccaacgc cccggtgctg acacggaaga aaccggacgt tatgatttag   6720
cgtggaaaga tttgtgtagt gttctgaatg ctctcagtaa atagtaatga attatcaaag   6780
gtatagtaat atcttttatg ttcatggata tttgtaaccc atcggaaaac tcctgcttta   6840
gcaagatttt ccctgtattg ctgaaatgtg atttctcttg atttcaacct atcataggac   6900
gtttctataa gatgcgtgtt tcttgagaat ttaacattta caaccttttt aagtcctttt   6960
attaacacgg tgttatcgtt ttctaacacg atgtgaatat tatctgtggc tagatagtaa   7020
atataatgtg agacgttgtg acgttttagt tcagaataaa acaattcaca gtctaaatct   7080
tttcgcactt gatcgaatat ttctttaaaa atggcaacct gagccattgg taaaaccttc   7140
catgtgatac gagggcgcgt agtttgcatt atcgttttta tcgtttcaat ctggtctgac   7200
ctccttgtgt tttgttgatg atttatgtca aatattagga atgttttcac ttaatagtat   7260
tggttgcgta acaaagtgcg gtcctgctgg cattctggag ggaaatacaa ccgacagatg   7320
tatgtaaggc caacgtgctc aaatcttcat acagaaagat ttgaagtaat attttaaccg   7380
ctagatgaag agcaagcgca tggagcgaca aaatgaataa agaacaatct gctgatgatc   7440
cctccgtgga tctgattcgt gtaaaaaata tgcttaatag caccatttct atgagttacc   7500
ctgatgttgt aattgcatgt atagaacata aggtgtctct ggaagcattc agagcaattg   7560
aggcagcgtt ggtgaagcac gataataata tgaaggatta ttccctggtg gttgactgat   7620
caccataact gctaatcatt caaactattt agtctgtgac agagccaaca cgcagtctgt   7680
cactgtcagg aaagtggtaa aactgcaact caattactgc aatgccctcg taattaagtg   7740
aatttacaat atcgtcctgt tcggagggaa gaacgcggga tgttcattct tcatcacttt   7800
taattgatgt atatgctctc ttttctgacg ttagtctccg acggcaggct tcaatgaccc   7860
aggctgagaa attcccggac cctttttgct caagagcgat gttaatttgt tcaatcattt   7920
ggttaggaaa gcggatgttg cgggttgttg ttctgcgggt tctgttcttc gttgacatga   7980
ggttgccccg tattcagtgt cgctgatttg tattgtctga agttgttttt acgttaagtt   8040
gatgcagatc aattaatacg atacctgcgt cataattgat tatttgacgt ggtttgatgg   8100
cctccacgca cgttgtgata tgtagatgat aatcattatc actttacggg tcctttccgg   8160
tgatccgaca ggttacggcc tgatgcggta ttttctcctt acgcatctgt gcggtatttc   8220
acaccgcata cgtcaaagca accatagtac gcgccctgta gcggcgcatt aagcgcggcg   8280
```

-continued

```
ggtgtggtgg ttacgcgcag cgtgaccgct acacttgcca gcgccctagc gcccgctcct   8340
ttcgctttct tcccttcctt tctcgccacg ttcgccggct ttccccgtca agctctaaat   8400 cggggggctcc ctttagggtt ccgatttagt gctttacggc acctcgaccc caaaaaactt   8460
gatttgggtg atggttcacg tagtgggcca tcgccctgat agacggtttt tcgccctttg   8520
acgttggagt ccacgttctt taatagtgga ctcttgttcc aaactggaac aacactcaac   8580
cctatctcgg gctattcttt tgatttataa gggattttgc cgatttcggc ctattggtta   8640
aaaaatgagc tgatttaaca aaaatttaac gcgaatttta acaaaatatt aacgtttaca   8700
attttatggt gcactctcag tacaatctgc tctgatgccg catagttaag ccagccccga   8760
cacccgccaa cacccgctga cgcgccctga cgggcttgtc tgctcccggc atccgcttac   8820
agacaagctg tgaccgtctc cgggagctgc atgtgtcaga ggttttcacc gtcatcaccg   8880
aaacgcgcga gacgaaaggg cctcgtgata cgcctatttt tataggttaa tgtcatgata   8940
ataatggttt cttagacgtc aggtggcact tttcggggaa atgtgcgcgg aacccctatt   9000
tgtttatttt tctaaataca ttcaaatatg tatccgctca tgagacaata accctgataa   9060
atgcttcaat aatattgaaa aaggaagagt atgagtattc aacatttccg tgtcgccctt   9120
attccctttt ttgcggcatt ttgccttcct gttttttgctc acccagaaac gctggtgaaa   9180
gtaaaagatg ctgaagatca gttgggtgca cgagtgggtt acatcgaact ggatctcaac   9240
agcggtaaga tccttgagag ttttcgcccc gaagaacgtt ttccaatgat gagcactttt   9300
aaagttctgc tatgtggcgc ggtattatcc cgtattgacg ccgggcaaga gcaactcggt   9360
cgccgcatac actattctca gaatgacttg gttgagtact caccagtcac agaaaagcat   9420
cttacggatg gcatgacagt aagagaatta tgcagtgctg ccataaccat gagtgataac   9480
actgcggcca acttacttct gacaacgatc ggaggaccga aggagctaac cgcttttttg   9540
cacaacatgg gggatcatgt aactcgcctt gatcgttggg aaccggagct gaatgaagcc   9600
ataccaaacg acgagcgtga caccacgatg cctgtagcaa tggcaacaac gttgcgcaaa   9660
ctattaactg gcgaactact tactctagct tcccggcaac aattaataga ctggatggag   9720
gcggataaag ttgcaggacc acttctgcgc tcggcccttc cggctggctg gtttattgct   9780
gataaatctg gagccggtga gcgtgggtct cgcggtatca ttgcagcact ggggccagat   9840
ggtaagccct cccgtatcgt agttatctac acgacgggga gtcaggcaac tatggatgaa   9900
cgaaatagac agatcgctga gataggtgcc tcactgatta gcattggta actgtcagac   9960 caagtttact catatatact ttagattgat ttaaaacttc attttttaatt taaaaggatc  10020 taggtgaaga tcctttttga taatctcatg accaaaatcc cttaacgtga gttttcgttc  10080
cactgagcgt cagacccgt agaaaagatc aaaggatctt cttgagatcc ttttttttctg  10140 cgcgtaatct gctgcttgca acaaaaaaaa ccaccgctac cagcggtggt ttgtttgccg  10200
gatcaagagc taccaactct ttttccgaag gtaactggct tcagcagagc gcagatacca  10260
aatactgtcc ttctagtgta gccgtagtta ggccaccact tcaagaactc tgtagcaccg  10320
cctacatacc tcgctctgct aatcctgtta ccagtggctg ctgccagtgg cgataagtcg  10380
tgtcttaccg ggttggactc aagacgatag ttaccggata aggcgcagcg tcgggctga   10440 acggggggtt cgtgcacaca gcccagcttg gagcgaacga cctacaccga actgagatac  10500
ctacagcgtg agctatgaga aagcgccacg cttcccgaag ggagaaaggc ggacaggtat  10560
ccggtaagcg gcagggtcgg aacaggagag cgcacgaggg agcttccagg gggaaacgcc  10620
```

-continued

```
tggtatcttt atagtcctgt cgggtttcgc cacctctgac ttgagcgtcg attttttgtga    10680 tgctcgtcag gggggcggag cctatggaaa aacgccagca acgcggcctt tttacggttc    10740
ctggcctttt gctggccttt tgctcacatg tcctgcaggc ag                       10782
```

```
<210> SEQ ID NO 11
<211> LENGTH: 10776
<212> TYPE: DNA
<213> ORGANISM: Artificial Sequence
<220> FEATURE:
<223> OTHER INFORMATION: pAAV_AAVS1_C4-CD28CD3z-CAR.xdna

<400> SEQUENCE: 11
```

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct gcggcctaag cttgagcgga gttccaattg tactgtacag ccctttgctt     180
tctctgacca gcattctctc ccctgggcct gtgccgcttt ctgtctgcag cttgtggcct     240
gggtcacctc tacggctggc ccagatcctt ccctgccgcc tccttcaggt tccgtcttcc     300
tccactccct cttcccttg ctctctgctg tgttgctgcc caaggatgct ctttccggag      360
cacttccttc tcggcgctgc accacgtgat gtcctctgag cggatcctcc ccgtgtctgg     420
gtcctctccg ggcatctctc ctccctcacc caaccccatg ccgtcttcac tcgctgggtt     480 ccctttttcct tctccttctg gggctgtgc catctctcgt ttcttaggat ggccttctcc     540
gacggatgtc tcccttgcgt cccgcctccc cttcttgtag gcctgcatca tcaccgtttt     600 tctgacaac cccaaagtac cccgtctccc tggcttagc cacctctcca tcctcttgct       660
ttctttgcct ggacaccccg ttctcctgtg gattcgggtc acctctcact cctttcattt     720
gggcagctcc cctacccccc ttacctctct agtctgtgct agctcttcca gccccctgtc     780
atggcatctt ccaggggtcc gagagctcag ctagtcttct tcctccaacc cgggcccta      840 tgtccacttc aggacagcat gtttgctgcc tccaggggatc ctgtgtcccc gagctgggac     900
caccttatat tcccagggcc ggttaatgtg gctctggttc tgggtacttt tatctgtccc     960
ctccacccca cagtggggca agcttctgac ctcttctctt cctcccacag ggcctcgaga    1020
gatctggcgg cggagagggc agaggaagtc ttctaacatg cggtgacgtg gaggagaatc    1080
ccggccctat ggccttacca gtgaccgcct tgctcctgcc gctggccttg ctgctccacg    1140
ccgccaggcc gggatcccag ctggtggagt ctggggggagg cttggtacag ccagggcggt    1200
ccctgagact ctcctgcaca acttctggat tcacttttgg tgattatgct atgatctggg    1260
cccgccaggc tccagggaag gggctggagt gggtctcatc cattagtagt agtagtagtt    1320
acatatacta cgcagactca gtgaagggcc gattcaccat ctccagagac aacgccaaga    1380
actcactgta tctgcaaatg aacagcctga gagccgagga cacggctgtg tattactgtg    1440
cgagagaacg atacgatttt tggagtggaa tggacgtctg gggcaaaggg accacggtca    1500
ccgtctcgag tggtggaggc ggttcaggcg gaggtggctc tggcggtagt gcacagtctg    1560
ccctgactca gcctgcctcc gtgtctgggt ctcctggaca gtcgatcacc atctcctgca    1620
ctggaaccag cagtgatgtt gggagttata accttgtctc ctggtaccaa cagcacccag    1680
gcaaagcccc caaactcatg atttatgagg gcagtaagcg gccctcaggg gtttctaatc    1740
gcttctctgg ctccaagtct ggcaacgcgg cctccctgac aatctctggg ctccaggctg    1800
aggacgaggc tgattattac tgccagtcct atgacagcag cctgagtgtg gtattcggcg    1860
gagggaccaa gctgaccgtc ctaggtgcta gcaccacgac gccagcgccg cgaccaccaa    1920
```

-continued

```
caccggcgcc caccatcgcg tcgcagcccc tgtccctgcg cccagaggcg tgccggccag      1980 cggcggggggg cgcagtgcac acgaggggggc tggacttcgc ctgtgattttt tgggtgctgg    2040 tggtggttgg tggagtcctg gcttgctata gcttgctagt aacagtggcc tttattatttt     2100 tctgggtgag gagtaagagg agcaggctcc tgcacagtga ctacatgaac atgactcccc      2160
gccgccccgg gcccacccgc aagcattacc agccctatgc cccaccacgc gacttcgcag      2220
cctatcgctc catcgataga gtgaagttca gcaggagcgc agacgccccc gcgtaccagc      2280
agggccagaa ccagctctat aacgagctca atctaggacg aagagaggag tacgatgttt      2340
tggacaagag acgtggccgg gaccctgaga tgggggggaaa gccgagaagg aagaaccctc     2400
aggaaggcct gtacaatgaa ctgcagaaag ataagatggc ggaggcctac agtgagattg      2460
ggatgaaagg cgagcgccgg aggggcaagg ggcacgatgg cctttaccag ggtctcagta      2520
cagccaccaa ggacacctac gacgcccttc acatgcaggc cctgccccct cgctgataag      2580
cggccgcctg tgccttctag ttgccagcca tctgttgttt gcccctcccc cgtgccttcc      2640
ttgaccctgg aaggtgccac tcccactgtc ctttcctaat aaaatgagga aattgcatcg      2700
cattgtctga gtaggtgtca ttctattctg gggggtgggg tggggcagga cagcaagggg      2760
gaggattggg aagacaatag caggcatgct ggggatgcgg tgggctctat gggtcgacag      2820
tactaagctt tactagggac aggattggtg acagaaaagc cccatcctta ggcctcctcc      2880
ttcctagtct cctgatattg ggtctaaccc ccacctcctg ttaggcagat tccttatctg      2940
gtgacacacc cccatttcct ggagccatct ctctccttgc cagaacctct aaggtttgct      3000
tacgatggag ccagagagga tcctgggagg gagagcttgg caggggggtgg gaggggaaggg    3060 ggggatgcgt gacctgcccg gttctcagtg gccaccctgc gctaccctct cccagaacct      3120
gagctgctct gacgcggctg tctggtgcgt ttcactgatc ctggtgctgc agcttcctta      3180
cacttcccaa gaggagaagc agtttggaaa aacaaaatca gaataagttg gtcctgagtt      3240
ctaactttgg ctcttcacct ttctagtccc caatttatat tgttcctccg tgcgtcagtt      3300
ttacctgtga gataaggcca gtagccagcc ccgtcctggc agggctgtgg tgaggaggggg     3360 ggtgtccgtg tggaaaactc cctttgtgag aatggtgcgt cctaggtgtt caccaggtcg      3420
tggccgcctc tactcccttt ctctttctcc atccttcttt ccttaaagag tccccagtgc      3480
tatctgggac atattcctcc gcccagagca gggtcccgct tccctaaggc cctgctctgg      3540
gcttctgggt ttgagtcctt ggcaagccca ggagaggcgc tcaggcttcc ctgtccccct      3600
tcctcgtcca ccatctcatg cccctggctc tcctgcccct tccctacagg ggttcctggc      3660
tctgctctaa gggggtaccc tcgagcgcag gaacccctag tgatggagtt ggccactccc      3720
tctctgcgcg ctcgctcgct cactgaggcc gcccgggctt gcccgggcg gcctcagtga       3780 gcgagcgagc gcgcagctgc ctgcaggggc agcttgaagg aaatactaag gcaaaggtac      3840
tgcaagtgct cgcaacattc gcttatgcgg attattgccg tagtgccgcg acgccggggg     3900
caagatgcag agattgccat ggtacaggcc gtgcggttga tattgccaaa acagagctgt      3960 ggggggagagt tgtcgagaaa gagtgcggaa gatgcaaagg cgtcggctat tcaaggatgc     4020
cagcaagcgc agcatatcgc gctgtgacga tgctaatccc aaaccttacc caacccacct      4080
ggtcacgcac tgttaagccg ctgtatgacg ctctggtggt gcaatgccac aaagaagagt      4140
caatcgcaga caacattttg aatgcggtca cacgttagca gcatgattgc cacggatggc      4200
aacatattaa cggcatgata ttgacttatt gaataaaatt gggtaaattt gactcaacga      4260
```

```
tgggttaatt cgctcgttgt ggtagtgaga tgaaaagagg cggcgcttac taccgattcc    4320
gcctagttgg tcacttcgac gtatcgtctg gaactccaac catcgcaggc agagaggtct    4380
gcaaaatgca atcccgaaac agttcgcagg taatagttag agcctgcata acggtttcgg    4440
gattttttat atctgcacaa caggtaagag cattgagtcg ataatcgtga agagtcggcg    4500
agcctggtta gccagtgctc tttccgttgt gctgaattaa gcgaataccg gaagcagaac    4560
cggatcacca aatgcgtaca ggcgtcatcg ccgcccagca acagcacaac ccaaactgag    4620
ccgtagccac tgtctgtcct gaattcatta gtaatagtta cgctgcggcc ttttacacat    4680
gaccttcgtg aaagcgggtg gcaggaggtc gcgctaacaa cctcctgccg ttttgcccgt    4740
gcatatcggt cacgaacaaa tctgattact aaacacagta gcctggattt gttctatcag    4800
taatcgacct tattcctaat taaatagagc aaatcccctt attgggggta agacatgaag    4860
atgccagaaa aacatgacct gttggccgcc attctcgcgg caaaggaaca aggcatcggg    4920
gcaatccttg cgtttgcaat ggcgtacctt cgcggcagat ataatggcgg tgcgtttaca    4980
aaaacagtaa tcgacgcaac gatgtgcgcc attatcgcct ggttcattcg tgaccttctc    5040
gacttcgccg gactaagtag caatctcgct tatataacga gcgtgtttat cggctacatc    5100
ggtactgact cgattggttc gcttatcaaa cgcttcgctg ctaaaaaagc cggagtagaa    5160
gatggtagaa atcaataatc aacgtaaggc gttcctcgat atgctggcgt ggtcggaggg    5220
aactgataac ggacgtcaga aaaccagaaa tcatggttat gacgtcattg taggcggaga    5280
gctatttact gattactccg atcaccctcg caaacttgtc acgctaaacc caaaactcaa    5340
atcaacaggc gccggacgct accagcttct ttcccgttgg tgggatgcct accgcaagca    5400
gcttggcctg aaagacttct ctccgaaaag tcaggacgct gtggcattgc agcagattaa    5460
ggagcgtggc gctttaccta tgattgatcg tggtgatatc cgtcaggcaa tcgaccgttg    5520
cagcaatatc tgggcttcac tgccgggcgc tggttatggt cagttcgagc ataaggctga    5580
cagcctgatt gcaaaattca aagaagcggg cggaacggtc agagagattg atgtatgagc    5640
agagtcaccg cgattatctc cgctctggtt atctgcatca tcgtctgcct gtcatgggct    5700
gttaatcatt accgtgataa cgccattacc tacaaagccc agcgcgacaa aaatgccaga    5760
gaactgaagc tggcgaacgc ggcaattact gacatgcaga tgcgtcagcg tgatgttgct    5820
gcgctcgatg caaaatacac gaaggagtta gctgatgcta agctgaaaaa tgatgctctg    5880
cgtgatgatg ttgccgctgg tcgtcgtcgg ttgcacatca aagcagtctg tcagtcagtg    5940
cgtgaagcca ccaccgcctc cggcgtggat aatgcagcct cccccgact ggcagacacc    6000 gctgaacggg attatttcac cctcagagag aggctgatca ctatgcaaaa acaactggaa    6060
ggaacccaga gtatattaa tgagcagtgc agatagagtt gcccatatcg atgggcaact    6120
catgcaatta ttgtgagcaa tacacacgcg cttccagcgg agtataaatg cctaaagtaa    6180
taaaaccgag caatccattt acgaatgttt gctgggtttc tgttttaaca acattttctg    6240
cgccgccaca aattttggct gcatcgacag ttttcttctg cccaattcca gaaacgaaga    6300
aatgatgggt gatggtttcc tttggtgcta ctgctgccgg tttgtttttga acagtaaacg    6360 tctgttgagc acatcctgta ataagcaggg ccagcgcagt agcgagtagc atttttttca    6420
tggtgttatt cccgatgctt tttgaagttc gcagaatcgt atgtgtagaa aattaaacaa    6480
accctaaaca atgagttgaa atttcatatt gttaatattt attaatgtat gtcaggtgcg    6540
atgaatcgtc attgtattcc cggattaact atgtccacag ccctgacggg gaacttctct    6600
gcgggagtgt ccgggaataa ttaaaacgat gcacacaggg tttagcgcgt acacgtattg    6660
```

-continued

```
cattatgcca acgccccggt gctgacacgg aagaaaccgg acgttatgat ttagcgtgga   6720
aagatttgtg tagtgttctg aatgctctca gtaaatagta atgaattatc aaaggtatag   6780
taatatcttt tatgttcatg gatatttgta acccatcgga aaactcctgc tttagcaaga   6840
ttttccctgt attgctgaaa tgtgatttct cttgatttca acctatcata ggacgtttct   6900
ataagatgcg tgtttcttga gaatttaaca tttacaacct ttttaagtcc ttttattaac   6960
acggtgttat cgttttctaa cacgatgtga atattatctg tggctagata gtaaatataa   7020
tgtgagacgt tgtgacgttt tagttcagaa taaaacaatt cacagtctaa atcttttcgc   7080
acttgatcga atatttcttt aaaaatggca acctgagcca ttggtaaaac cttccatgtg   7140
atacgagggc gcgtagtttg cattatcgtt tttatcgttt caatctggtc tgacctcctt   7200
gtgttttgtt gatgatttat gtcaaatatt aggaatgttt tcacttaata gtattggttg   7260
cgtaacaaag tgcggtcctg ctggcattct ggagggaaat acaaccgaca gatgtatgta   7320
aggccaacgt gctcaaatct tcatacagaa agatttgaag taatatttta accgctagat   7380
gaagagcaag cgcatggagc gacaaaatga ataaagaaca atctgctgat gatccctccg   7440
tggatctgat tcgtgtaaaa aatatgctta atagcaccat ttctatgagt taccctgatg   7500
ttgtaattgc atgtatagaa cataaggtgt ctctggaagc attcagagca attgaggcag   7560
cgttggtgaa gcacgataat aatatgaagg attattccct ggtggttgac tgatcaccat   7620
aactgctaat cattcaaact atttagtctg tgacagagcc aacacgcagt ctgtcactgt   7680
caggaaagtg gtaaaactgc aactcaatta ctgcaatgcc ctcgtaatta agtgaattta   7740
caatatcgtc ctgttcggag ggaagaacgc gggatgttca ttcttcatca cttttaattg   7800
atgtatatgc tctcttttct gacgttagtc tccgacggca ggcttcaatg acccaggctg   7860
agaaattccc ggaccctttt tgctcaagag cgatgttaat ttgttcaatc atttggttag   7920
gaaagcggat gttgcgggtt gttgttctgc gggttctgtt cttcgttgac atgaggttgc   7980
cccgtattca gtgtcgctga tttgtattgt ctgaagttgt ttttacgtta agttgatgca   8040
gatcaattaa tacgatacct gcgtcataat tgattatttg acgtggtttg atggcctcca   8100
cgcacgttgt gatatgtaga tgataatcat tatcacttta cgggtccttt ccggtgatcc   8160
gacaggttac ggcctgatgc ggtattttct ccttacgcat ctgtgcggta tttcacaccg   8220
catacgtcaa agcaaccata gtacgcgccc tgtagcggcg cattaagcgc ggcgggtgtg   8280
gtggttacgc gcagcgtgac cgctacactt gccagcgccc tagcgcccgc tcctttcgct   8340
ttcttccctt cctttctcgc cacgttcgcc ggctttcccc gtcaagctct aaatcggggg   8400 ctcccttta g ggttccgatt tagtgcttta cggcacctcg accccaaaaa acttgatttg   8460
ggtgatggtt cacgtagtgg gccatcgccc tgatagacgg ttttcgccc  tttgacgttg   8520 gagtccacgt tctttaatag tggactcttg ttccaaactg gaacaacact caaccctatc   8580
tcgggctatt cttttgattt ataagggatt ttgccgattt cggcctattg gttaaaaaat   8640
gagctgattt aacaaaaatt taacgcgaat tttaacaaaa tattaacgtt tacaatttta   8700
tggtgcactc tcagtacaat ctgctctgat gccgcatagt taagccagcc ccgacacccg   8760
ccaacacccg ctgacgcgcc ctgacgggct tgtctgctcc cggcatccgc ttacagacaa   8820
gctgtgaccg tctccgggag ctgcatgtgt cagaggtttt caccgtcatc accgaaacgc   8880
gcgagacgaa agggcctcgt gatacgccta ttttttatagg ttaatgtcat gataataatg   8940
gtttcttaga cgtcaggtgg cacttttcgg ggaaatgtgc gcggaacccc tatttgttta   9000
```

-continued

```
ttttttctaaa tacattcaaa tatgtatccg ctcatgagac aataaccctg ataaatgctt    9060
caataatatt gaaaaaggaa gagtatgagt attcaacatt tccgtgtcgc ccttattccc    9120
ttttttgcgg cattttgcct tcctgttttt gctcacccag aaacgctggt gaaagtaaaa    9180
gatgctgaag atcagttggg tgcacgagtg ggttacatcg aactggatct caacagcggt    9240
aagatccttg agagttttcg ccccgaagaa cgttttccaa tgatgagcac ttttaaagtt    9300
ctgctatgtg gcgcggtatt atcccgtatt gacgccgggc aagagcaact cggtcgccgc    9360
atacactatt ctcagaatga cttggttgag tactcaccag tcacagaaaa gcatcttacg    9420
gatggcatga cagtaagaga attatgcagt gctgccataa ccatgagtga taacactgcg    9480
gccaacttac ttctgacaac gatcggagga ccgaaggagc taaccgcttt tttgcacaac    9540 atggggatc atgtaactcg ccttgatcgt tgggaaccgg agctgaatga agccatacca    9600
aacgacgagc gtgacaccac gatgcctgta gcaatggcaa caacgttgcg caaactatta    9660
actggcgaac tacttactct agcttcccgg caacaattaa tagactggat ggaggcggat    9720
aaagttgcag gaccacttct gcgctcggcc cttccggctg gctggtttat tgctgataaa    9780
tctggagccg gtgagcgtgg gtctcgcggt atcattgcag cactggggcc agatggtaag    9840
ccctcccgta tcgtagttat ctacacgacg gggagtcagg caactatgga tgaacgaaat    9900
agacagatcg ctgagatagg tgcctcactg attaagcatt ggtaactgtc agaccaagtt    9960
tactcatata cttttagat tgatttaaaa cttcattttt aatttaaaag gatctaggtg    10020
aagatccttt ttgataatct catgaccaaa atcccttaac gtgagttttc gttccactga    10080
gcgtcagacc ccgtagaaaa gatcaaagga tcttcttgag atcctttttt tctgcgcgta    10140
atctgctgct tgcaaacaaa aaaaccaccg ctaccagcgg tggtttgttt gccggatcaa    10200
gagctaccaa ctctttttcc gaaggtaact ggcttcagca gagcgcagat accaaatact    10260
gtccttctag tgtagccgta gttaggccac cacttcaaga actctgtagc accgcctaca    10320
tacctcgctc tgctaatcct gttaccagtg gctgctgcca gtggcgataa gtcgtgtctt    10380
accgggttgg actcaagacg atagttaccg gataaggcgc agcggtcggg ctgaacgggg    10440
ggttcgtgca cacagcccag cttggagcga acgacctaca ccgaactgag atacctacag    10500
cgtgagctat gagaaagcgc cacgcttccc gaagggagaa aggcggacag gtatccggta    10560
agcggcaggg tcggaacagg agagcgcacg agggagcttc caggggggaaa cgcctggtat    10620 ctttatagtc ctgtcgggtt tcgccacctc tgacttgagc gtcgattttt gtgatgctcg    10680
tcaggggggc ggagcctatg gaaaaacgcc agcaacgcgg cctttttacg gttcctggcc    10740
ttttgctggc cttttgctca catgtcctgc aggcag                              10776
```

```
<210> SEQ ID NO 12
<211> LENGTH: 32
<212> TYPE: DNA
<213> ORGANISM: Homo sapiens

<400> SEQUENCE: 12
gctccagcta cggaaagtca gattactgga gg                                      32

<210> SEQ ID NO 13
<211> LENGTH: 32
<212> TYPE: DNA
<213> ORGANISM: Homo sapiens

<400> SEQUENCE: 13
cctccagtaa tctgactttc cgtagctgga gc                                      32
```

<210> SEQ ID NO 14
<211> LENGTH: 32
<212> TYPE: DNA
<213> ORGANISM: Homo sapiens

<400> SEQUENCE: 14
caggctcctc aagtggtact actcggtgca tg                              32

<210> SEQ ID NO 15
<211> LENGTH: 32
<212> TYPE: DNA
<213> ORGANISM: Homo sapiens

<400> SEQUENCE: 15
catgcaccga gtagtaccac ttgaggagcc tg                              32

<210> SEQ ID NO 16
<211> LENGTH: 32
<212> TYPE: DNA
<213> ORGANISM: Homo sapiens

<400> SEQUENCE: 16
agagaagttc ggcaatcttg ttactggtac tc                              32

<210> SEQ ID NO 17
<211> LENGTH: 32
<212> TYPE: DNA
<213> ORGANISM: Homo sapiens

<400> SEQUENCE: 17
gagtaccagt aacaagattg ccgaacttct ct                              32

<210> SEQ ID NO 18
<211> LENGTH: 32
<212> TYPE: DNA
<213> ORGANISM: Homo sapiens

<400> SEQUENCE: 18 tggacccta acattaggca gcgatccgtt ta                               32

<210> SEQ ID NO 19
<211> LENGTH: 32
<212> TYPE: DNA
<213> ORGANISM: Homo sapiens

<400> SEQUENCE: 19
taaacggatc gctgcctaat gttaagggtc ca                              32

<210> SEQ ID NO 20
<211> LENGTH: 30
<212> TYPE: DNA
<213> ORGANISM: Homo sapiens

<400> SEQUENCE: 20
cgatccgttt atgtatcctt agtcaggtgt                                30

<210> SEQ ID NO 21
<211> LENGTH: 30
<212> TYPE: DNA
<213> ORGANISM: Homo sapiens

<400> SEQUENCE: 21

-continued

```
acacctgact aaggatacat aaacggatcg                                    30

<210> SEQ ID NO 22
<211> LENGTH: 32
<212> TYPE: DNA
<213> ORGANISM: Homo sapiens

<400> SEQUENCE: 22
tcaatgtcac gttctcctac ctagttggtt gg                                 32

<210> SEQ ID NO 23
<211> LENGTH: 32
<212> TYPE: DNA
<213> ORGANISM: Homo sapiens

<400> SEQUENCE: 23
ccaaccaact aggtaggaga acgtgacatt ga                                 32

<210> SEQ ID NO 24
<211> LENGTH: 20
<212> TYPE: DNA
<213> ORGANISM: Artificial Sequence
<220> FEATURE:
<223> OTHER INFORMATION: Target 56

<400> SEQUENCE: 24
catcaagttc agctcttcct                                               20

<210> SEQ ID NO 25
<211> LENGTH: 20
<212> TYPE: DNA
<213> ORGANISM: Artificial Sequence
<220> FEATURE:
<223> OTHER INFORMATION: Target 150

<400> SEQUENCE: 25
gatcacaagc aactctggat                                               20
```

COMPOSITIONS AND METHODS FOR ENHANCED LYMPHOCYTE-MEDIATED IMMUNOTHERAPY

REFERENCE TO RELATED APPLICATIONS

This application is a 371 national phase entry of Patent Cooperation Treaty application No. PCT/CA2020/050185 filed 12 Feb. 2020, which claims priority to, and the benefit of, U.S. provisional patent application No. 62/804,658 filed 12 Feb. 2019, both entitled COMPOSITIONS AND METHODS FOR ENHANCED LYMPHOCYTE-MEDIATED IMMUNOTHERAPY. All of the foregoing applications are incorporated by reference herein in their entireties for all purposes.

GOVERNMENT LICENSE RIGHTS

This invention was made, in part, with government support under Grant Number OC170169 made under Award Number W81XWH-18-1-0264 awarded by the U.S. Army Medical Research and Development Command. The government has certain rights in the invention.

FIELD OF THE INVENTION

Some embodiments of this invention relate to genetically engineered lymphocytes having improved efficacy as immunotherapeutics. Some embodiments of this invention relate to methods and compositions to modify the metabolism of lymphocytes in order to improve their efficacy as immunotherapeutics. Some embodiments relate to methods for the genetic manipulation of autophagy in chimeric antigen receptor T-cells (CAR-T) or engineered or endogenous T cell receptor T-cells (TCR-T) to enhance their effectiveness for immunotherapy of cancer.

BACKGROUND

CAR-T-cells are engineered with an antigen-binding domain such as an antibody single chain variable fragment (scFv) to bind antigens expressed on the cell surface of tumor cells. In standard therapy, a CAR construct is transduced into autologous CD3+ T-cells, expanded ex vivo and then infused into a patient. "New generation" CAR-T-cells contain optimized CD3ζ signalling domains fused in combination with co-stimulatory molecules such as CD28, 41BBL and CD27 (3). Despite these modifications, the persistence of CAR-T-cells in solid tumors remains poor. Thus, other barriers besides pro-survival signals control the function of CAR-T-cells in the tumor microenvironment.

Despite decades of research, treatments for ovarian cancer have not improved patient outcomes. High-grade serous carcinoma (HGSC), the most common histotype, is often diagnosed at stage 3-4 disease and patients receive debulking surgery followed by several rounds of chemotherapy. The 5-year survival rate for stage 4 disease is <20%. Although vaccines, checkpoint blockade and T-cell therapy have been explored, early trials have not improved overall patient survival. However, there is unequivocal evidence that the presence and function of tumor infiltrating lymphocytes (TIL) is strongly associated with improved survival implying that the immune system is beneficial in this disease (4).

Folate receptors (FR) exist as 3 isoforms, α, β, and γ, and function in folic acid and folate uptake. High levels of αFR have been observed in ovarian, breast and lung cancers but are low in normal tissue (5). In one trial, 14 ovarian cancer patients who received infusions of αFR-CAR-T-cells with or without IL-2 showed no evidence of clinical response despite treatment being well-tolerated. Using radiolabel tracer imaging, the authors concluded that the αFR-CAR-T-cells were unable to persist shortly after infusion (2). Therefore, the current approaches to use αFR-CAR-T in ovarian cancer have not been successful, in part, due to the lack of persistence of cells after infusion. However, this work provides an established safety profile for αFR-CAR-T therapy.

Manufacturing CAR-T-cells requires specialized infrastructure, patients must undergo lymphodepletion prior to T-cell infusions and acute life-threatening immune adverse events can arise. Moreover, CAR-T-cells have shown limited efficacy in solid tumors (6). One possibility to explain the lack of observed efficacy for solid tumors is a metabolic barrier imposed by the tumor ecosystem due to the high metabolic demands of rapidly proliferating tumor cells. Ultimately, this may cause a loss of T-cell function and persistence. Thus, it appears that metabolism can significantly impact T-cell behaviour providing a unique opportunity to modify T-cell metabolism and achieve better therapeutic success in solid cancers.

Deregulation of central metabolism is a universal hallmark of cancers, an observation reported for ovarian cancer (7). There is widespread appreciation that cancers use glucose and glutamine at high rates to serve as the main biosynthetic precursor for cell growth and proliferation (8). Recent work demonstrates that T-cells have adaptive metabolism depending on their state of activation and differentiation (7,9-12). For example, the transition from a naïve T-cell to an activated effector cell is accompanied by switch from oxidative metabolism to a more glycolytic phenotype (9). The metabolic similarities of proliferating T-cells and tumor cells is striking and implies that insufficiencies in glucose and other nutrients that are essential to support proliferation can contribute to reduced T-cell function and exhaustion (10).

Metabolic competition could suppress T-cells that have been infused as part of T-cell therapy. One report found that CD8+ tumor infiltrating lymphocytes (TIL) in murine tumors were more functional in tumors with reduced glucose consumption compared to tumors with high rates of glycolysis suggesting that glucose consumption by tumors directly impaired T-cell activity (10). This defect was rescued by expressing metabolic enzymes that restore T-cell glycolysis. In another report, loss of mitochondrial mass in tumor-infiltrating lymphocytes (TIL) was associated with a reduction in type 1 cytokines, increased checkpoint inhibitor expression and loss of anti-tumor activity (13). However, enforced expression of PGC1α, a transcription factor involved in mitochondria biogenesis, restored anti-tumor immunity. In the face of metabolic stress, reprogramming TIL to use alternative fuels may help sustain their anti-tumor activity. Despite these studies, there are no reports examining the role of metabolism on human TIL known to the inventors.

Autophagy is a form of catabolic metabolism where cells engulf portions of the cytosol and degrade cellular contents in the lysosome for metabolite recycling, protein quality control or destruction of damaged organelles (14). Autophagy is largely a survival pathway activated by nutrient and growth factor deprivation (14). T-cells lacking autophagy genes such as Atg5 or Atg7 have impaired thymocyte development and a reduction in peripheral T-cells (15). In line with this, it has been reported that autophagy is essential for CD8+ effector T-cell survival and memory development (16, 17).

Given the fundamental role that metabolism plays in organismal homeostasis and cancer, one might expect deleterious or pro-oncogenic phenotypes associated with manipulating the autophagy pathway. In the case of autophagy deficiency, haploinsufficency of one autophagy gene, Beclin-1, has been found to promote tumor formation and monoallelic deletion is observed in 40-75% of sporadic breast, ovarian and prostate cancer (18). Moreover, aged Atg5 or Atg7 liver-specific knockouts develop spontaneous liver tumors (19). It is believed that loss of Atg5 in T-cells does not lead to oncogenesis based on the inventors' own observations. Moreover, gain- or loss-of-function in metabolic genes is required but not sufficient for tumorigenesis. For instance, T-cell specific Glut1 transgenic mice do not spontaneously develop tumors (20).

There have been reports using CRISPR/Cas9 for gene-editing in primary human T-cells (21, 22). A Chinese group has successfully knocked out PD-1 in T-cells, though the details of their strategy have yet to be reported. Another group was able to target the CD19 CAR to the T-cell receptor-α locus and cause enhanced tumor rejection in a mouse model (22). Most recently, a group at the University of Pennsylvania led by Carl June successfully conducted a first-in-human phase 1 trial testing the safety and feasibility of multiplex CRISPR-Cas9 editing in T-cells (24).

Many types of cells are involved in killing tumor cells, including NK cells; T-cells including CD34+, CD4+ or CD8+ T-cells, Treg cells, tissue-resident memory T cells (TRM cells), natural killer T-cells (NKT); B-cells, and the like. These cells act through a similar mechanism of recognizing an antigen such as a tumor-specific antigen on the surface of the tumor cell and acting to kill such cell.

Some embodiments of the present invention address an unmet need in the field for improved treatments using lymphocytes for immunotherapy, including CAR-T therapy, especially for treatment of solid cancers, for example those of the ovary, breast or lung.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, a lymphocyte having an antigen targeting receptor and a suppressed autophagy gene is provided. In some aspects, the lymphocyte is provided with a nucleic acid encoding the antigen targeting receptor inserted within a locus of the autophagy gene to disrupt expression of the autophagy gene. In some aspects, the autophagy gene is located at a first locus of the genome and the nucleic acid encoding the antigen targeting receptor is inserted at a second locus of the genome that is different from the first locus. In some such aspects, the autophagy gene is knocked out or disrupted at the first locus or suppressed in some other manner, for example using RNAi.

In one aspect, a method of conducting immunotherapy is provided that involves administering to a subject an engineered lymphocyte as described in this specification. In one aspect, a method of conducting immunotherapy is provided in which lymphocytes that have been modified to suppress an autophagy gene are administered to a subject. In some aspects, a method of conducting immunotherapy is provided in which lymphocytes that have been modified to both suppress an autophagy gene and express an antigen targeting receptor are administered to a subject. In some aspects, the immunotherapy is used to treat cancer.

In one aspect, a method of making a lymphocyte for use in immunotherapy is provided and involves modifying the lymphocyte to suppress an autophagy gene. In some such aspects, the lymphocyte is further modified to express a desired antigen targeting receptor.

In some aspects, any suitable technique may be used to suppress expression of the autophagy gene, including using CRISPR-Cas, zinc-finger nucleases (ZFN), transcription activator-like effector nucleases (TALEN), Sleeping Beauty (SB), RNAi, meganucleases, or megaTALs. In some aspects, the autophagy gene is disrupted or knocked out, for example using CRISPR-Cas, zinc-finger nucleases (ZFN), transcription activator-like effector nucleases (TALEN), Sleeping Beauty (SB), meganucleases, or megaTALs.

In some aspects, methods and compositions to improve the anti-tumor efficacy of lymphocytes are provided. In some aspects, methods and compositions to improve the anti-tumor efficacy of cytotoxic lymphocytes are provided. In some aspects, methods and compositions to improve the anti-tumor efficacy of cytotoxic cells are provided. In some aspects, methods and compositions to improve the anti-tumor efficacy of lymphocytes including NK cells; T-cells including CD34+, CD4+ or CD8+ T-cells, Treg cells, tissue-resident memory T cells (TRM cells), natural killer T-cells (NKT); B-cells; or the like are provided.

In some aspects, the genetically engineered lymphocytes express an antigen targeting receptor such as a chimeric antigen receptor (CAR) or an endogenous or engineered T-cell receptor which targets a desired tumor-specific antigen.

In some aspects, methods and compositions to improve the anti-tumor efficacy of T-cells (T-lymphocytes) for use in adoptive cellular cancer immunotherapy, comprising suppression of autophagy in said T-cells are provided.

In one aspect, methods to improve the anti-tumor efficacy of chimeric antigen receptor (CAR) T-cells (CAR-T) for therapy of cancer by suppressing autophagy in said CAR-T-cells are provided.

In one aspect, the novel use of gene-editing methods (including but not limited to CRISPR-Cas9) to insert CAR nucleic-acid sequences at the loci of autophagy (ATG) genes in primary human autologous T-cells to generate 'knock-in' CAR-T-cells deficient in autophagy is provided. These CAR-T-cells are deficient in expression of the ATG gene targeted by the CAR sequences using CRISPR-Cas9 and are believed to have improved anti-tumor efficacy (against tumors specifically targeted by the CAR-T) by virtue of the ablated or suppressed ATG gene.

In one aspect, the T-cell autophagy (ATG) gene targeted for 'knock-in' of the CAR sequences using CRISPR-Cas9 gene editing (or targeted for knock-out or suppression in other aspects) may be any autophagy-related (ATG) gene known by those skilled in the art and may include but are not limited to ATG1, ATG4, ATG5, ATG7, ATG8, ATG13, ATG4, ATG18, ATG16L1, and GABARP. In some aspects, the autophagy gene that is suppressed in the lymphocyte is one or more of ULK1, ULK2, ULK3, FIP200, Vps34, Beclin-1, p150, UVRAG, ATG1, ATG4, ATG5, ATG7, ATG8, ATG9, ATG10, ATG12, ATG13, ATG14L, ATG16L, ATG16L1, ATG18, VMP1, GABARAP, or the like.

In one aspect, the CAR sequences used in the CRISPR-Cas9 knock-in at the chosen ATG gene locus of the T-cell may be directed to (specific for) any desired tumor (or disease/target) antigen. In some aspects, the antigen targeted by the antigen targeting receptor is a tumor-specific antigen including but not limited to CD19, CD20, BCMA, Her2, EGFRvIII, PSMA (prostate specific membrane antigen) and the FR (folate receptor) for example. In some aspects, the tumor-specific antigen is the folate receptor (FR), the α-folate receptor, the β-folate receptor, the γ-folate receptor, CD19, CD20, CD133, CD138, CEA, Claudin 18.2, EGFR, EGFRvIII, EphA2, EpCAM, GD2, GPC3, HER2, MSLN, MG7, MUC1, NY-ESO-1, LMP1, PSMA, Fra, NKG2DI, BCMA, IL13Ralpha2, LeY, CD70, B7-H3, ROR1, PSCA, or the like.

In one aspect, an engineered CAR-T-cell in which CAR sequences specific for the alpha (a) folate receptor (αFR) are 'knocked-in' to the ATG5 gene locus of T-cells using CRISPR-Cas9 gene-editing. This generates a novel engineered CAR-T-cell (termed αFR-CAR-T) with ablated ATG5 gene activity/function that has improved anti-tumour activity (relative to ATG wild-type T-cells) for treatment of α-FR-expressing cancers including but not limited to ovarian, breast and lung cancer. Expression of the αFR-CAR following targeted integration into the ATG5 locus may be driven by the endogenous gene promoter or using heterologous promoters. Methods for nuclease and donor delivery are known by persons skilled in the art and can include electroporation of nucleic acids or ribonucleoprotein (RNP) complexes or recombinant virus-mediated delivery.

In one aspect, an engineered CAR-T-cell in which CAR sequences specific for the alpha (a) folate receptor (αFR) are 'knocked-in' to the ATG14 gene locus of T-cells using CRISPR-Cas9 gene-editing. This generates an engineered CAR-T-cell (termed αFR-CAR-T) with ablated ATG14 gene activity/function that has improved anti-tumour activity (relative to ATG wild-type T-cells) for treatment of α-FR-expressing cancers including but not limited to ovarian, breast and lung cancer.

In one aspect, the αFR-CAR sequences for the knock-in are targeted to intron 2 of the ATG5 locus. In one aspect, the αFR-CAR is introduced by any suitable method (for example, via electroporation or suitable lentiviral vector or retroviral vector), and then ATG5 is knocked out. In some such aspects, ATG5 is knocked out at exon 4 or exon 5 of the ATG5 locus.

In one aspect, the sgRNA construct design for the CRISPR-Cas9-mediated knock-in to the ATG5 locus has the nucleotide sequence of SEQ ID NOs:1-7 OR 24-25.

In one aspect, the primary T-cells used to generate CAR-T knock-ins at various ATG gene loci of the invention, may be induced pluripotent stem cells, CD34+, CD4+ or CD8+ T-cells.

In one aspect, more than one ATG loci/gene (i.e. two or more different ATG genes) may be simultaneously edited for knock-in by a particular CAR sequence/construct for improved anti-tumour efficacy.

In one aspect, the αFR-CAR sequences for the knock-in are targeted to introns or exons (i.e. exons 1, 2, 3, 4 etc.) other than intron 2 of the ATG5 locus/gene.

Further aspects of the invention will become apparent from consideration of the ensuing description of preferred embodiments of the invention. A person skilled in the art will realise that other embodiments of the invention are possible and that the details of the invention can be modified in a number of respects, all without departing from the inventive concept. Thus, the following drawings, descriptions and examples are to be regarded as illustrative in nature and not restrictive.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Figure 1:
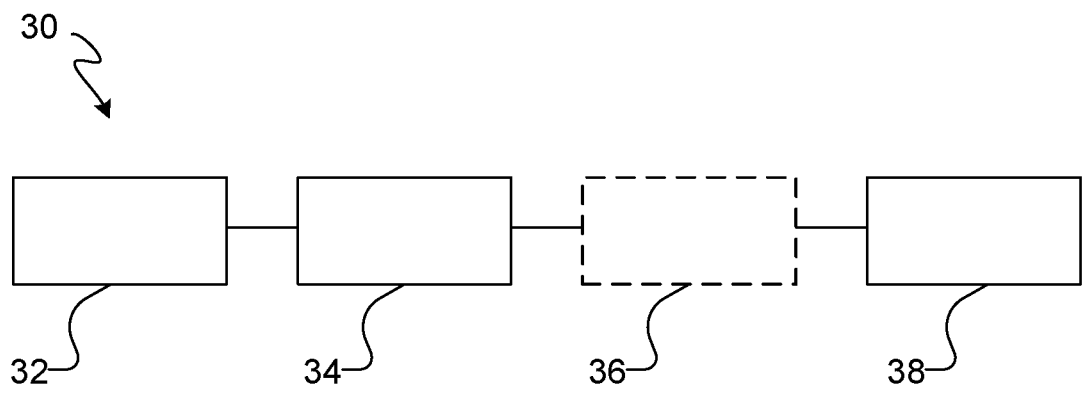
FIG. 1 is a schematic diagram showing schematically an example embodiment of a chimeric antigen receptor (CAR).

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

The inventors have now found methods and compositions to improve the anti-tumor efficacy of lymphocytes that have application, for example, in chimeric antigen receptor (CAR) T-cell therapy or T-cell receptor-engineered T-cell therapy. Gene-editing methods for the ablation of autophagy gene expression in lymphocytes including CAR-T-cells have been developed to enhance the therapeutic efficacy of the cells, including against solid tumors. In some embodiments, the gene-editing methods cause the engineered lymphocytes, such as CAR-T-cells, to specifically target the alpha-folate receptor (αFR) in order to improve their effectiveness for treatment of cancers that express the αFR such as ovarian, breast and lung cancer.

In one aspect, the inventors have designed a novel CRISPR-Cas9 gene-editing strategy to engineer autophagy-deficient lymphocytes, including CAR-T-cells, directed against the ovarian cancer antigen folate receptor alpha (αFR) as an exemplary tumor-specific antigen. By using a gene-trap approach to target the αFR chimeric antigen receptor (CAR) as an exemplary antigen targeting receptor into the locus of an exemplary autophagy gene, autophagy-related gene 5 (ATG5), the inventors have disrupted autophagy while concurrently placing the CAR under control of the endogenous ATG5 promoter. Expression of the CAR is therefore upregulated in areas of hypoxia and stress, such as in the solid tumor microenvironment.

Without being bound by theory, it is believed that placing the antigen targeting receptor, e.g. CAR construct or engineered T-cell receptor (TCR) construct, under control of a promoter, such as the endogenous autophagy gene promoter, that induces expression in response to stress, means that the level of expression of the antigen targeting receptor (e.g. CAR or TCR) will be low in the periphery of the body, but will increase in the tumor microenvironment. This could potentially reduce the toxicity associated with a high dose of cells expressing the antigen targeting receptor, e.g. CAR-T-cells. As an example, ATG5 is constitutively expressed at a low level, but its level of expression increases in response to stress.

Further without being bound by theory, autophagy deficient mouse T-cells do not generate memory after in vivo infection (25). Without being bound by theory, this may be beneficial for the safety of treatment using the genetically engineered lymphocytes because after the modified cells reach the peak of response, they will die (i.e. because there is no memory formation), thereby clearing all of the genetically engineered lymphocytes from the subject. This provides a measure of safety in administering treatment to patients.

In one embodiment, the inventors have determined that Atg5 deficient mice have significantly enhanced anti-tumor activity against hormone insensitive prostate and estrogen positive breast tumor cell lines. This anti-tumor response is dependent on T-cells and can be fully replicated with animals defective in other Atg genes (e.g. Atg14, ATG16L1). When T-cells deficient in Atg5 were used in an adoptive T-cell therapy experiments, the inventors observed a therapeutic effect on tumors when compared to wild-type CD8+ T-cells. Thus, the loss of the T-cell intrinsic ATG5 or other autophagy genes has been demonstrated to result in enhanced anti-tumor immune responses.

Although there are defects of Atg5 loss in other immune subsets including antigen presentation cells, without being bound by theory, the specific loss of autophagy in T-cells may have several benefits for T-cell therapy. Atg5$^{-/-}$ T-cells from tumor bearing mice have been found to have high rates of glycolysis and low oxidative metabolism. This could be a metabolic advantage as increased glucose metabolism could make tumor infiltrating lymphocytes (TIL) more competitive for glucose. These metabolic changes are associated with Atg5$^{-/-}$ T-cells skewing towards effector cells with enhanced antigen specific T-cell responses. Without being bound by theory, the reduced proliferation of Atg5$^{-/-}$ T-cells may have unintended benefits. Since Atg5$^{-/-}$ T-cells are highly antigen specific, infusions would require fewer cells to achieve equivalent anti-tumor responses and recipient patients may not need to have lymphodepletion; a procedure that can have significant risk of adverse events. Another feature of Atg5$^{-/-}$ T-cells is the metabolic-dependent change in histone trimethylation at specific loci of immune response genes and increase in transcriptional expression of those targets.

Such benefits provided by the suppression of an autophagy gene can be extended to other lymphocytes and other cells involved in tumor killing. Examples of such cells include NK cells; various types of T-cells including CD34+, CD4+ or CD8+ T-cells, Treg cells, tissue-resident memory T cells (TRM cells), natural killer T (NKT) cells; B-cells, and the like. These cells act through a similar mechanism of recognizing an antigen such as a tumor-specific antigen on the surface of the tumor cell and acting to kill such tumor cell. Without being bound by theory, suppression of autophagy in such cells can enhance effector anti-tumor activity via metabolomics shifts to more glycolysis and greater IFNγ secretion. Also in the case of Treg cells, suppression of autophagy could also result in loss of suppressor function against effector T cells.

In some embodiments, an engineered lymphocyte such as a CAR T-cell having one or more disruptions in an autophagy gene or an otherwise suppressed autophagy gene is provided. In some embodiments, the disruptions in the autophagy gene suppress or ablate expression of the autophagy gene. In some embodiments, the disruption in the autophagy gene is provided using a 'knock-in' genetic engineering strategy. In some embodiments, the disruption in the autophagy gene is provided by using a knock-out genetic engineering strategy. In alternative embodiments, any desired strategy could be used to suppress one or more autophagy genes in the lymphocyte, e.g. a CAR T-cell. Likewise, any suitable genetic engineering strategy could be used to cause the engineered lymphocyte, e.g. CAR T-cell, to express the desired antigen targeting receptor, e.g. a chimeric antigen receptor (CAR) or an engineered T-cell receptor. For example, cells can be transduced with a viral vector (e.g. a lentiviral vector or a retroviral vector) to introduce a nucleotide construct encoding the CAR or engineered T-cell receptor into the cells. In some embodiments, a CRISPR-Cas9 gene editing system (which includes a CRISPR-Cas gene editing system using any suitable Cas protein, e.g. Cas9, Cas12a, or the like) or other similar gene editing technique can be used to disrupt the autophagy gene and/or introduce the antigen targeting receptor construct into the cell for expression. In some embodiments, a combination of different genetic engineering techniques could be used to both disrupt the autophagy gene and introduce the CAR construct into the T-cell for expression. In some embodiments, zinc-finger nucleases (ZFN), transcription activator-like effector nuclease (TALEN), Sleeping Beauty (SB), RNAi, meganucleases, megaTALs, or other gene knockout methods could be used to disrupt or suppress the autophagy gene.

In some embodiments, the engineered lymphocyte, e.g. CAR T-cell, expresses an antigen targeting receptor, e.g. a chimeric antigen receptor (CAR) or an endogenous or engineered T-cell receptor, that is selective for a tumor-specific antigen. In some embodiments, the tumor-specific antigen is the α-folate receptor (α-FR), which is an antigen that is highly expressed in certain kinds of cancer including ovarian cancer, breast cancer and lung cancer, but which is not expressed at a high level by normal cells. In some embodiments, the tumor-specific antigen is the folate receptor (FR), the β-folate receptor, the γ-folate receptor, CD19, CD20, BCMA, Her2, EGFRvIII, or prostate specific membrane antigen (PSMA). In some embodiments, the tumor-specific antigen is the folate receptor (FR), the α-folate receptor, the β-folate receptor, the γ-folate receptor, CD19, CD20, CD133, CD138, CEA, Claudin 18.2, EGFR, EGFRvIII, EphA2, EpCAM, GD2, GPC3, HER2, MSLN, MG7, MUC1, NY-ESO-1, LMP1, PSMA, Fra, NKG2DI, BCMA, IL13Ralpha2, LeY, CD70, B7-H3, ROR1, PSCA, or the like. In alternative embodiments, the tumor-specific antigen targeted by the antigen targeting receptor can be any desired tumor-specific antigen. A non-exhaustive list of exemplary tumor-specific antigens currently being evaluated for treatment of certain cancers is given in Table 1. In some embodiments, the cancer is B-cell acute lymphoblastic leukemia (B-ALL), chronic lymphocytic leukemia (CLL), B-cell lymphoma or other lymphoid malignancy, liver, pancreatic, brain, breast, ovarian, colorectal, acute myeloid leukemia (AML), multiple myeloma, lung, gastric, glioma, EGFR-positive solid tumor, glioblastoma, glioblastoma multiforme, stomach, nasopharyngeal, esophageal, prostate, neuroblastoma, hepatocellular, squamous cell lung, MSLN-positive solid tumor, non-small-cell lung (NSCLC), triple-negative breast cancer (TNBC), sarcoma, advanced solid tumor, renal cell, central nervous system, or an ROR1-positive malignancy.

TABLE 1

Exemplary tumor-specific antigens that can be targeted with antigen targeting receptor constructs such as a CAR.

| Target Antigen | Cancer(s) |
|---|---|
| CD19 | B-cell acute lymphoblastic leukemia (B-ALL), chronic lymphocytic leukemia (CLL), and B-cell lymphoma |
| CD20 | lymphoid malignancies |
| CD133 | liver, pancreatic, brain, breast, ovarian, colorectal, acute myeloid leukemia (AML) |
| CD138 | multiple myeloma |
| CEA | lung, colorectal, gastric, breast, pancreatic |
| Claudin 18.2 | gastric, pancreatic |
| EGFR | EGFR-positive solid tumors, glioma, colorectal |
| EGFRvIII | glioblastoma multiforme |
| EphA2 | malignant glioma |
| EpCAM | liver, stomach, nasopharynx, colon, esophageal, pancreatic, prostate, gastric, hepatic, recurrent breast |

TABLE 1-continued

Exemplary tumor-specific antigens that can be targeted with antigen targeting receptor constructs such as a CAR.

| Target Antigen | Cancer(s) |
|---|---|
| GD2 | neuroblastoma |
| GPC3 | hepatocellular, liver, squamous cell lung |
| HER2 | breast, ovarian, lung, gastric, colorectal, glioma, pancreatic |
| MSLN | pancreatic, MSLN-positive solid tumors |
| MG7 | liver |
| MUC1 | glioma, colorectal, gastric, hepatocellular, non-small-cell lung carcinoma (NSCLC), pancreatic, breast, ovarian |
| NY-ESO-1 | NSCLC |
| LMP1 | nasopharyngeal |
| PSMA | prostate |
| Fra | ovarian |
| NKG2DL | colorectal, triple-negative breast cancer (TNBC), sarcoma |
| BCMA | multiple myeloma |
| IL13Ralpha2 | glioblastoma |
| LeY | advanced solid tumors |
| CD70 | pancreatic, renal cell, breast |
| B7-H3 | central nervous system (CNS), glioma |
| ROR1 | ROR1+ malignancies |
| PSCA | prostate |

In some embodiments, the antigen targeting receptor, e.g. CAR construct or endogenous or engineered T-cell receptor (TCR) construct, is inserted at the locus of the autophagy gene that is to be suppressed using a knock-in strategy. This places the antigen targeting receptor, e.g. CAR construct or TCR construct, under control of the endogenous promoter of the autophagy gene. In some embodiments, the antigen targeting receptor, e.g. CAR construct or TCR construct, is inserted in the lymphocyte's (e.g. T-cell) genome at a locus other than the autophagy gene that is to be suppressed. In some such embodiments, expression of the antigen targeting receptor, e.g. CAR construct or TCR construct, is controlled by a heterologous promoter. In some embodiments, the antigen targeting receptor, e.g. CAR construct or TCR construct, is inserted together with a desired exogenous promoter to control expression of the antigen targeting receptor, e.g. CAR or TCR, by the lymphocyte (e.g. T-cell) under the control of an exogenous promoter. In some embodiments, the antigen targeting receptor (e.g. CAR or TCR construct) is placed under control of a promoter that increases expression of the antigen targeting receptor in response to stress. In some embodiments, the promoter that increases expression of the antigen targeting receptor in response to stress is a promoter of an autophagy gene.

In some embodiments, rather than expressing a CAR, the lymphocyte is engineered to express an endogenous or engineered T-cell receptor as the antigen targeting receptor. TCR-engineered T-cells are currently being developed for use in various types of immunotherapy, including the treatment of solid tumors, and can be used in a manner similar to CAR-T cells to specifically target and kill cells expressing a particular antigen, e.g. a tumor-specific antigen.

In some embodiments, the autophagy gene (ATG) that is suppressed in the lymphocyte is any gene that is now known or is later discovered to be essential for autophagy. In some embodiments, the autophagy gene is one or more of ATG1, ATG4, ATG5, ATG7, ATG8, ATG13, ATG18, ATG16L1, and GABARAP. In some embodiments, the autophagy gene is one or more of ULK1, ULK2, ULK3, FIP200, Vps34, Beclin-1, p150, UVRAG, ATG1, ATG4, ATG5, ATG7, ATG8, ATG9, ATG10, ATG12, ATG13, ATG14L, ATG16L, ATG16L1, ATG18, VMP1, GABARAP, or the like.

In some embodiments, the CAR construct has a targeting moiety, a transmembrane domain and a CD3ζ intracellular domain. In some embodiments, the targeting moiety is an antigen-binding fragment of an antibody. In some embodiments, the targeting moiety is an ScFV of an antibody. In alternative embodiments, any CAR construct now known or later developed could be used.

In alternative embodiments, an engineered T-cell receptor is used as the antigen targeting receptor. An example of an engineered T-cell receptor has an α chain and a β chain, each containing a variable domain (v) and a constant domain (c), as well as a transmembrane domain and 6 CD3 chains for T-cell activation. In alternative embodiments, any T-cell receptor construct now known or later developed could be used.

An example embodiment of a CAR construct 30 for use in some embodiments is shown in FIG. 1. The CAR construct has a targeting moiety 32, e.g. a suitable ScFV that targets a desired tumor-specific antigen, a transmembrane domain 34, and a CD3ζ intracellular domain 38. In some embodiments, CAR construct 30 can have other domains such as a suitable co-stimulatory domain 36 (e.g. CD27, CD28, 4-1BB, ICOS, OX40, MYD88, IL1R1, CD70, or the like), or other domains intended to enhance the characteristics of the CAR construct.

Figure 2:
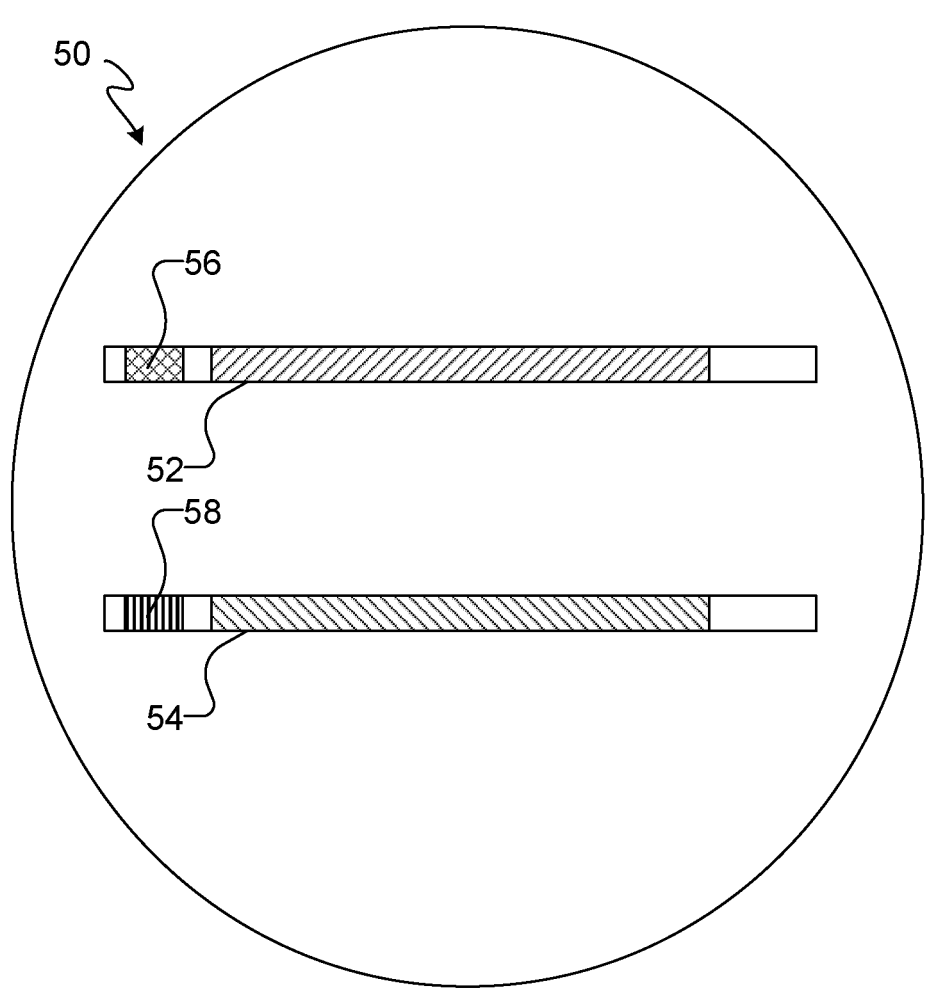
FIG. 2 is a schematic diagram of an embodiment in which the DNA encoding the CAR has been inserted at a locus of the genome of the cytotoxic lymphocyte cell at a location other than the locus of the autophagy gene that has been disrupted.

FIG. 2 shows schematically an example embodiment of an engineered lymphocyte 50. Engineered lymphocyte 50 has been genetically modified to suppress one or more genes essential for autophagy at a locus 52 of the genomic DNA of the lymphocyte. The gene essential for autophagy is under control of an endogenous promoter 56. Engineered lymphocyte 50 has also been genetically modified to express a desired antigen targeting receptor construct at a locus 54 of the genomic DNA of the lymphocyte which is different from locus 52. The expression of the antigen targeting receptor construct from locus 54 is under control of a promoter 58, which can be an endogenous promoter in some embodiments or a heterologous promoter in some embodiments.

Figure 3:
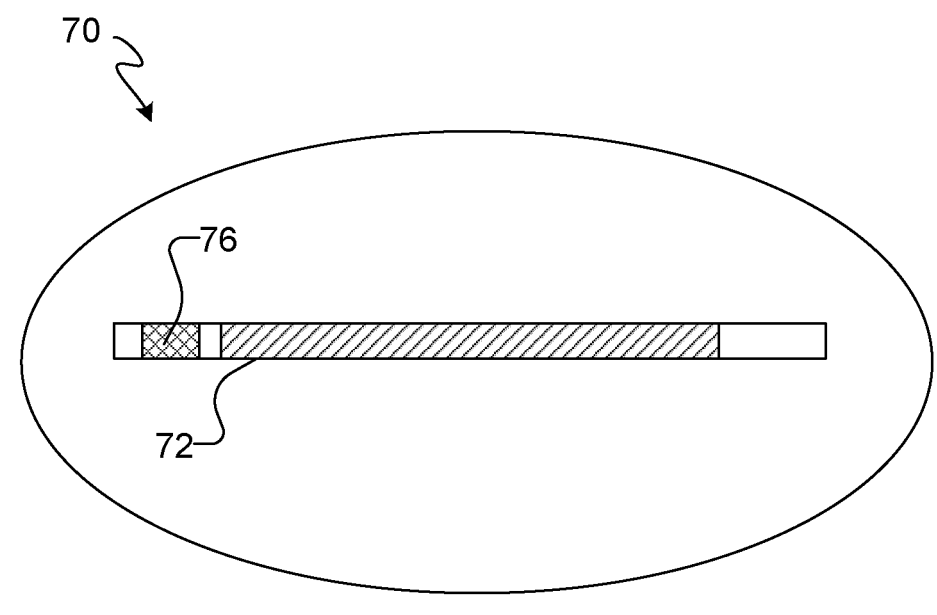
FIG. 3 is a schematic diagram of an embodiment in which the DNA encoding the CAR has been inserted at the locus of an autophagy gene within the genome of a cytotoxic lymphocyte cell.

FIG. 3 shows schematically an example embodiment of an engineered lymphocyte 70. Engineered lymphocyte 70 has been genetically modified to both suppress one or more genes essential for autophagy and express a desired antigen targeting receptor construct at a locus 72 of the genomic DNA of the lymphocyte. For example, a knock-in strategy can be employed to both disrupt the gene essential for autophagy and insert the desired antigen targeting receptor construct at locus 72 of the genomic DNA of the lymphocyte. In this embodiment, expression of the desired antigen targeting receptor construct from locus 72 is under control of the endogenous promoter 76 of the gene essential for autophagy.

Figure 4:
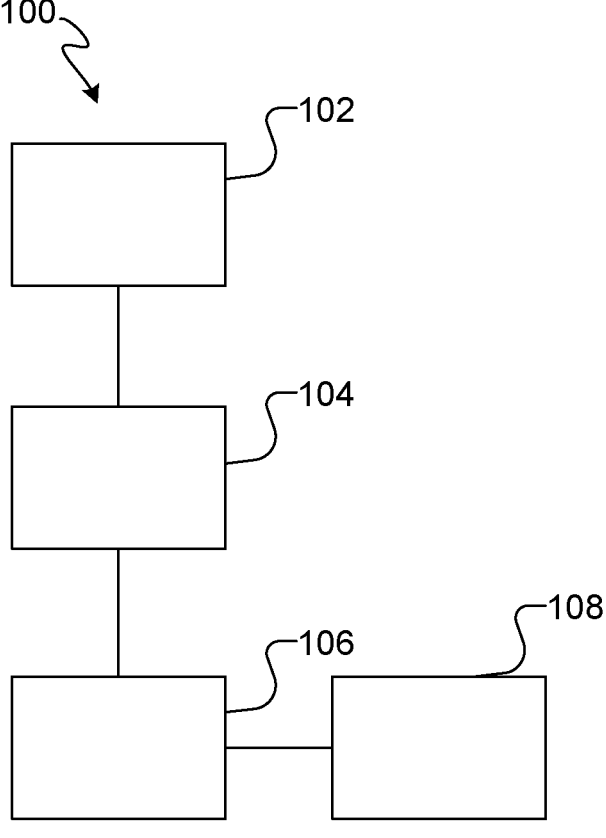
FIG. 4 shows an example embodiment of a method for producing genetically engineered lymphocytes for use in immunotherapy.

Engineered lymphocytes 50, 70, or modified lymphocytes, including engineered T-cells, according to any other embodiment, can be made via any suitable genetic engineering technique now known or later made available to one skilled in the art. In one example embodiment shown in FIG. 4, a method 100 of creating modified lymphocytes such as T-cells using a gene editing strategy to insert the desired antigen targeting receptor construct at the locus of the autophagy gene to be disrupted is shown. At step 102, the desired lymphocytes such as T-cells are obtained from a source of cells. The source of the cells may be any suitable source, for example, the subject to whom the immunotherapeutic lymphocytes are to be administered, a healthy donor, a pluripotent stem cell line, or the like. In some embodiments, the lymphocytes are autologous cells, i.e. the lymphocytes are acquired from the subject to be treated. In some embodiments, the lymphocytes are allogenic, i.e. obtained from source of cells other than the subject to be treated, such as a healthy donor or a cell line such as induced pluripotent stem cells. Any source of lymphocytes now known or later discovered can be used in certain embodiments.

At step 104, the lymphocytes are genetically engineered to insert DNA encoding the antigen targeting receptor construct in the genomic DNA of the lymphocytes and suppress the function of at least one autophagy gene. In some embodiments, step 104 is carried out using a CRISPR-Cas gene editing strategy, by devising suitable sgRNA to insert the antigen targeting receptor construct at an appropriate location within an autophagy gene so that the antigen targeting receptor construct can be inserted and the autophagy gene simultaneously suppressed using a knock-in strategy. The sgRNA, DNA encoding the antigen targeting receptor construct, and a Cas protein such as Cas9 are delivered to the lymphocyte in any suitable manner, for example via electroporation or chemical transfection techniques, or other suitable techniques as appropriate, for example using a delivery system based on a lentivirus, adenovirus, or adeno-associated virus.

At step 106, the genetically engineered lymphocytes in which the antigen targeting receptor construct has been successfully inserted at the correct locus are expanded. At step 108, the engineered lymphocytes are introduced into the subject as an immunotherapeutic.

Figures 5, 6:
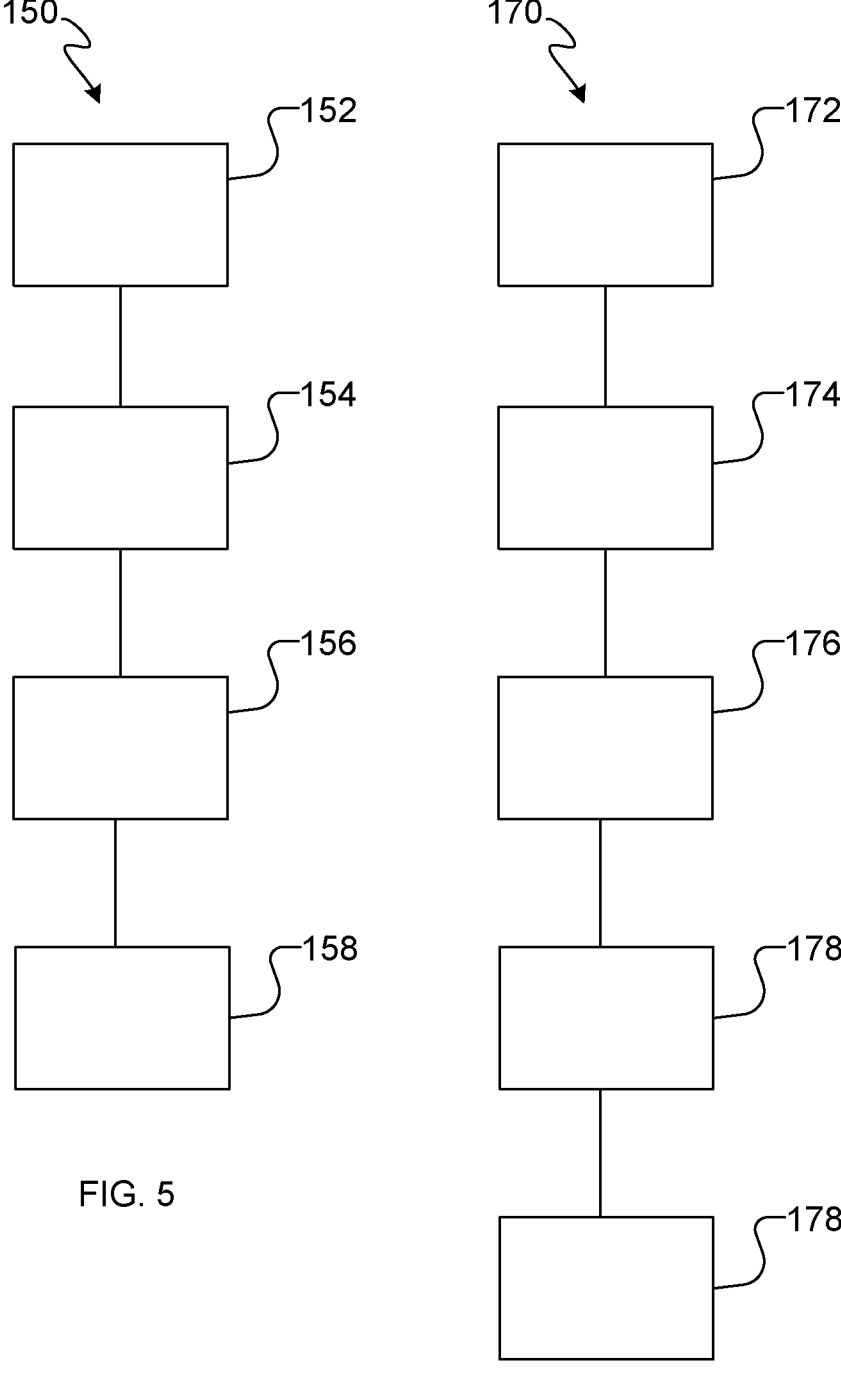
FIG. 5 shows another example embodiment of a method for producing genetically engineered lymphocytes for use in immunotherapy.
FIG. 6 shows another example embodiment of a method for producing genetically engineered lymphocytes for use in immunotherapy.

FIG. 5 shows an alternative embodiment of a method 150 of creating modified lymphocytes such as T-cells for immunotherapy. At step 152, lymphocytes are obtained from a source of cells in a similar manner as described for step 102. At step 154, the lymphocytes, e.g. T-cells, are genetically engineered in any suitable manner to suppress one or more autophagy genes. Examples of techniques that can be used to suppress the autophagy gene include ablation via gene knock out techniques using CRISPR-Cas, TALEN, ZFN, SB, meganucleases, megaTALs, or suppression via gene knockdown via RNAi, or other suitable techniques.

At step 156, in some embodiments, the genetically engineered lymphocytes in which the autophagy gene has been suppressed are expanded. At step 158, the lymphocytes are introduced into the subject as an immunotherapeutic.

FIG. 6 shows an alternative embodiment of a method 170 of creating modified lymphocytes such as T-cells for immunotherapy. Steps 172 and 174 are carried out in like manner to steps 152 and 154 of method 150 to produce lymphocytes, e.g. T-cells, that are genetically engineered to suppress one or more autophagy genes. At step 176, the lymphocytes, e.g. T-cells, are further genetically engineered in any suitable manner to express a desired antigen targeting receptor, such as a CAR construct or engineered T-cell receptor construct. Examples of techniques that may be used to engineer the lymphocytes, e.g. T-cells, to express a desired antigen targeting receptor such as a CAR construct or engineered T-cell receptor include CRISPR-Cas editing systems or transduction with a suitable lentiviral or retroviral vector. At step 178, the lymphocytes, e.g. T-cells, that have been genetically engineered to have both a suppressed autophagy gene and to express the desired antigen targeting receptor, e.g. CAR construct or engineered T-cell receptor, are expanded. At step 180, the expanded cells are introduced into the subject as an immunotherapeutic. In alternative embodiments, the order in which steps 174 and 176 are carried out can be reversed, that is the lymphocytes, e.g. T-cells, can be first engineered to express the desired antigen targeting receptor, e.g. CAR construct or engineered T-cell receptor, and then engineered to suppress one or more autophagy genes.

In some embodiments, the genetically engineered lymphocytes, e.g. T-cells, are used as an immunotherapeutic to treat cancer. In some embodiments, the cancer is ovarian cancer, breast cancer, or lung cancer. In some embodiments, the cancer is B-cell acute lymphoblastic leukemia (B-ALL), chronic lymphocytic leukemia (CLL), B-cell lymphoma or other lymphoid malignancy, liver, pancreatic, brain, breast, ovarian, colorectal, acute myeloid leukemia (AML), multiple myeloma, lung, gastric, glioma, EGFR-positive solid tumor, glioblastoma, glioblastoma multiforme, stomach, nasopharyngeal, esophageal, prostate, neuroblastoma, hepatocellular, squamous cell lung, MSLN-positive solid tumor, non-small-cell lung (NSCLC), triple-negative breast cancer (TNBC), sarcoma, advanced solid tumor, renal cell, central nervous system, or an ROR1-positive malignancy. The genetically engineered lymphocytes, e.g. T-cells, can be administered to the subject in any suitable manner, for example via intravenous diffusion.

In some embodiments in which a CRISPR-Cas strategy is used to introduce the antigen targeting receptor construct into the lymphocyte for expression, the CRISPR-Cas strategy is also used to simultaneously suppress expression of an autophagy gene. Persons skilled in the art can develop appropriate single guide RNAs (sgRNAs) to effect the insertion of the antigen targeting receptor, e.g. CAR, at a desired location in the genome of the lymphocyte. In some embodiments, the CRISPR-Cas strategy is used to insert the antigen targeting receptor, e.g. CAR, within the locus of the ATG5 gene in the genome of the lymphocyte. In some embodiments, the CRISPR-Cas strategy is used to insert the antigen targeting receptor, e.g. CAR, within intron 2 of the ATG5 gene. In some embodiments, the CRISPR-Cas strategy is used to disrupt the ATG5 gene at exon 4 or exon 5 of the ATG5 gene while the antigen targeting receptor is inserted at a different locus within the genome, for example using transduction with an appropriate lentiviral, retroviral or adeno-associated viral vector. In some embodiments, the CRISPR-Cas strategy is used to insert DNA encoding an engineered T-cell receptor rather than DNA encoding a CAR.

In one example embodiment, the sgRNA used to target intron 2 of ATG5 has the sequence of one of SEQ ID NOs:1-7 listed in Table 2. In one example embodiment, the sgRNA used to target exon 4 of ATG5 has the sequence of SEQ ID NO:24. In one example embodiment, the sgRNA used to target exon 5 of ATG5 has the sequence of SEQ ID NO:25.

In one example embodiment, the nucleotide construct used to insert the CAR into the T-cells has one of SEQ ID NO:8 or SEQ ID NO:9.

Examples

Certain embodiments are further described with reference to the following examples, which are intended to be illustrative and not limiting in nature. While the following examples demonstrate the suppression of an autophagy gene and expression of a CAR in T-cells, the techniques described below are equally applicable to conduct the genetic engineering of other types of lymphocytes to suppress expression of an autophagy gene and express a desired CAR or engineered T-cell receptor.

The inventors designed and tested several single guide RNAs (sgRNAs) targeted to the locus of autophagy-related gene 5 (ATG5), and quantified indel formation by sequencing and mismatch cleavage assay. The inventors optimized conditions for homology-directed repair (HDR) in K562 cells using a fluorescent reporter construct. Out-out polymerase chain reaction (PCR) and Western blot were used to evaluate construct integration and autophagy activity. To identify transfection parameters that would yield optimal editing and expansion in human T-cells, the inventors then performed a series of electroporations with sgRNA and recombinant Cas9 protein. The inventors used these electroporation parameters in combination with adeno-associated virus (AAV) vectors to target the αFR chimeric receptor into the locus of ATG5 in healthy donor T-cells.

The inventors observed loss of functional autophagy in clones with donor integration. Furthermore, the inventors confirmed that these results were due to on-target editing by delivering ATG5 cDNA to an intergenic locus and restoring autophagy function. After screening multiple transfection parameters (cell density, RNP concentration, electroporation pulse code, and addition of an anionic polymer) the inventors identified a set of conditions for RNP delivery that yielded upwards of 80% indel formation in healthy donor T-cells. Using these parameters in conjunction with an AAV vector encoding the αFR CAR, the inventors successfully generated 24.1% ATG5$^{-/-}$ αFR-CAR-T-cells by CRISPR-mediated homology directed repair.

Figure 7:
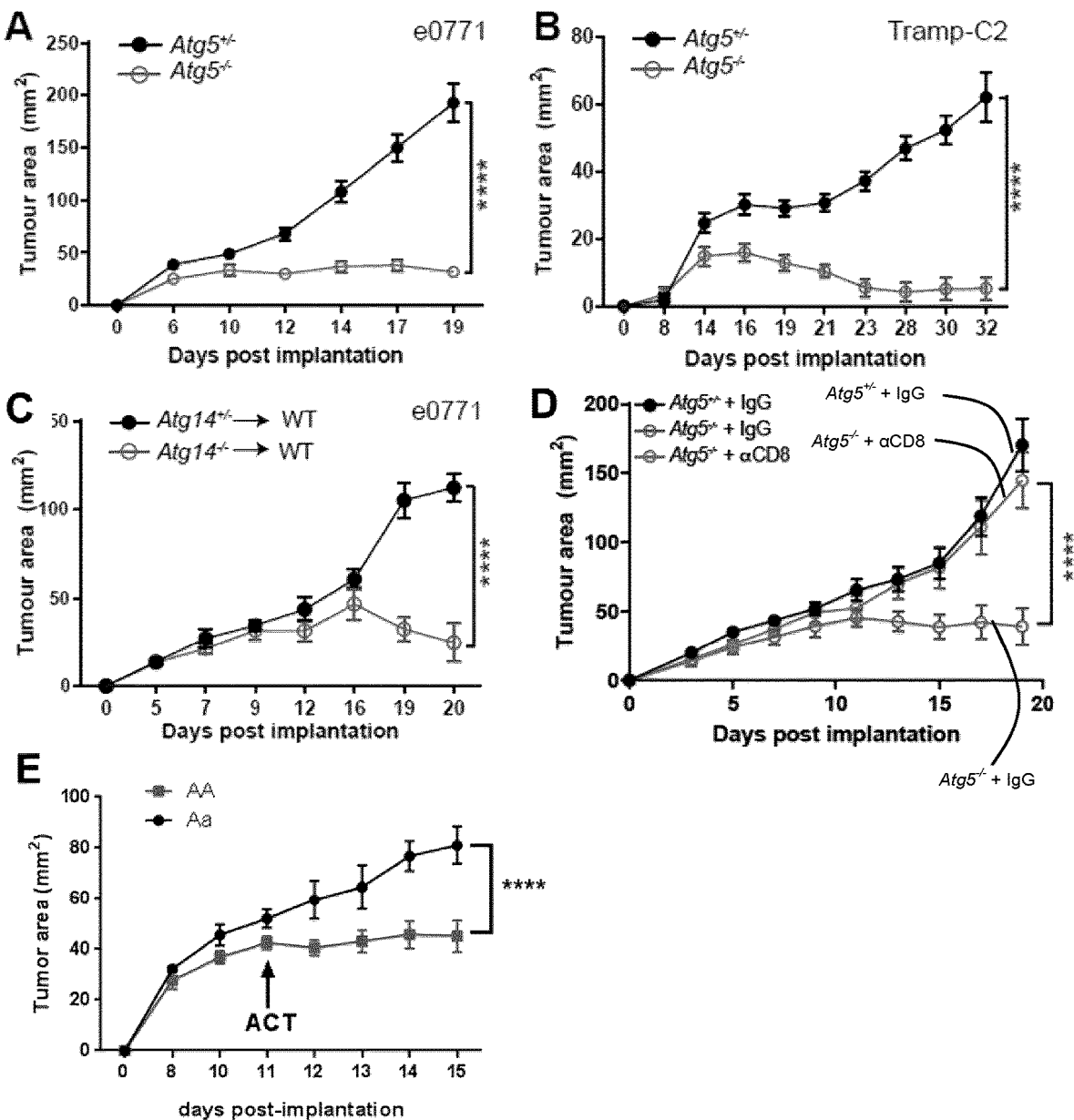
FIG. 7, Panels A-E, show the results of an example demonstrating that autophagy enhances anti-tumor immunity and that this effect is dependent on T-cells.

FIG. 7 shows the results of experiments demonstrating that deletion of autophagy enhances anti-tumor immunity and is dependent on T-cells. The inventors made an inducible Cre-ERT2 mouse to delete Atg5 in all tissues upon tamoxifen injection. 4 days post tamoxifen treatment, e0771 breast (Panel A) or TRAMP-C2 prostate (Panel B) tumor cell lines were injected subcutaneously and tumor volume measured over time. n=12-13 mice per experimental group.

Panel C shows using a different autophagy gene, Atg14, that Atg14-dependent enhancement of anti-tumor immunity is cell-intrinsic to the T-cells. The inventors performed bone-marrow chimera experiments where wild type (WT) mice were reconstituted with Atg5$^{-/-}$ or Atg5$^{+/-}$ bone marrow (BM). Atg5$^{-/-}$ BMC mice show enhanced tumor rejection. n=10 mice per experimental group. Similar experiments were performed using Atg14$^{-/-}$ or Atg14$^{+/-}$ BM (data not shown).

Panel D shows that antibody depletion of CD8+ T-cells (achieved using an anti-CD8 antibody) results in loss of tumor control in Atg5−/− mice. n=4-7 mice per experimental group. **p<0.0001, two-way ANOVA. Error bars indicate +/−SEM. Panel E shows the adoptive transfer of naïve CD8+Atg5 deficient (AA) or Atg5 wildtype (Aa) T-cells into EG7 tumor bearing mice. Tumors were implanted and donor T-cells transferred on Day 11 (ACT). ** p<0.0001, Student's t test. Error bars indicated +/−SD.

Figure 8:
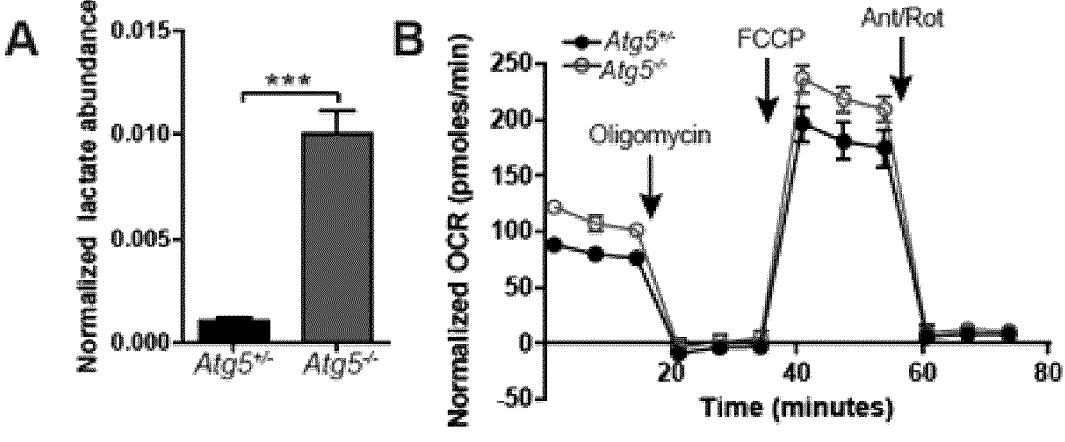
FIG. 8, Panels A-K, shows the metabolomics of Atg5$^{-/-}$ CD8+ T-cells.
Figure 8:
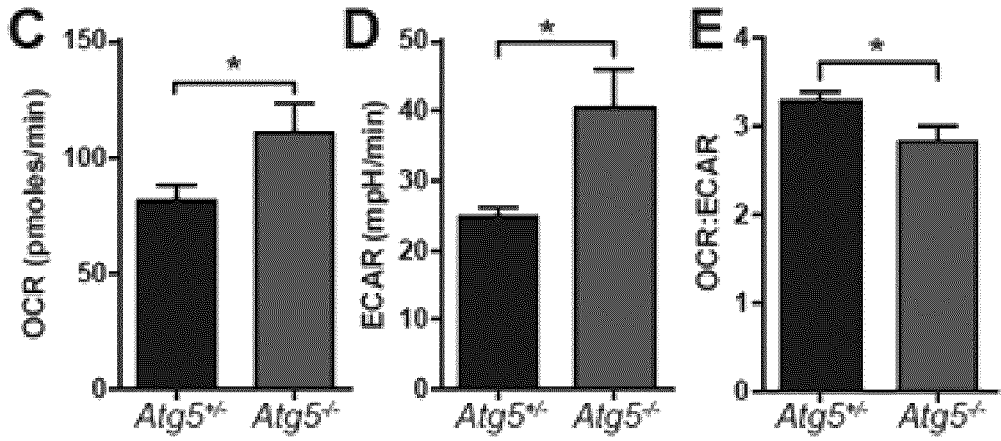
Figure 8:
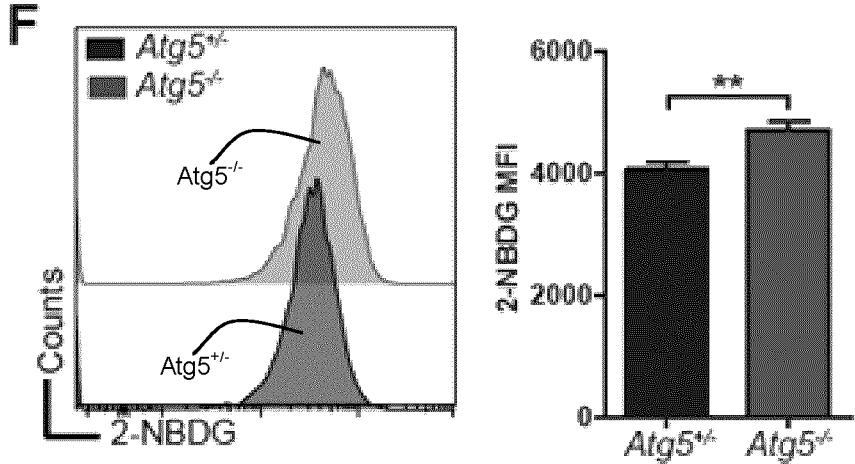
Figure 8:
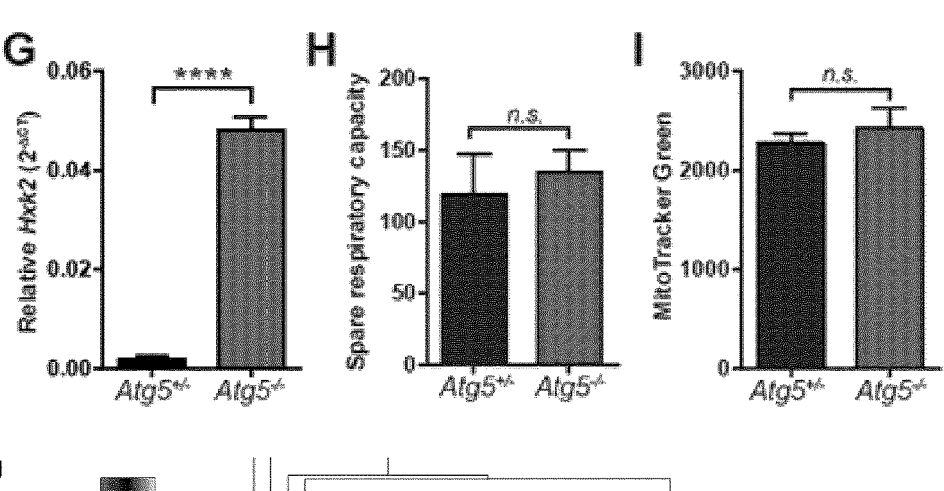
Figure 8:
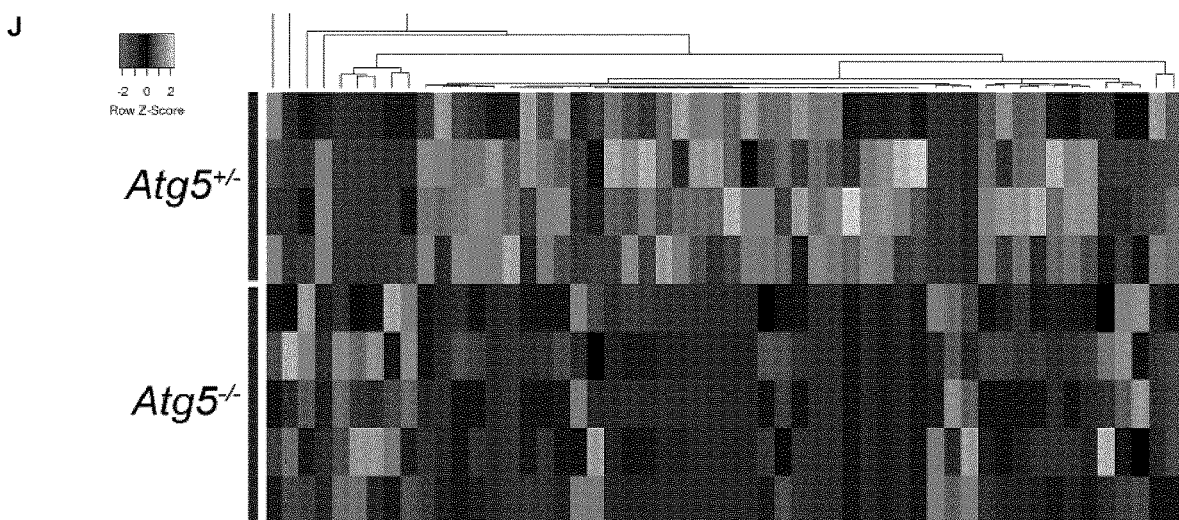
Figure 8:
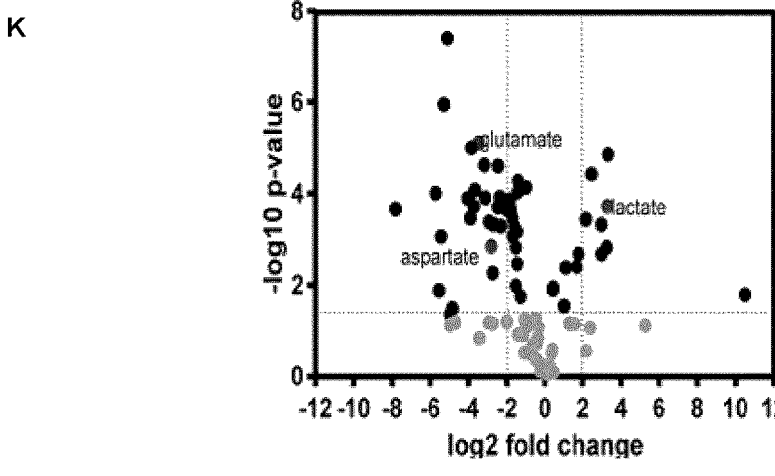

FIG. 8 shows the results of experiments evaluating the metabolomics of Atg5$^{-/-}$ CD8+ T-cells and showing that Atg5$^{-/-}$ CD8+ T-cells are more glycolytic. *p<0.01, p<0.01, *p<0.001, ****p<0.001. Panel A shows the relative lactate levels identified by metabolomics. The error bars indicate +/−SD. Panel B shows oxygen consumption rate (OCR) results for CD8+ T-cells that were isolated from spleens of e0771 tumour bearing mice and were subjected to Seahorse Bioanalyzer in the presence or absence of oligomycin, FCCP and Antimycin/Rotenone (Ant/Rot). Data was normalized to protein concentration. Error bars indicate +/−SEM. OCR (Panel C), extracellular acidification rate (ECAR) (Panel D) and OCR:ECAR (Panel E) ratio of Atg5$^{+/-}$ and Atg5$^{-/-}$ CD8+ T-cells was examined at basal levels. Atg5$^{-/-}$ T-cells exhibit an increased oxygen consumption rate and increased extracellular acidification rate.

Panel F on the left shows a representative flow cytometry plot showing fluorescent glucose analog 2-NBDG uptake in splenic Atg5$^{+/-}$ (lower trace) and Atg5$^{-/-}$ (upper trace) CD8+ T-cells from e0771 tumour bearing mice. Graph on the right half of Panel F represents the mean fluorescence intensity (MFI) of 2-NBDG+/−SEM, with Atg5$^{-/-}$ exhibiting considerably higher fluorescence and therefore higher glucose uptake.

Panel G shows quantitative RT-PCR of Hxk2 expression in Atg5$^{+/-}$ and Atg5$^{-/-}$ CD8+ T-cells. Results are relative to Actb. Data are expressed as average+/−SEM. Panel H shows spare respiratory capacity, indicated by baseline OCR subtracted from maximal OCR, and Panel I shows mitochondrial mass as measured by MitoTracker Green, as determined in Atg5$^{+/-}$ and Atg5$^{-/-}$ CD8+ T-cells isolated from e0771 tumour bearing mice. Data are expressed as average+/−SEM. n=4-5 mice per group.

Panel J shows T metabolomics analysis for cells from tumor bearing Atg5$^{-/-}$ (n=5) or Atg5$^{+/-}$ (n=4) mice that were harvested on day 14 post-tumor implantation and (10,000 cells). Panel K shows a volcano plot analysis which revealed a significant increase in glycolysis (e.g. lactate) with concomitant reductions in oxidative metabolism (e.g. glutamate, aspartate).

Figure 9:
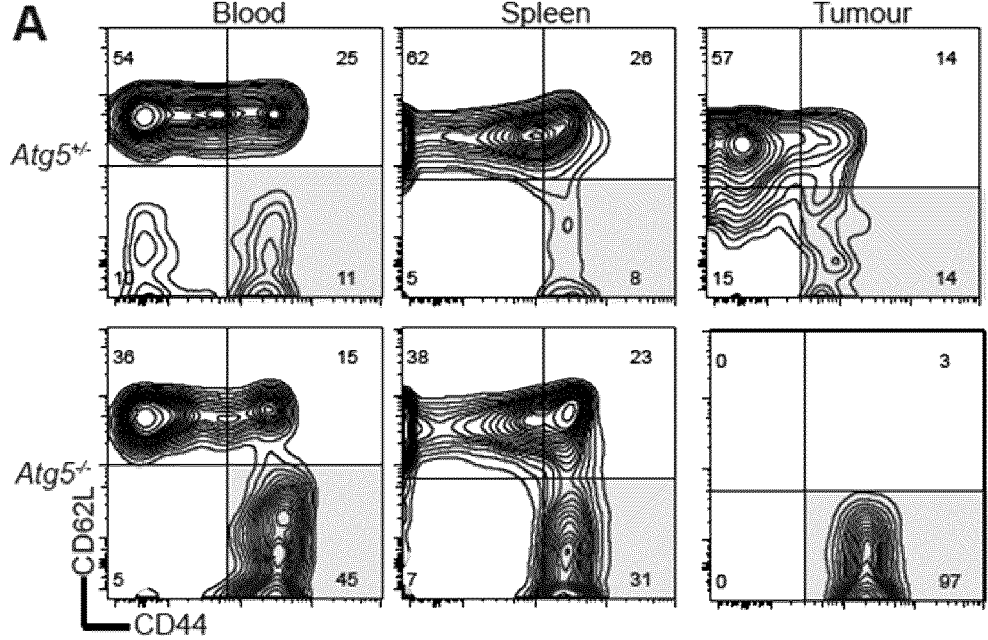
FIG. 9, Panels A and B, show the results of an example demonstrating that Atg5 deficiency leads to increased effector memory CD8+ T-cells.
Figure 9:
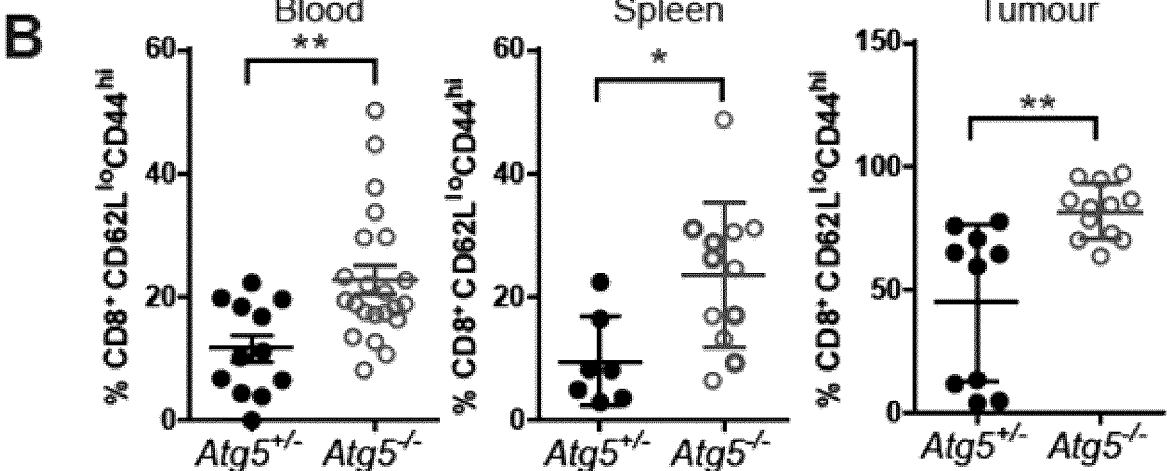

FIG. 9 shows the results of experiments demonstrating that Atg5 deficiency leads to increased effector memory CD8+ T-cells. Panel A shows representative flow cytometry plots showing naïve (CD62LhiCD44lo), central memory (CD62LhiCD44hi) and effector memory (CD62LloCD44hi) CD8+ T-cells isolated from blood (left side), spleen (centre) and tumours (right side) of e0771 tumour bearing mice. Panel B shows the percentages of CD62LloCD44hi effector memory CD8+ T-cells in blood, spleen and tumours from e0771 tumour bearing mice. * p<0.05, ** p<0.01.

Figure 10:
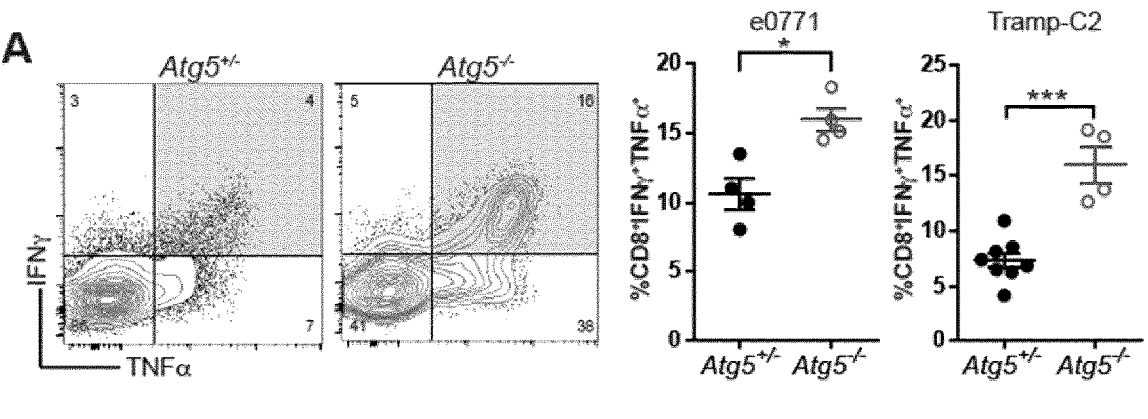
FIG. 10, Panels A-E, show the results of an example demonstrating that Atg5$^{-/-}$ CD8+ T-cells have enhanced anti-tumor function.
Figure 10:
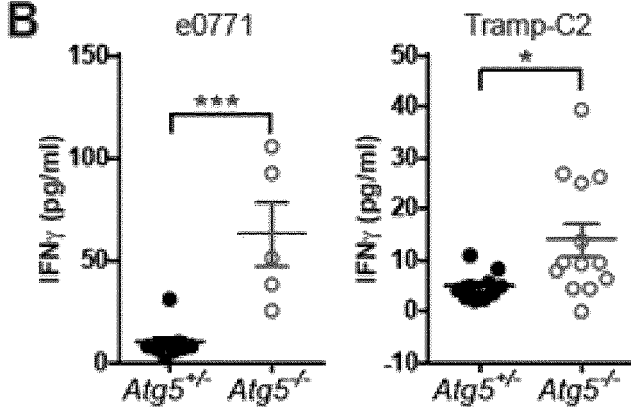
Figure 10:
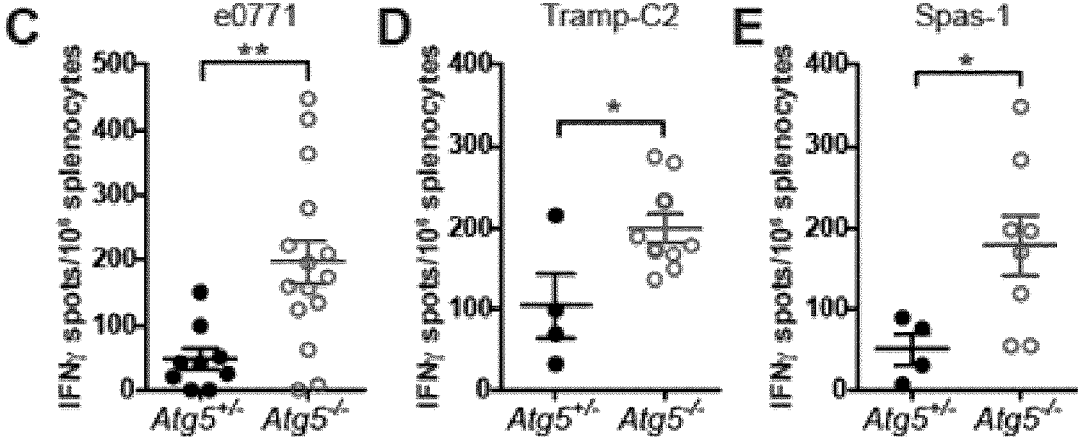

With reference to FIG. 10, the inventors have carried out experiments demonstrating that Atg5$^{-/-}$ CD8+ T-cells have enhanced anti-tumor function. The left two images of Panel A show representative flow cytometry plots showing IFNγ and TNFα expression following PMA/ionomycin stimulation of Atg5$^{+/-}$ and Atg5$^{-/-}$ CD8+ T-cells from Tramp-C2 tumour bearing mice. The graphs shown to the right of Panel A represent the percentage of IFNγ+TNFα+CD8+ T-cells in e0771 and Tramp-C2 tumour bearing mice+/−SEM, with the percentage being higher for Atg5$^{-/-}$ cells. Panel B shows serum from e0771 or Tramp-C2 tumour bearing mice as analyzed by ELISA. Graphs represent the average+/−SEM. Levels of IFNγ were higher for Atg5$^{-/-}$ mice. Panel C shows splenocytes harvested from Atg5$^{+/-}$ and Atg5$^{-/-}$ e0771 tumour bearing mice which were stimulated with e0771 cells, and IFNγ ELISPOT assays were performed. Data are expressed as average+/−SEM. In another experiment, splenocytes harvested from Tramp-C2 tumour bearing mice were stimulated with Tramp-C2 cells (Panel D) or Spas-1 peptide (Panel E), and IFNγ ELISPOT assays were performed. Data are expressed as average+/−SEM. *p<0.05, p<0.01, *p<0.001, ****p<0.0001. Increased TNFα and IFNγ are observed in Atg5' T-cells.

Figure 11:
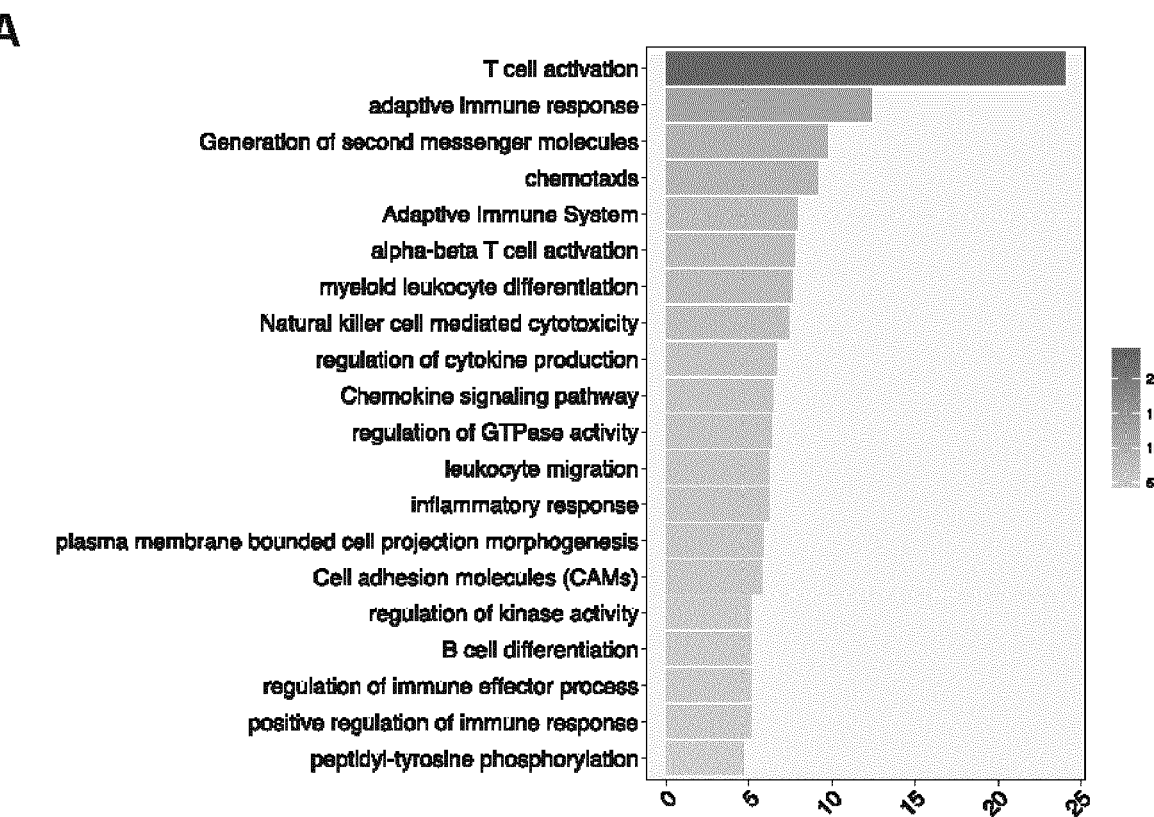
FIG. 11, Panels A-J, show the results of experiments demonstrating that Atg5$^{-/-}$ T-cells have changes in histone trimethylation and increase in methylation at immune response gene loci.
Figure 11:
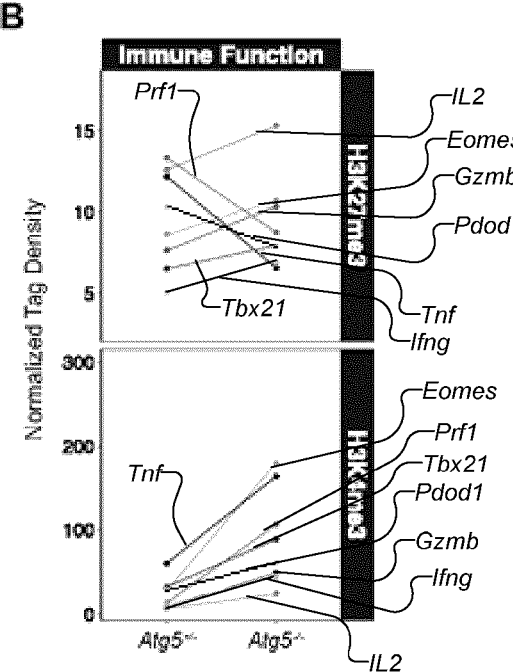
Figure 11:
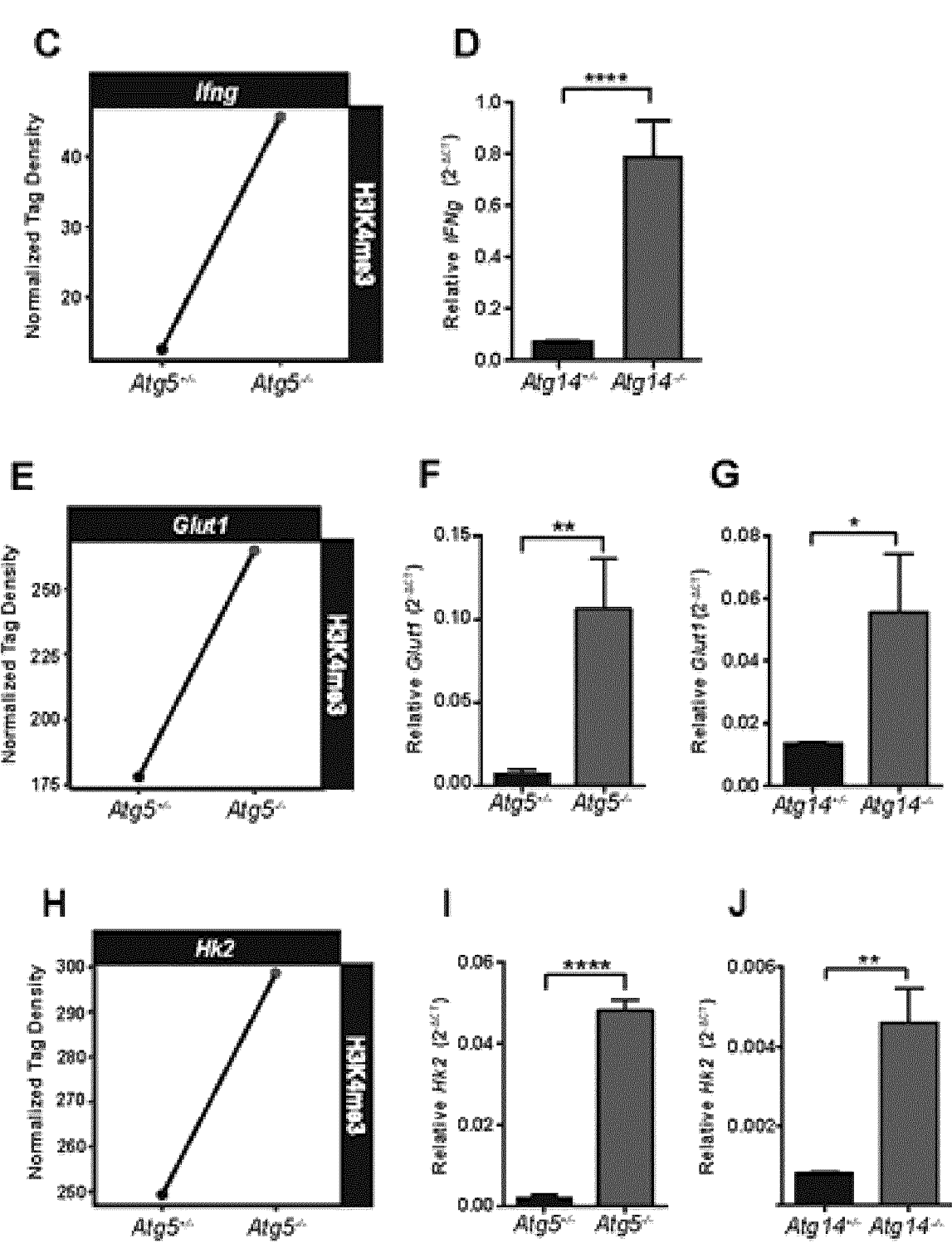

With reference to FIG. 11, the inventors conducted experiments to show that Atg5$^{-/-}$ T-cells have changes in histone trimethylation and increase in methylation at immune response gene loci. Panel A shows pathway and gene ontology analysis of H3K4me3-marked promoters unique to Atg5$^{-/-}$ versus Atg5$^{+/-}$ CD8+ T-cells are strongly enriched in genes related to T-cell activation and adaptive immunity (Benjamini q value <10e-12). Panel B shows differential normalized tagged density of H3K27me3 and H3K4m3 in a subset of immune response genes. Panels C and D show ChIP-Seq on Atg5$^{+/-}$ and Atg5$^{-/-}$ CD8+ T-cells for H3K4me3 for Ifng. Panel C shows normalized tag density of Ifng in knockout or control CD8+ T-cells. Panel D shows quantitative RT-PCR of Ifng expression in Atg14$^{+/-}$ and Atg14$^{-/-}$ CD8+ T-cells. Results are relative to Actb. Data are expressed as average+/−SEM of a triplicate experiment with at least 2 mice per group. Panels E-G show ChIP-Seq on Atg5$^{+/-}$ and Atg5$^{-/-}$ CD8+ T-cells for H3K4me3 for Glut1. Panel E shows normalized tag density of Glut1 in knockout or control CD8+ T-cells. Panel F shows quantitative RT-PCR of Glut1 expression in Atg5$^{+/-}$ and Atg5$^{-/-}$ CD8+ T-cells or (Panel G) Atg14$^{+/-}$ and Atg14$^{-/-}$ CD8+ T-cells. Results are relative to Actb. Data are expressed as average+/−SEM of a triplicate experiment with at least 2 mice per group. Panels H-J show ChIP-Seq on Atg5$^{+/-}$ and Atg5$^{-/-}$ CD8+ T-cells for H3K4me3 for Hk2. Panel H shows normalized tag density of Hk2 in knockout or control CD8+ T-cells. Panel I shows quantitative RT-PCR of Hk2 expression in Atg5$^{+/-}$ and Atg5$^{-/-}$ CD8+ T-cells or (Panel J) Atg14$^{+/-}$ and Atg14$^{-/-}$ CD8+ T-cells. Results are relative to Actb. Data are expressed as average+/−SEM of a triplicate experiment with at least 2-3 mice per group. *p<0.01, p<0.01, **p<0.001, n.s. not significant.

Figure 12:
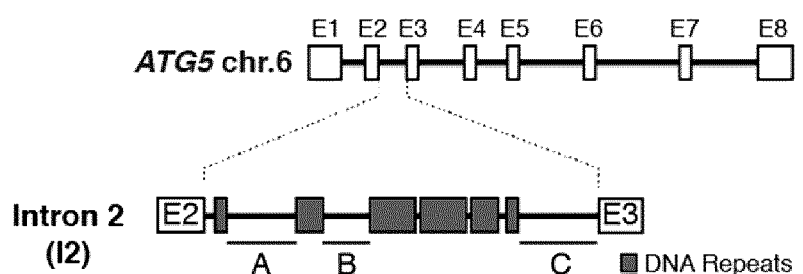
FIG. 12, Panels A-I, show a CRISPR-Cas9 strategy and validation of its successful implementation for gene-editing at the ATG5 locus to target the CAR to the ATG5 locus with a concomitant functional knock out of ATG5 and targeted integration of a gene trap vector using CRISPR-Cas9.
Figure 12:
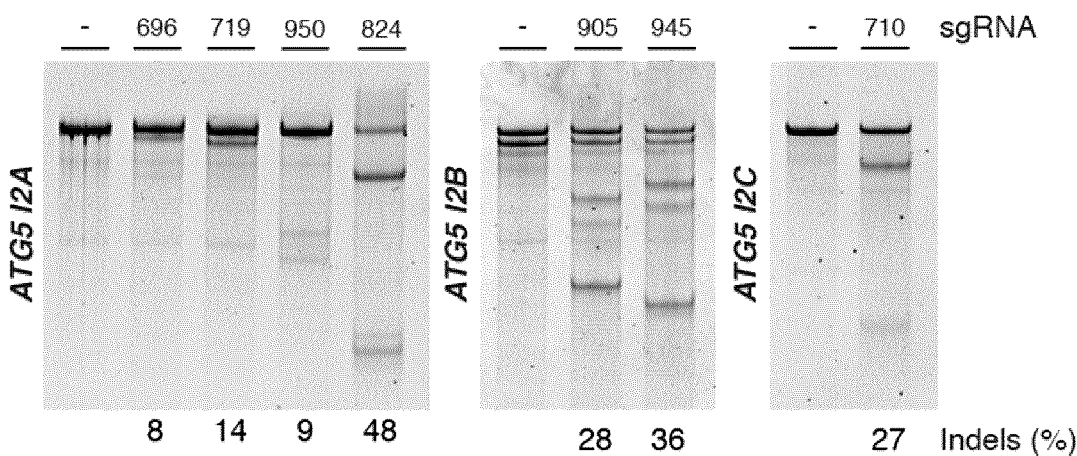
Figure 12:
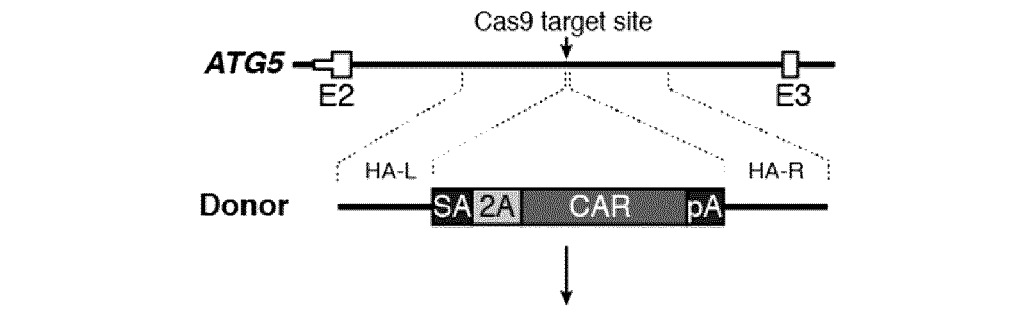
Figure 12:
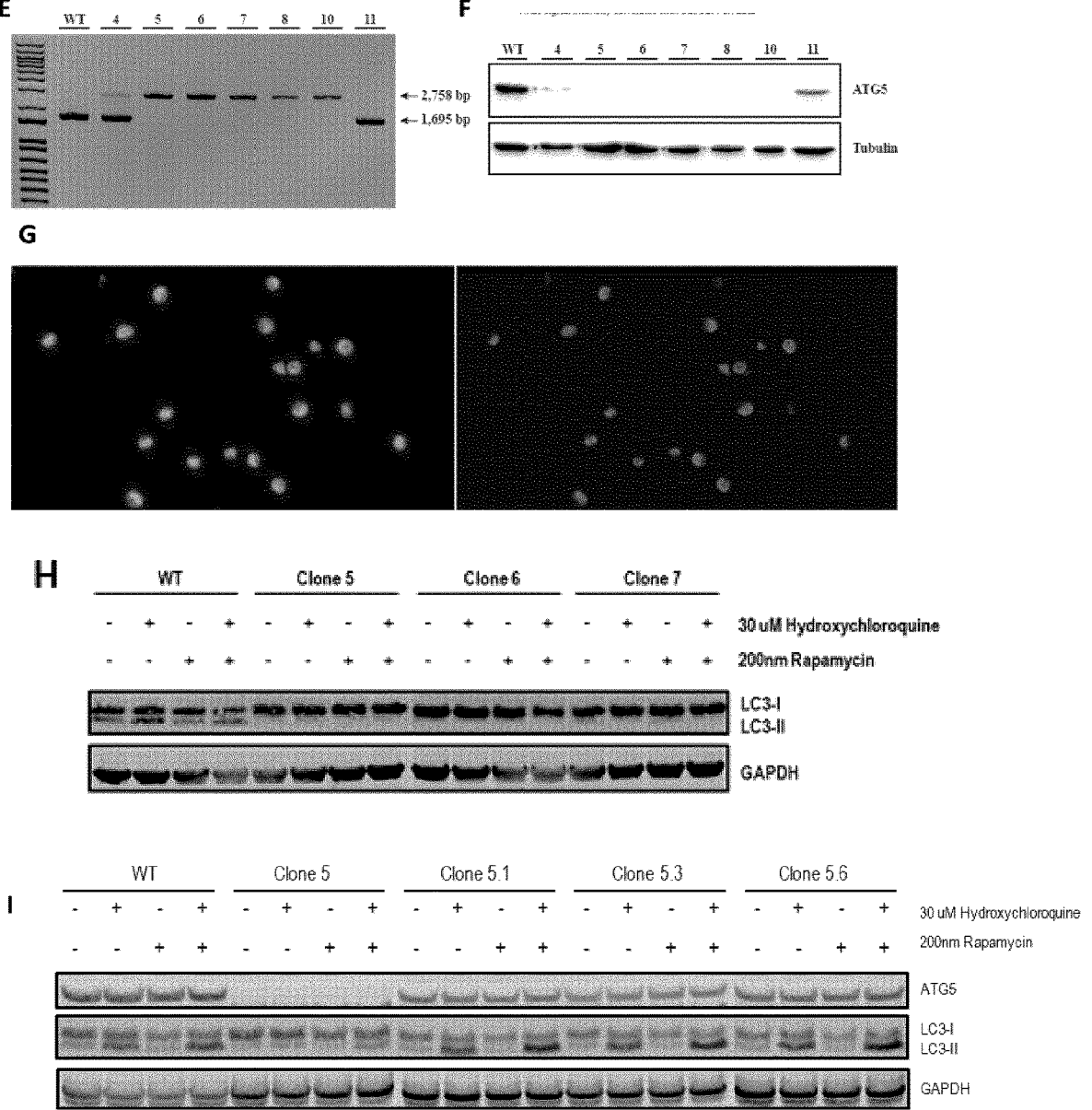

With reference to FIG. 12, a CRISPR-Cas9 strategy and validation for gene-editing at the ATG5 locus was developed for the targeting of the CAR to the ATG5 locus. Concomitant functional knock out of ATG5 and targeted integration of a gene trap vector using CRISPR-Cas9 was confirmed. Panel A shows a schematic of the ATG5 locus and the regions screened to identify functional SpCas9-sgRNAs. Exons E2 and E3 of the ATG5 gene are shown as open boxes. Genomic structure and target regions within intron 2 (I2) of ATG5 are illustrated schematically. A, B, and C denote non-repetitive target DNA sequences used to design sgRNAs using the online CRISPOR tool. Intron 2 was selected as a preferential target region since all reported mRNA isoforms of ATG5 include this region (i.e. this ensures that all potential transcripts are captured).

Panel B of FIG. 12 shows the sgRNA sequences identified by CRISPOR targeting different regions of intron 2 to arrive at the sgRNA sequences shown in Table 2.

TABLE 2

| Example sgRNA sequences for ATG5 ablation via insertion in intron 2. | | | |
|---|---|---|---|
| LocusName | | DNA Sequence (5'-3') | SEQ ID NO |
| I2A | Target 719 | GCTACGGAAAGTCAGATTAC | SEQ ID NO: 1 |
| I2A | Target 696 | GTAATCTGACTTTCCGTAGC | SEQ ID NO: 2 |
| I2A | Target 824 | GCACCGAGTAGTACCACTTG | SEQ ID NO: 3 |
| I2A | Target 950 | AAGTTCGGCAATCTTGTTAC | SEQ ID NO: 4 |
| I2B | Target 905 | CGGATCGCTGCCTAATGTTA | SEQ ID NO: 5 |
| I2B | Target 945 | CCGTTTATGTATCCTTAGTC | SEQ ID NO: 6 |
| I2C | Target 710 | GTCACGTTCTCCTACCTAGT | SEQ ID NO: 7 |

Panel C of FIG. 12 shows the identification of active sgRNAs using the surveyor nuclease assay. In this assay, a mismatch sensitive nuclease is used to determine the frequency of the small insertions and deletions (indels) indicative of nuclease activity. As an example, sgRNA 824 appears to be the most active nuclease for section I2A of intron 2 and was selected for further experiments.

Panel D of FIG. 12 shows a schematic of the ATG5 locus following CAR addition. The first and second schematics show the genomic structure of the CAR-T integration site and donor template. Shown are the locations of the splice acceptor site (SA), 2A self-cleaving peptide sequence (2A), polyadenylation sequence (pA), and homology arms left and right (HA-L, HA-R). The third schematic shows the integrated CAR construct at the ATG5 locus.

Panel E of FIG. 12 shows out-out PCR showing integration of a test SA-2A-mScarlet-pA reporter sequence within intron 2 of ATG5. Complete integration at all alleles is observed for K562 clones 5, 6, 7, 8, 10. Panel F is a Western blot showing loss of ATG5 in K562 clones correlates with complete integration of the mScarlet construct (i.e. loss of ATG5 is observed for clones 5, 6, 7, 8, 10. Panel G is an immunofluorescence image of K562 cells showing nuclear staining (left) and mScarlet expression (right), showing good expression of the mScarlet reporter construct. Panel H is a Western blot showing response to treatment with hydroxychloroquine and/or rapamycin. Loss of LC3-II indicating inhibited autophagic flux is observed in K562 clones 5, 6, 7 (clones 8 and 10 were not tested). Panel I is a Western blot showing that for clones for which an ATG5 cDNA was targeted to an intergenic locus (AAVS1) to restore expression of ATG5 (clones 5.1, 5.3 and 5.6), autophagy was restored as confirmed by the return of LC3-II.

Figure 13:
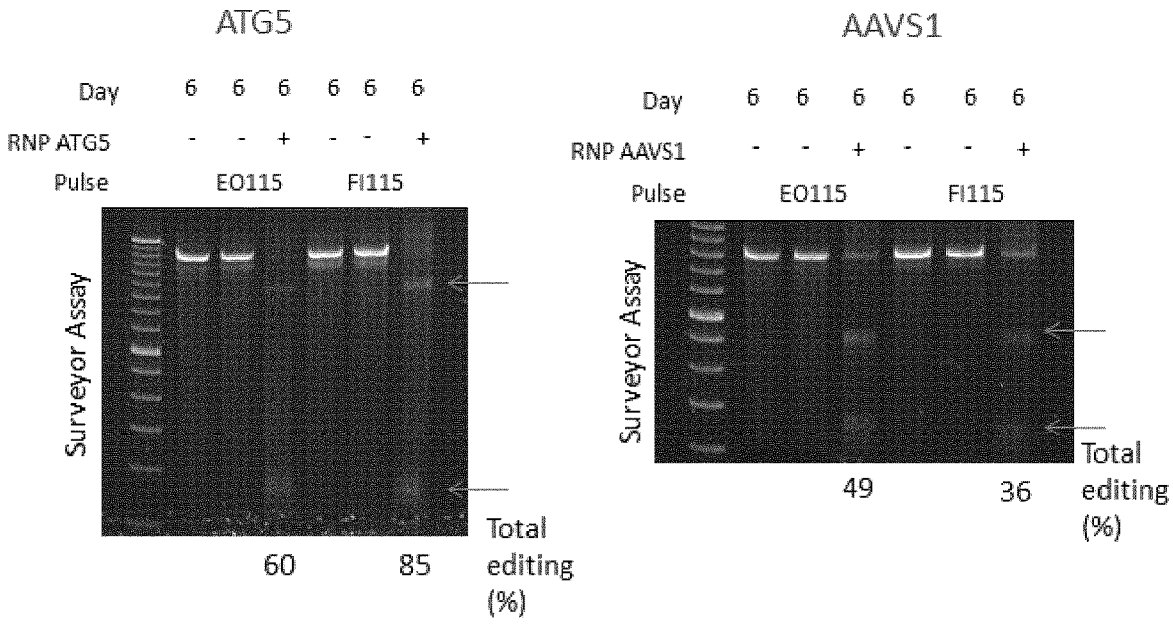
FIG. 13 shows the results of experiments demonstrating the delivery of Cas9 RNP targeting ATG5 in primary T-cells.

FIG. 13 shows the results of experiments demonstrating delivery of Cas9 RNP targeting ATG5 in primary T-cells. Purified CD3 cells stimulated with CD3/CD28 beads were electoporated with recombinant SpCas9 complexed with a chemically modified sgRNA (824) using the amaxa 4D Nucleofector. Two different pulses were tested. Genomic DNA was extracted 3 days post transfection and the Surveyor assay was performed to determine the frequency of indels.

Figure 14:
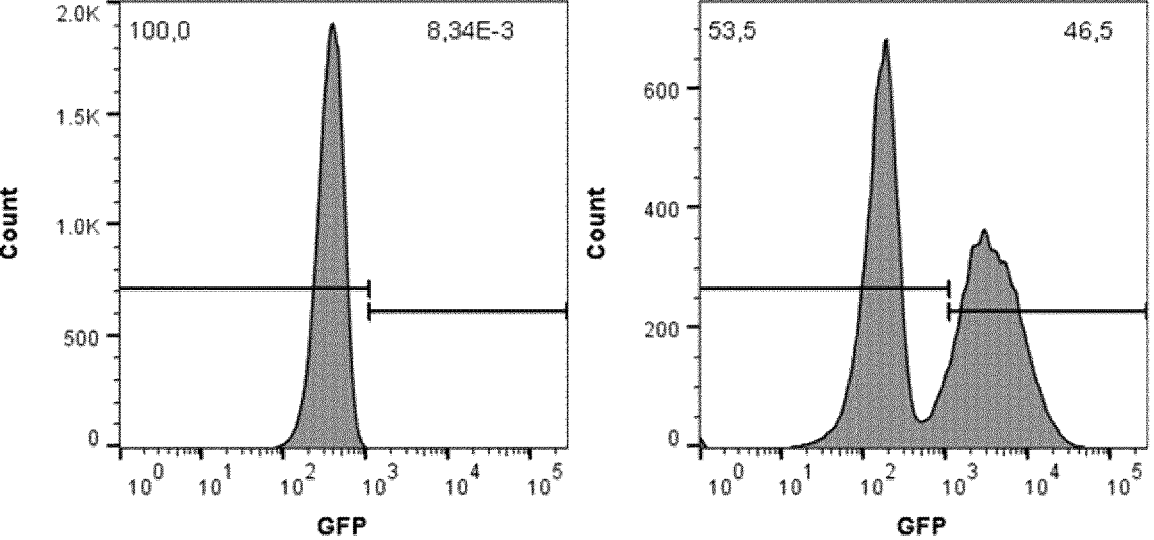
FIG. 14 shows the expression of an example αFR-CAR construct on human T-cells.

FIG. 14 shows the expression of an exemplary αFR-CAR (CD3zBB) with a GFP reporter from Human CD8+ T-cells transduced with lentiviruses encoding the construct. The left panel is empty vector. The right panel is the αFR-CAR construct showing expression of the desired protein on human T-cells.

The sequences of the CAR constructs used to insert the αFR-CAR at the ATG5 locus are given as SEQ ID NOs:8 and 9The sequences of the CAR constructs used to insert the αFR-CAR within the AAVS1 locus as a control are given as SEQ ID NOs:10 and 11. SEQ ID NO:8 encodes a CAR construct having an anti-folate receptor ScFv, a transmembrane domain, a CD27 co-stimulatory domain, and a CD3 intracellular domain. SEQ ID NO:9 encodes a CAR construct having an anti-folate receptor ScFv, a transmembrane domain, a CD28 co-stimulatory domain, and a CD3 intracellular domain. SEQ ID NO:10 encodes a CAR construct having an anti-folate receptor ScFv, a transmembrane domain, a CD27 co-stimulatory domain, and a CD3 intracellular domain. SEQ ID NO:11 encodes a CAR construction having an anti-folate receptor ScFv, a transmembrane domain, a CD28 co-stimulatory domain, and a CD3 intracellular domain.

Figure 15:
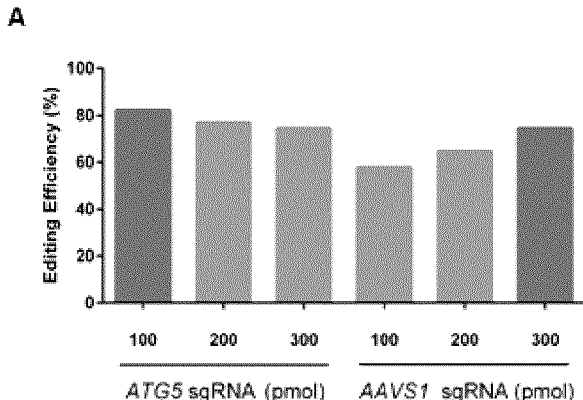
FIG. 15, Panels A-E, show the results of experiments demonstrating efficient targeting of ATG5 and AAVS1 in CD34+ hematopoietic stem cells and activated CD8+ T-cells.
Figure 15:
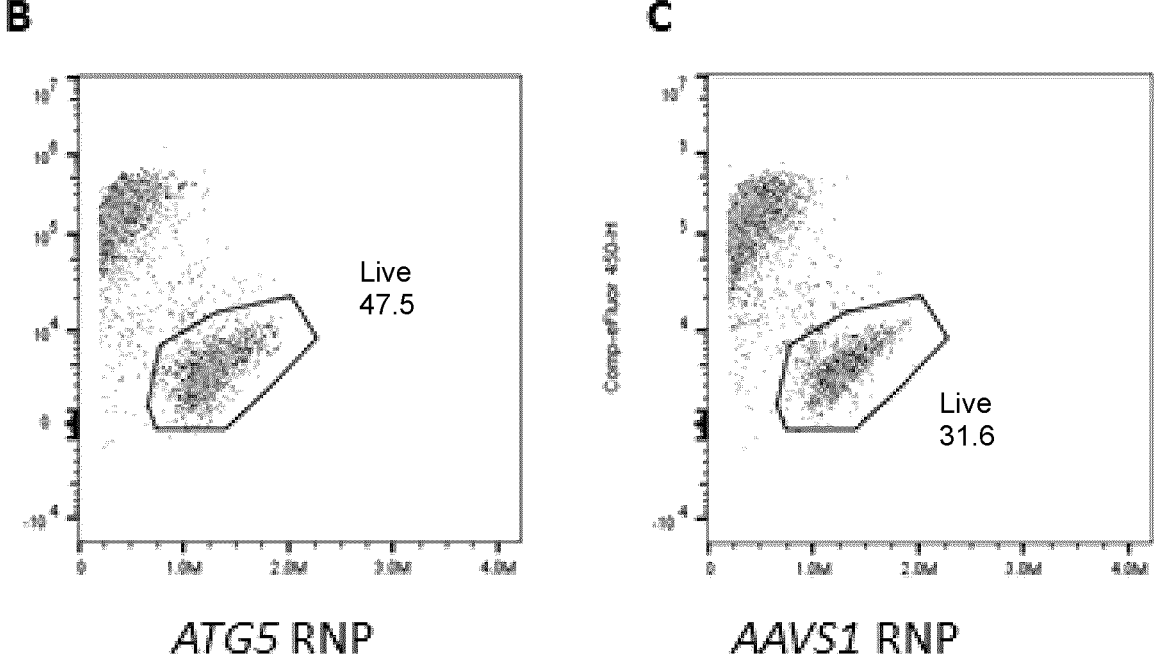
Figure 15:
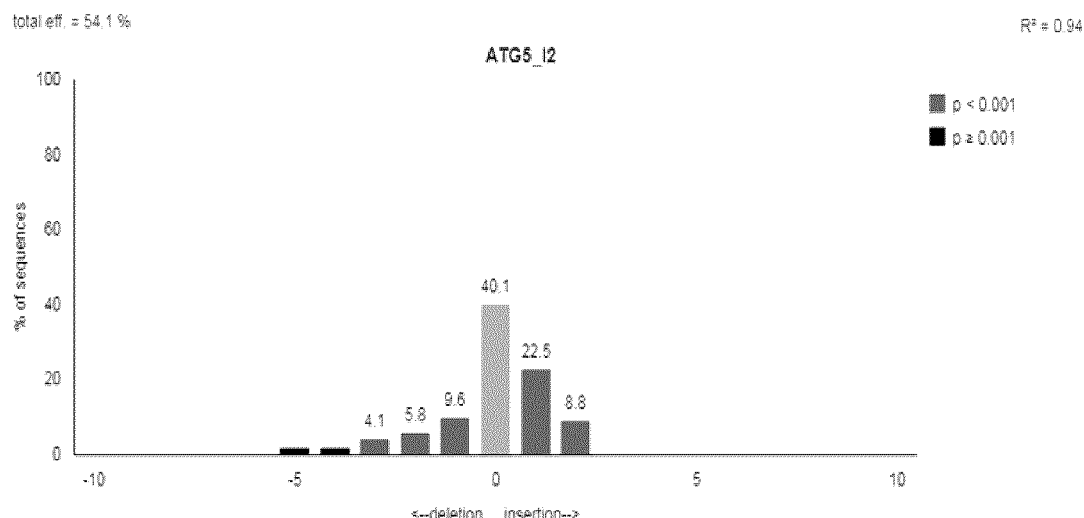
Figure 15:
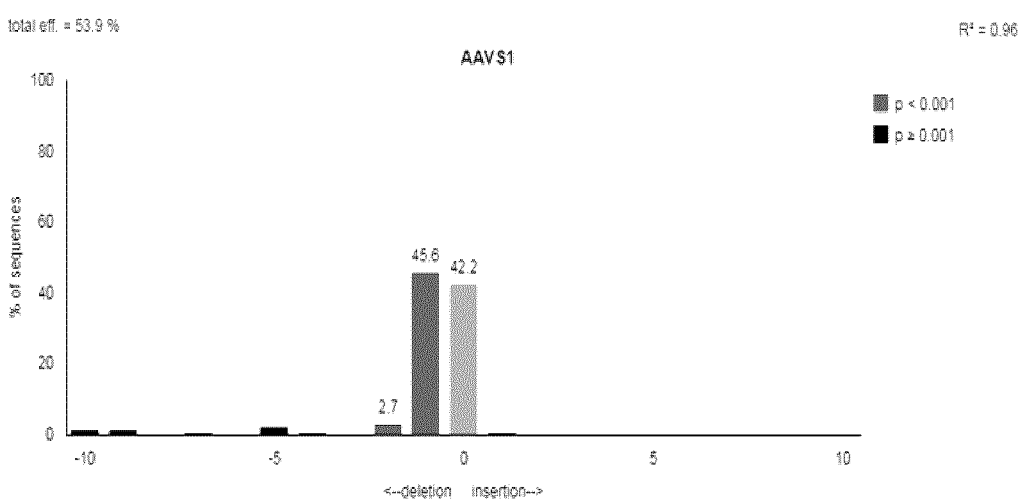

FIG. 15 shows the efficient targeting of ATG5 and AAVS1 in CD34+ hematopoietic stem cells and activated CD8+ T-cells (no donor CAR construct was present in these experiments). Panel A is a histogram showing editing efficiency at ATG5 and AAVS1 in cord blood derived CD34+ HSCs after electroporation with Cas9 protein and 100-300 pmol sgRNA as indicated. Genomic DNA from each target region was amplified and sequenced, and the sequence traces analyzed using the decomposition algorithm TIDE. Panels B and C are flow cytometry dot plots showing 47.5% viability (ATG5) and 31.6% viability (AAVS1) in CD8+ T-cells three days after electroporation with a ribonucleoprotein (RNP) complex consisting of Cas9 protein and sgRNA. Panels D and E are histograms showing 54.1% overall editing efficiency at ATG5 and 53.9% overall editing efficiency at AAVS1 in CD8+ T-cells as determined by TIDE analysis.

Figure 16:
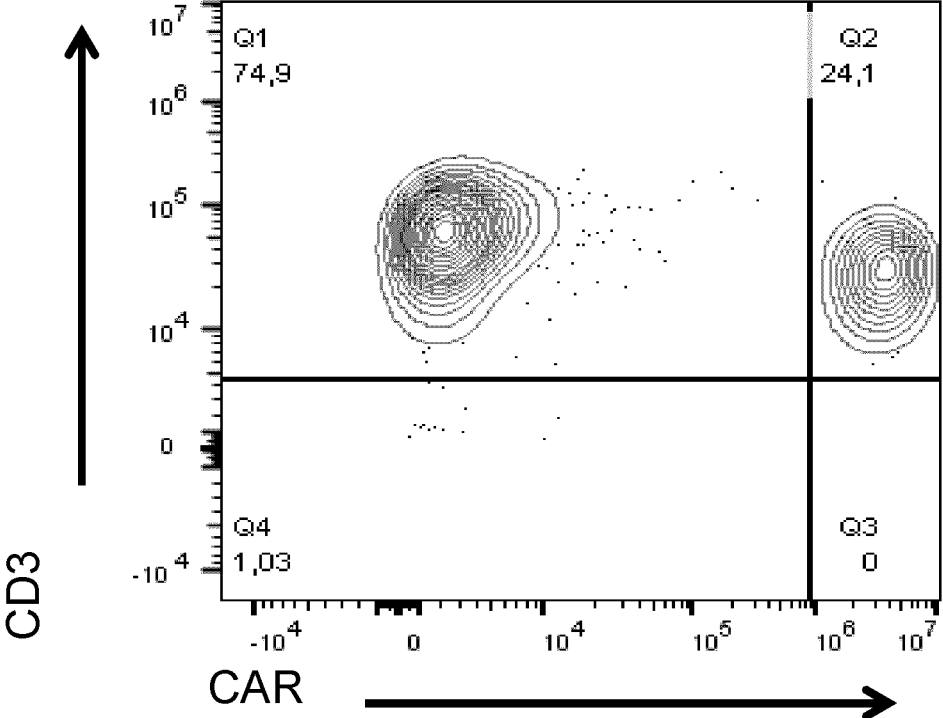
FIG. 16 shows the incorporation of the desired αFR-CAR targeting ATG5 into intron 2 of ATG5 in CD8+ T-cells.

FIG. 16 shows the validation of the incorporation of the CAR construct into intron 2 of ATG5 in healthy donor T-cells. CD8+ T-cells were isolated from healthy donor PBMCs by magnetic bead separation, stimulated with Trans-Act (Miltenyi), and cultured in 100 U/ml IL-2. On day 4 post-activation, the cells were electroporated with an RNP consisting of 100 pmol sgRNA targeting ATG5 and 61 pmol Cas9 protein. 15 minutes post-electroporation, C4-CD28-CD3z AAV (having SEQ ID NO:9) was given at an MOI of 2e5. The cells were expanded for 13 days and then stained for flow cytometry on a Cytek Aurora. The results show that 24.1% of the cells were the desired ATG5$^{-/-}$ αFR-CAR-T-cells.

Figure 17:
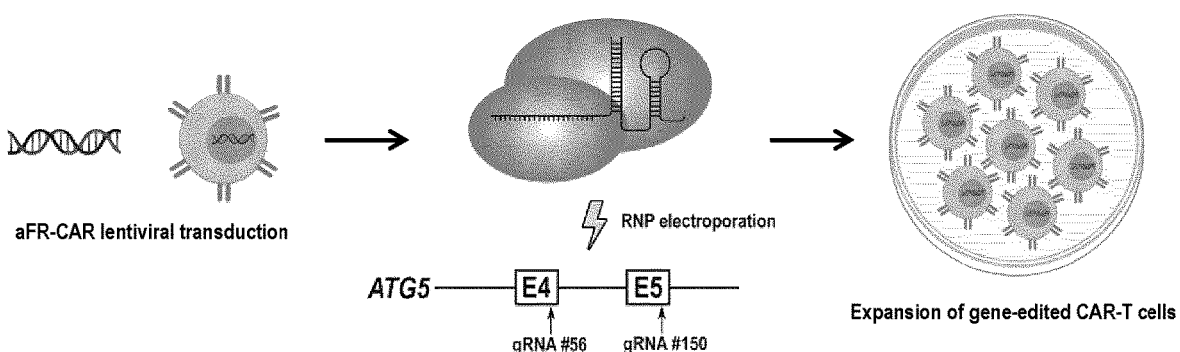
FIG. 17 shows the strategy for incorporating a desired αFR-CAR construct transduced by a lentiviral vector into the T-cell genome followed by electroporation of ATG5 sgRNA into exon 4 or exon 5 of the ATG5 gene to knock out ATG5. Panel A shows the strategy for incorporating the construct into T-cells and knocking out ATG5. Panel B shows the results of TIDE analysis showing the successful deletion at exon 4 of ATG5.
Figure 17:
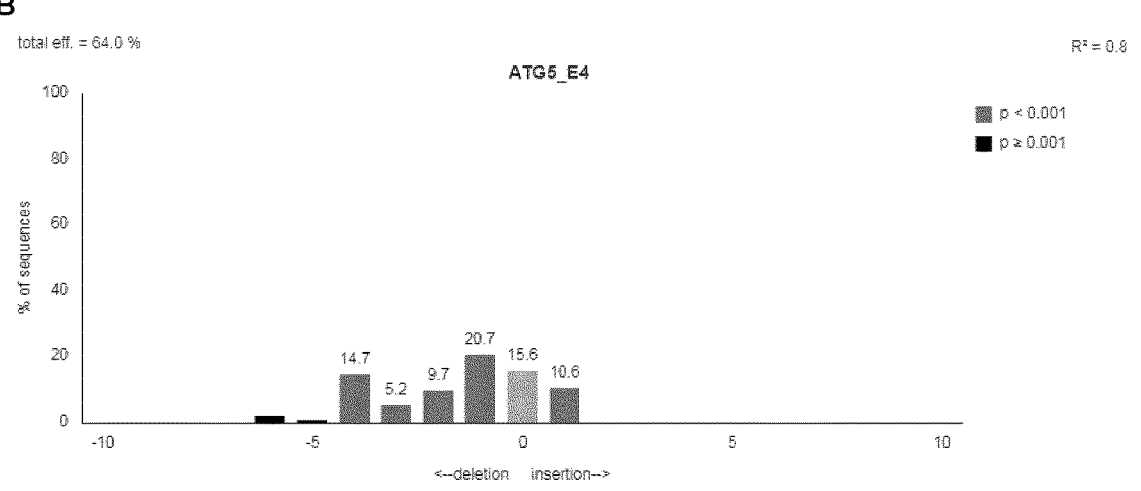

FIG. 17 shows the strategy for incorporating a desired αFR-CAR transduced by a lentiviral vector into the T-cell genome followed by electroporation of sgRNA targeting ATG5 into exon 4 or exon 5 of the ATG5 gene using the sgRNA sequences shown in Table 3. Panel A shows the strategy for incorporating the construct into T-cells and ablating ATG5 at exon 4 (Target 56) or exon 5 (Target 150). Panel B shows the results of TIDE analysis showing the successful deletion at exon 4 of ATG5 using an sgRNA having the sequence of SEQ ID NO:24 (Target 56).

TABLE 3

| Example sgRNA sequences for ATG5 ablation via insertion in exon 4 or exon 5. | | | |
| --- | --- | --- | --- |
| LocusName | | DNA Sequence (5'-3') | SEQ ID NO |
| E4 | Target 56 | CATCAAGTTCAGCTCTTCCT | SEQ ID NO: 24 |
| E5 | Target 150 | GATCACAAGCAACTCTGGAT | SEQ ID NO: 25 |

The foregoing example demonstrates that a desired antigen targeting receptor construct can be integrated into the genome of a lymphocyte such as a T-cell at one locus in the genome, while an autophagy gene such as ATG5 can be knocked out at a different locus using CRISPR-Cas gene editing.

REFERENCES

The following references are of interest with respect to the subject matter described herein. Each one of the following references is incorporated by reference herein in its entirety.

1. Geyer M B, Brentjens R J. 2016. Review: Current clinical applications of chimeric antigen receptor (CAR) modified T-cells. *Cytotherapy* 18: 1393-409
2. Kershaw M H, et al., 2006. A phase I study on adoptive immunotherapy using gene-modified T-cells for ovarian cancer. *Clin Cancer Res* 12: 6106-15
3. Zhao Z, et al., 2015. Structural Design of Engineered Costimulation Determines Tumor Rejection Kinetics and Persistence of CAR T-cells. *Cancer Cell* 28: 415-28
4. Milne K, et al., 2009. Systematic analysis of immune infiltrates in high-grade serous ovarian cancer reveals CD20, FoxP3 and TIA-1 as positive prognostic factors. *PLoS One* 4: e6412

5. Cheung A, et al., 2016. Targeting folate receptor alpha for cancer treatment. *Oncotarget*

6. Newick K, et al., 2017. CAR T-cell Therapy for Solid Tumors. *Annu Rev Med* 68: 139-52

7. Townsend K N, et al., 2013. Markers of T-cell infiltration and function associate with favorable outcome in vascularized high-grade serous ovarian carcinoma. *PLoS One* 8: e82406

8. Vander Heiden M G, DeBerardinis R J. 2017. Understanding the Intersections between Metabolism and Cancer Biology. *Cell* 168: 657-69

9. Chang C H, Pearce E L. 2016. Emerging concepts of T-cell metabolism as a target of immunotherapy. *Nat Immunol* 17: 364-8

10. Chang C H, et al., 2015. Metabolic Competition in the Tumor Microenvironment Is a Driver of Cancer Progression. *Cell* 162: 1229-41

11. MacPherson S, et al., 2017. STAT3 regulation of citrate synthase is essential during the initiation of lymphocyte cell growth. *Cell Rep* 19(5):910-918

12. Ma E H, et al., 2017. Serine Is an Essential Metabolite for Effector T-cell Expansion. *Cell Metab* 25: 345-57

13. Scharping N E, et al., 2016. The Tumor Microenvironment Represses T-cell Mitochondrial Biogenesis to Drive Intratumoral T-cell Metabolic Insufficiency and Dysfunction. *Immunity*

14. Lum J J, DeBerardinis R J, Thompson C B. 2005. Autophagy in metazoans: cell survival in the land of plenty. *Nat Rev Mol Cell Biol* 6: 439-48

15. Pua H H, He Y W. 2009. Autophagy and lymphocyte homeostasis. *Curr Top Microbiol Immunol* 335: 85-105

16. Schlie K, et al., 2015. Survival of effector CD8+ T-cells during influenza infection is dependent on autophagy. *J Immunol* 194: 4277-86

17. Puleston D J, et al., 2014. Autophagy is a critical regulator of memory CD8+ T-cell formation. *Elife* 3

18. Qu X, et al., 2003. Promotion of tumorigenesis by heterozygous disruption of the beclin 1 autophagy gene. *J Clin Invest* 112: 1809-20

19. Takamura A, et al., 2011. Autophagy-deficient mice develop multiple liver tumors. *Genes Dev* 25: 795-800

20. Macintyre A N, et al., 2014. The glucose transporter Glut1 is selectively essential for CD4 T-cell activation and effector function. *Cell Metab* 20: 61-72

21. Hultquist J F, et al., 2016. A Cas9 Ribonucleoprotein Platform for Functional Genetic Studies of HIV-Host Interactions in Primary Human T-cells. *Cell Rep* 17: 1438-52

22. Eyquem J, et al., 2017. Targeting a CAR to the TRAC locus with CRISPR/Cas9 enhances tumour rejection. *Nature* 543: 113-7.

23. DeVorkin L, et al., 2019. Autophagy regulation of metabolism is required for CD8+ T-cell anti-tumour immunity. *Cell Rep* 27(2):502-513.

24. Stadtmauer, E A, et al., 2020. CRISPR-engineered T cells in patients with refractory cancer. Science 6 Feb. 2020. DOI: 10.1126/science.aba7365.

25. Schlie et al., 2015. Survival of effector CD8+ T-Cells during influenza infection is dependent on autophagy. *J. Immunol.* 194(9):4277-4286.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

The invention claimed is:

1. A lymphocyte comprising an antigen targeting receptor and a suppressed autophagy gene, wherein the antigen targeting receptor comprises a chimeric antigen receptor (CAR) or an engineered T-cell receptor.

2. The lymphocyte as defined in claim 1, comprising a nucleic acid encoding the antigen targeting receptor inserted within a locus of the autophagy gene to disrupt expression of the autophagy gene.

3. The lymphocyte as defined in claim 2, wherein the nucleic acid encoding the antigen targeting receptor is inserted within the locus of the autophagy gene so that expression of the antigen targeting receptor is regulated by an endogenous promoter of the autophagy gene.

4. The lymphocyte as defined in claim 1, wherein the nucleic acid encoding the antigen targeting receptor is inserted within an exon of the autophagy gene.

5. The lymphocyte as defined in claim 1, wherein the nucleic acid encoding the antigen targeting receptor is inserted within an intron of the autophagy gene, optionally wherein the autophagy gene is ATG5 and the nucleic acid encoding the antigen targeting receptor is inserted within intron 2 of the ATG5 gene, and further optionally where the nucleic acid used to insert the antigen targeting receptor has the sequence of one of SEQ ID NO:8 or SEQ ID NO:9.

6. The lymphocyte as defined in claim 1, wherein the autophagy gene is at a first locus of a genome of the lymphocyte and the lymphocyte has been genetically modified to contain a nucleic acid encoding the antigen targeting receptor at a second locus of the genome, the first locus being different from the second locus.

7. The lymphocyte as defined in claim 6, wherein expression of the antigen targeting receptor is regulated by a heterologous promoter.

8. The lymphocyte as defined in claim 1, wherein the autophagy gene is ablated, or wherein the autophagy gene is suppressed by RNAi.

9. The lymphocyte as defined in claim 1, wherein:
the lymphocyte comprises a lymphocyte with activity in killing tumor cells;
the lymphocyte comprises a cytotoxic lymphocyte; and/or
the lymphocyte comprises a T-cell, a natural killer (NK) cell, or a B-cell, optionally wherein the T-cell comprises a T-cell derived from an induced pluripotent stem cell, a CD34+T-cell, a CD4+T-cell, a CD8+T-cell, a Treg cell, a tissue-resident memory T-cell (TRM), or a natural killer T-cell (NKT).

10. The lymphocyte as defined in claim 1, wherein the autophagy gene is ULK1, ULK2, ULK3, FIP200, Vps34, Beclin-1, p150, UVRAG, ATG1, ATG4, ATG5, ATG7, ATG8, ATG9, ATG10, ATG12, ATG13, ATG14L, ATG16L, ATG16L1, ATG18, VMP1, or GABARAP.

11. The lymphocyte as defined in claim 1, wherein the antigen targeting receptor is specific for a tumor-specific antigen, optionally wherein the tumor-specific antigen comprises the folate receptor (FR), the α-folate receptor, the B-folate receptor, the y-folate receptor, CD19, CD20, CD133, CD138, CEA, Claudin 18.2, EGFR, EGFRvlll, EphA2, EpCAM, GD2, GPC3, HER2, MSLN, MG7, MUC1, NY-ESO-1, LMP1, prostate specific membrane antigen (PSMA), Fra, NKG2DI, BCMA, IL13Ralpha2, LeY, CD70, B7-H3, ROR1, or PSCA.

12. The lymphocyte as defined in claim 1, wherein the antigen targeting receptor comprises a chimeric antigen receptor (CAR), and wherein the CAR is an α-folate receptor CAR, and wherein optionally the nucleotide construct used to insert the CAR in the lymphocyte has the nucleic acid sequence of either one of SEQ ID NO:8 or SEQ ID NO:9.

13. The lymphocyte as defined in claim 1, wherein the autophagy gene is ATG5, ATG14, or ATG16L1.

14. The lymphocyte as defined in claim 13, wherein the lymphocyte is a CD4+T-cell or a CD8+T-cell.

15. A method of making the lymphocyte of claim 1 for use in immunotherapy, the method comprising a step of modifying the lymphocyte to suppress the autophagy gene, and a step of modifying the lymphocyte to express the antigen targeting receptor.

16. The method as defined in claim 15, wherein the step of modifying the lymphocyte to suppress the autophagy gene comprises using a gene editing method to insert a nucleic acid encoding the antigen targeting receptor at a locus of the autophagy gene, optionally wherein the gene editing method is used to insert the nucleic acid encoding the antigen targeting receptor so that expression of the antigen targeting receptor is regulated by an endogenous promoter of the autophagy gene.

17. The method as defined in claim 15, wherein the step of modifying the lymphocyte to express the antigen targeting receptor comprises inserting a nucleic acid encoding the antigen targeting receptor within a genome of the lymphocyte at a first locus, and wherein the step of modifying the lymphocyte to suppress an autophagy gene comprises knocking out the autophagy gene at a second locus of the genome, the second locus being different from the first locus.

18. A method of conducting cancer immunotherapy comprising administering the lymphocyte as defined in claim 11 to a mammalian subject.

19. A method of conducting cancer immunotherapy as defined in claim 18, wherein the cancer is breast cancer, ovarian cancer, prostate cancer, or lung cancer.

* * * * *